(12) United States Patent
Bellicchi et al.

(10) Patent No.: US 11,173,051 B2
(45) Date of Patent: Nov. 16, 2021

(54) APPARATUS AND METHODS FOR THREE DIMENSIONAL PLASTHESIS PROSTHESES

(71) Applicant: Indiana University Research and Technology Corporation, Indianapolis, IN (US)

(72) Inventors: Travis Dean Bellicchi, Indianapolis, IN (US); Zebulun Maxwell Wood, Westfield, IN (US); Cade Bradley-Thomas Jacobs, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 255 days.

(21) Appl. No.: 15/767,341

(22) PCT Filed: Oct. 14, 2016

(86) PCT No.: PCT/US2016/056979
§ 371 (c)(1),
(2) Date: Apr. 10, 2018

(87) PCT Pub. No.: WO2017/066523
PCT Pub. Date: Apr. 20, 2017

(65) Prior Publication Data
US 2018/0296367 A1    Oct. 18, 2018

Related U.S. Application Data

(60) Provisional application No. 62/242,522, filed on Oct. 16, 2015.

(51) Int. Cl.
*A61F 2/50* (2006.01)
*B33Y 80/00* (2015.01)
(Continued)

(52) U.S. Cl.
CPC .......... *A61F 2/5046* (2013.01); *A61C 9/0053* (2013.01); *A61C 13/0013* (2013.01);
(Continued)

(58) Field of Classification Search
None
See application file for complete search history.

(56) References Cited

U.S. PATENT DOCUMENTS

| 4,941,212 A | 7/1990 | Liff |
| 2014/0163445 A1 | 6/2014 | Pallari et al. |

(Continued)

FOREIGN PATENT DOCUMENTS

| WO | WO 2014/102779 A2 | 7/2014 |
| WO | WO2015/009235 A1 | 1/2015 |
| WO | WO 2015/077881 A1 | 6/2015 |

OTHER PUBLICATIONS

International Preliminary Report on Patentability issued by the International Bureau of WIPO, Switzerland, dated Apr. 17, 2018 for International Application No. PCT/US2016/056979; 7 pages.

(Continued)

*Primary Examiner* — Matthew J Daniels
*Assistant Examiner* — Paul Spiel
(74) *Attorney, Agent, or Firm* — Faegre Drinker Biddle & Reath LLP

(57) ABSTRACT

A prosthesis, radiation bolus, pre-surgical model, or burn mask formed using a rapid prototyping device, such as a three-dimensional printer. In some exemplary aspects, the prosthesis includes a scaffolding and a coating at least partially covering the scaffolding. Methods and systems for forming the prosthesis, radiation bolus, pre-surgical model, or burn mask are also provided.

7 Claims, 52 Drawing Sheets

(51) Int. Cl.
*A61N 5/10* (2006.01)
*A61F 13/12* (2006.01)
*A61F 2/00* (2006.01)
*A61C 9/00* (2006.01)
*A61C 13/00* (2006.01)
*A61F 2/78* (2006.01)
*A61C 13/34* (2006.01)

(52) U.S. Cl.
CPC .............. *A61F 2/0059* (2013.01); *A61F 2/50* (2013.01); *A61F 2/78* (2013.01); *A61F 13/12* (2013.01); *A61F 13/122* (2013.01); *A61N 5/1029* (2013.01); *B33Y 80/00* (2014.12); *A61C 13/34* (2013.01); *A61F 2002/5001* (2013.01); *A61F 2002/505* (2013.01); *A61F 2002/5053* (2013.01); *A61F 2002/7806* (2013.01); *A61F 2002/7862* (2013.01); *A61F 2002/7887* (2013.01); *A61F 2240/002* (2013.01); *A61F 2240/004* (2013.01); *A61F 2240/008* (2013.01); *A61F 2250/0029* (2013.01)

(56) References Cited

U.S. PATENT DOCUMENTS

| | | | |
|---|---|---|---|
| 2015/0343709 A1* | 12/2015 | Gerstle | G06F 19/3481 700/97 |
| 2016/0106536 A1* | 4/2016 | Chui | A61B 5/1073 623/9 |
| 2019/0282832 A1* | 9/2019 | Robar | B29C 64/106 |

OTHER PUBLICATIONS

International Search Report and Written Opinion issued by the ISA/US, Commissioner for Patents, dated Feb. 7, 2017, for International Application No. PCT/US2016/056979; 10 pages.

* cited by examiner

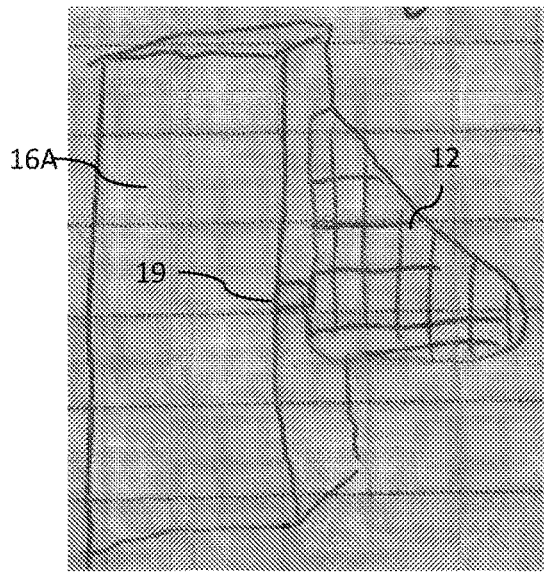
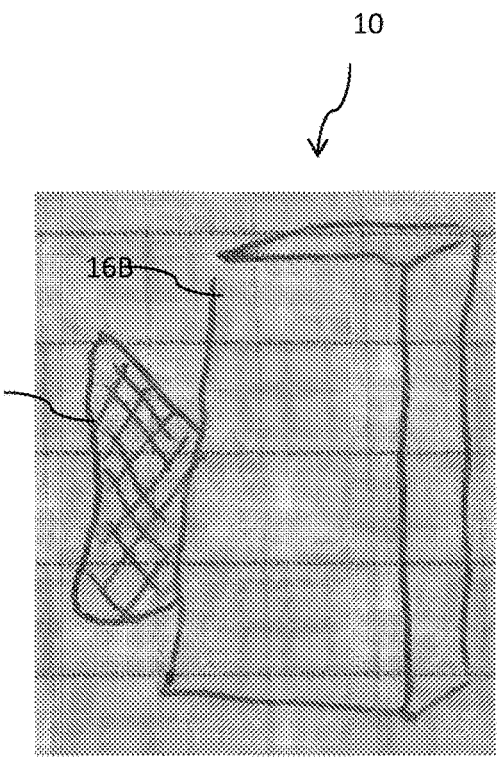
Fig. 2F                Fig. 2G
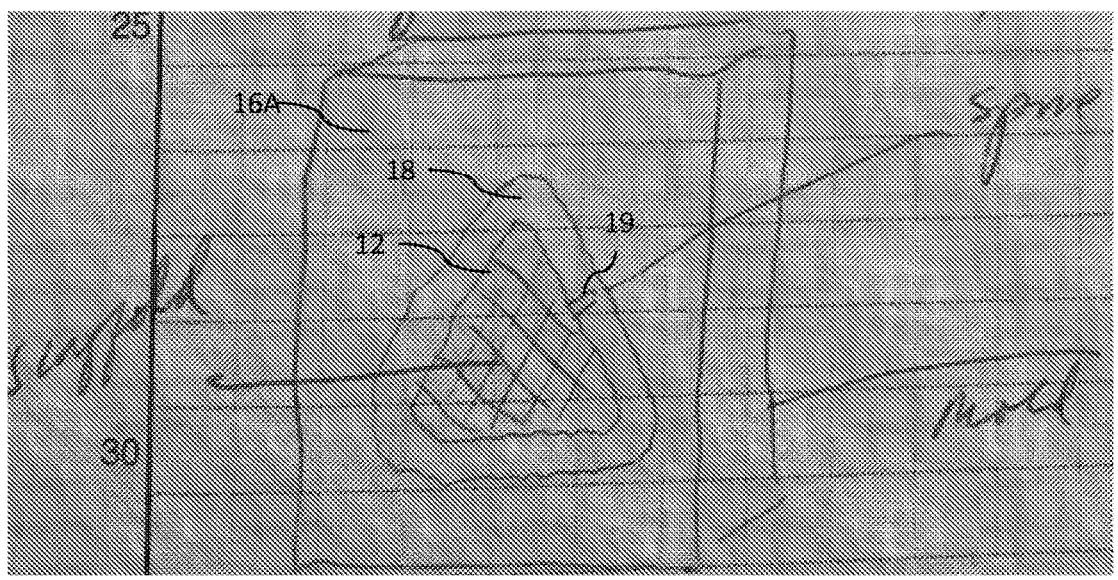
Fig. 2H

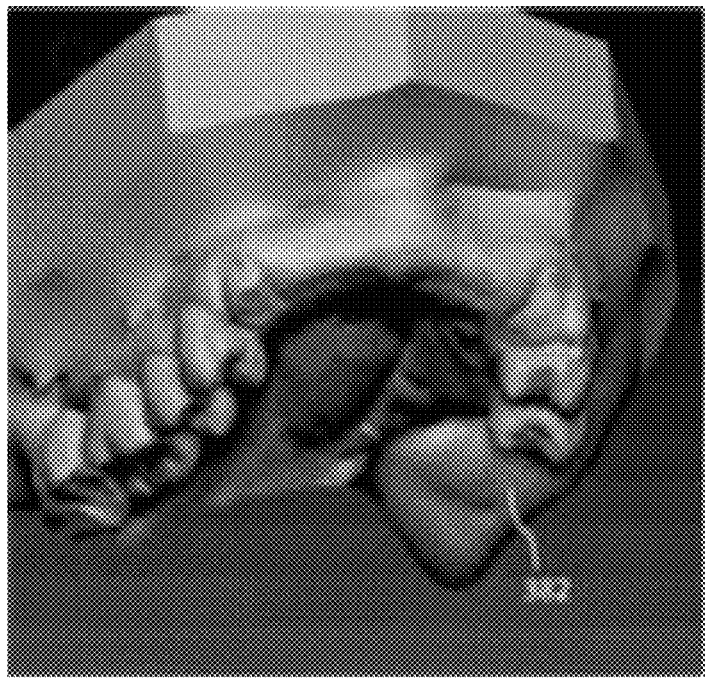
Fig. 44
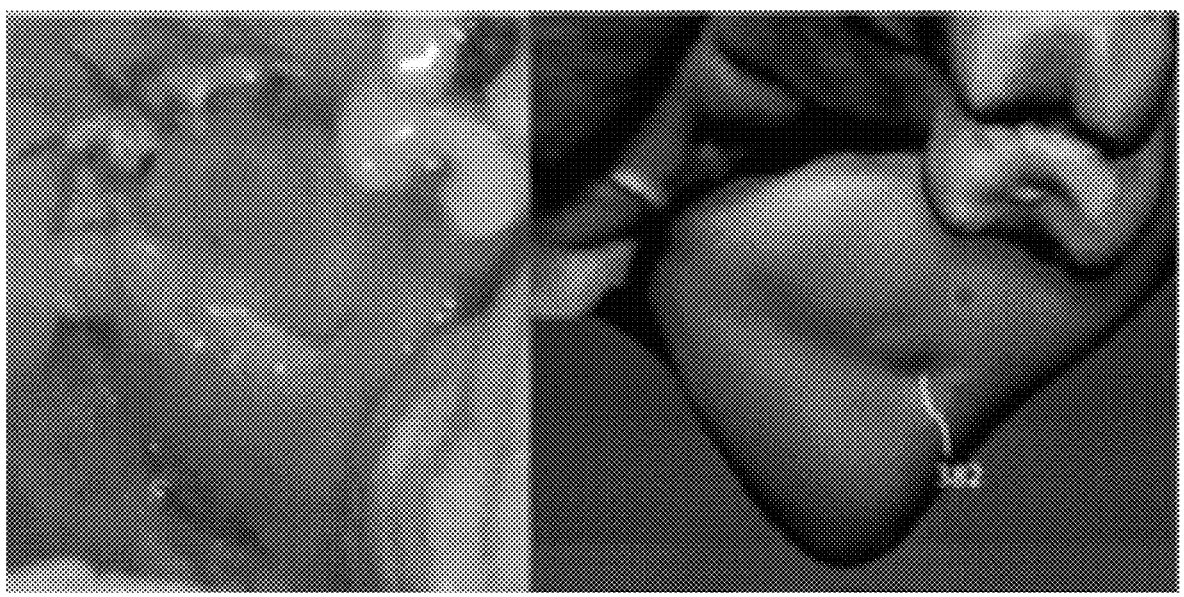
Fig. 45A                    Fig. 45B

APPARATUS AND METHODS FOR THREE DIMENSIONAL PLASTHESIS PROSTHESES

CROSS-REFERENCE TO RELATED APPLICATIONS

This application is a U.S. National Stage Application of International Patent Application No. PCT/US2016/056979, filed Oct. 14, 2016, which claims the benefit of U.S. Provisional Patent Application No. 62/242,522, filed Oct. 16, 2015, the disclosures each of which is expressly incorporated by reference in its entirety.

FIELD

This disclosure relates to prostheses, radiation boluses, pre-surgical models, and burn masks, and more particularly, to apparatus and methods for electronically designing and forming the prostheses, radiation boluses, pre-surgical models, and burn masks using a rapid prototyping device.

BACKGROUND AND SUMMARY

Maxillofacial silicone elastomer prostheses are used to replace facial features, such as for patients in which such features are congenitally absent, surgically removed due to disease, or lost due to trauma.

An exemplary typical method of forming a prosthesis is shown in FIGS. 1A-1J. A patient in need of a mandibular prosthesis is shown in FIG. 1. As shown in FIG. 1B, an impression of the patient's face is taken using polyvinyl siloxane (PVS) and dental gypsum, each available from Factor II, Inc., Lakeside, Ariz. The formed impression is shown in FIG. 1C. As shown in FIG. 1D, a cast was made in Type IV dental stone, available under the trade name Silky-Rock from Whip Mix Corp., Louisville, Ky.

As shown in FIG. 1E, sculpting clay, available under the trade name NSP from Chavant, Farmingdale, N.J., was used to form a model based on pre-surgical patient photos. As shown in FIGS. 1F and 1G, the clay model is used to form an exterior mold. As shown in FIGS. 1H and 1I, the exterior mold and cast shown in FIG. 1D are used to form a mold cavity, into which a silicone material is poured to form the prosthesis. The prosthesis may then be painted and finished, as shown in FIG. 1J.

In a typical process, such as shown in FIG. 1A-1J, the process can take a relatively long amount of time and suffer from soft tissue distortion from forming the impression, as shown in FIG. 1B. In addition, multiple office visits are required of the patient, including a relatively long visit for the impression process.

Improvements in the foregoing are desired.

In one exemplary aspect, a method of forming a prosthesis, radiation bolus, pre-surgical model, or burn mask is provided. The method may include electronically receiving data from a topographic scan of a patient, electronically designing a digital model of a prosthesis, radiation bolus, pre-surgical model, or burn mask for the patient; and forming at least a portion of the prosthesis, radiation bolus, pre-surgical model, or burn mask using rapid prototyping methods based on the digital model of the prosthesis, radiation bolus, pre-surgical model, or burn mask. The forming may include printing at least a portion of the prosthesis using a rapid prototyping device based on the digital model of the prosthesis.

In a more particular aspect of any of the above aspects of the disclosure, the method further includes electronically receiving an image related to a reference image of the patient, wherein electronically designing the digital model includes designing the prosthesis, radiation bolus, pre-surgical model, or burn mask at least partially based on the reference image of the patient.

In a more particular aspect of any of the above aspects of the disclosure, the method further includes electronically removing artifacts from the data from the topographic scan of the patient. In a more particular aspect of any of the above aspects of the disclosure, electrically receiving data from a topographic scan of the patient further comprises capturing images of the patient from multiple angles using a photogrammetry system. In a more particular aspect of any of the above aspects of the disclosure, the method includes electronically receiving data from a CT scan or MRI of a patient, wherein electronically designing the digital model of the prosthesis, radiation bolus, pre-surgical model, or burn mask includes designing the prosthesis, radiation bolus, pre-surgical model, or burn mask at least partially based on the data from the topographic scan of the patient and the CT scan or MRI of the patient.

In a more particular aspect of any of the above aspects of the disclosure, the rapid prototyping method is selected from the group consisting of three dimensional printing, additive manufacturing, stereolithography (SLA), fused deposition modeling (FDM), selective laser sintering (SLS), selective laser melting (SLM), electronic beam melting (EBM), laminated object manufacturing (LOM), continuous liquid interface production (CLIP), and subtractive manufacturing methods such as CNC milling and melting. In a more particular aspect of any of the above aspects of the disclosure, the polymer material is selected from the group consisting of: polylactic acid, acrylonitrile butadiene styrene, and methacrylate polymers.

In some aspects, the prosthesis, radiation bolus, pre-surgical model, or burn mask is a prosthesis including a scaffolding formed from a polymer and a coating at least partially covering the scaffolding, wherein printing includes printing the scaffolding structure for the prosthesis, and wherein the method further comprises at least partially covering the scaffolding structure with the coating. In a further aspect, printing further includes printing a mold defining a mold cavity, and the method further includes positioning the scaffolding in the mold cavity; filling the mold cavity with a silicone material; and curing the silicone material to form the coating. In a more particular aspect, the prosthesis is a maxillofacial prosthesis. In a more particular aspect of any of the above aspects of the disclosure, printing further includes printing a mold defining a mold cavity, the method further comprising: positioning the scaffolding in the mold cavity; filling the mold cavity with a silicone material; and curing the silicone material to form the coating.

In a more particular aspect of any of the above aspects of the disclosure, the prosthesis, radiation bolus, pre-surgical model, or burn mask is a radiation bolus.

In a more particular aspect of any of the above aspects of the disclosure, the prosthesis, radiation bolus, pre-surgical model, or burn mask is a pre-surgical model, and the method further includes forming a surgical guide based in part on the pre-surgical model.

In a more particular aspect of any of the above aspects of the disclosure, the prosthesis, radiation bolus, pre-surgical model, or burn mask is a burn mask and wherein printing a portion of the burn mask includes printing a three-dimensional model of the topographical scan of the patient and forming a pliable plastic sheet over the three-dimensional model in a thermoforming or vacuum forming machine.

In one aspect of the disclosure, a prosthesis, radiation bolus, pre-surgical model, or burn mask is provided. The prosthesis, radiation bolus, pre-surgical model, or burn mask is at least partially formed using a rapid prototyping method, such as three dimensional printing, additive manufacturing, stereolithography (SLA), fused deposition modeling (FDM), selective laser sintering (SLS), selective laser melting (SLM), electronic beam melting (EBM), laminated object manufacturing (LOM), continuous liquid interface production (CLIP), and subtractive manufacturing methods such as CNC milling and melting. In one aspect, the prosthesis, radiation bolus, pre-surgical model, or burn mask is at least partially formed using data from a topographic scan of a patient.

In a more particular aspect, the a prosthesis, radiation bolus, pre-surgical model, or burn mask is a prosthesis including a scaffolding formed using a rapid prototyping method and a coating at least partially covering the scaffolding. In a more particular aspect of the disclosure, the prosthesis is a maxillofacial prosthesis. In a more particular aspect of any of the above aspects of the disclosure, the coating comprises a platinum-catalyzed silicone. In a more particular aspect of any of the above aspects, the scaffolding comprises at least one polymer selected from the group consisting of: polylactic acid, acrylonitrile butadiene styrene, and methacrylate polymers.

In a more particular aspect of any of the above aspects, the prosthesis comprises a first zone and a second zone, wherein the first zone has a flexibility greater than a flexibility of the second zone. In a more particular aspect of any of the above aspects, the first and the second zone each have a flexibility similar to a flexibility corresponding to at least one of a bone, a muscle, skin, or fat. In a more particular aspect of any of the above aspects, the prosthesis comprises a first zone including a first scaffolding and a second zone including a second scaffolding, wherein the first and second scaffolding are formed from different polymers. In a more particular aspect of any of the above aspects, the scaffolding comprises a plurality of geometries selected from the group consisting of: squares, triangles, trapezoids, rectangles, parallelograms, circles, diamonds, pentagons, hexagons, octagons, heptagons, ellipse, and three-dimensional shapes formed from the forgoing. In a more particular aspect, the first zone and the second zone independently correspond to a portion of a natural anatomy, such as bone, muscle, skin, fat, and other soft tissue, and more particularly, bone, buccinators muscle, and lips.

In one exemplary aspect of the disclosure, a system for forming a prosthesis is provided. The prosthesis illustratively includes a scaffolding formed from a polymer and a coating at least partially covering the scaffolding. In a more particular aspect of the disclosure, the prosthesis is a maxillofacial prosthesis. The system includes a scanner configured to capture topographical information relating to a patient, a design module configured for electronically designing a digital model of the prosthesis; and a rapid prototyping device configured to form the scaffolding from the polymer based on the digital model. In a more particular aspect of any of the above aspects of the disclosure, the scanner is selected from the group consisting of: a photogrammetry system, a CT scanner, an MRI scanner, and a no-contact laser scanner. In a more particular aspect of any of the above aspects of the disclosure, the rapid prototyping device is a three dimensional printer or computer numerical control (CNC) machine. In a more particular aspect of any of the above aspects of the disclosure, the polymer material is selected from the group consisting of: polylactic acid, acrylonitrile butadiene styrene, and methacrylate polymers and the coating is formed from a silicone material. In a more particular aspect of any of the above aspects of the disclosure, the digital model of the prosthesis includes a digital model of the scaffolding and a digital model of a mold, and wherein the rapid prototyping device is configured to form the scaffolding using an additive or subtractive manufacturing method based on the digital model of the scaffolding and to form the mold based on the digital model of the mold. In a more particular aspect of any of the above aspects of the disclosure, the additive manufacturing method is selected from stereolithography (SLA), fused deposition modeling (FDM), selective laser sintering (SLS), selective laser melting (SLM), electronic beam melting (EBM), laminated object manufacturing (LOM), continuous liquid interface production (CLIP), and the subtractive manufacturing method is selected from CNC milling and melting. In a more particular aspect of any of the above described aspects of the disclosure, the digital model of the prosthesis includes a digital model of the scaffolding and a digital model of a mold, and wherein the three-dimensional printer is configured to print the scaffolding based on the digital model of the scaffolding and to print the mold based on the digital model of the mold.

It will be appreciated that numerous modifications to the abovementioned aspects of the disclosure may be made without departing from the scope of the disclosure as defined in the appended claims. Moreover, any one or more of the above described aspects could be combined with one or more of the other aspects to suit a particular application.

Optional and/or preferred features may be used in other combinations beyond those described herein, and optional and/or preferred features described in relation to one aspect of the disclosure may also be present in another aspect or aspect of the disclosure, where appropriate.

The described and illustrated aspects are to be considered as illustrative and not restrictive in character, it being understood that only the preferred aspects have been shown and described and that all changes and modifications that come within the scope of the disclosure(s) as defined in the claims are desired to be protected. It should be understood that while the use of words such as "preferable", "preferably", "preferred" or "more preferred" in the description may suggest that a feature so described may be desirable, it may nevertheless not be necessary and aspects lacking such a feature may be contemplated as within the scope of the disclosure as defined in the appended claims. In relation to the claims, it is intended that when words such as "a," "an," or "at least one," are used to preface a feature there is no intention to limit the claim to only one such feature unless specifically stated to the contrary in the claim.

BRIEF DESCRIPTION OF THE DRAWINGS

The above mentioned and other features and objects of this invention, and the manner of attaining them, will become more apparent and the invention itself will be better understood by reference to the following description of aspects and embodiments of the invention taken in conjunction with the accompanying drawings, wherein:

FIGS. 2F-2H illustrate a scaffolding positioned in a mold cavity of a mold to form a scaffold reinforced prosthesis.

FIG. 44 illustrates a digital model of the interior of a patient's mouth.

FIG. 45A illustrates a picture of the interior of the patient's mouth.

FIG. 45B illustrates a digital model of the interior of the patient's mouth.

Figure 1A:
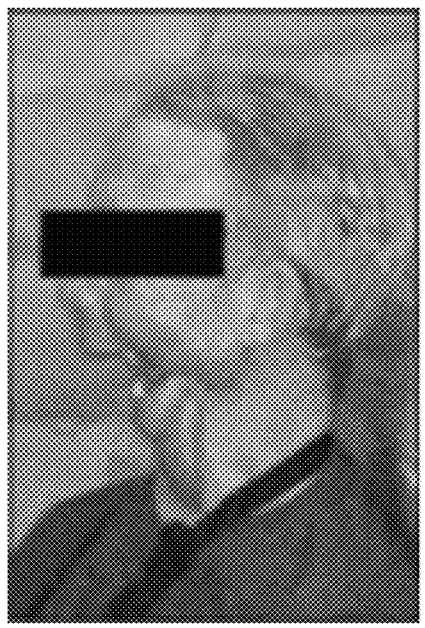
FIG. 1A shows a patient to be fitted with a mandibular prosthesis.

Corresponding reference characters indicate corresponding parts throughout the several views. Although the drawings represent aspects and embodiments of the present invention, the drawings are not necessarily to scale and certain features may be exaggerated in order to better illustrate and explain the present invention. The exemplification set out herein illustrate aspects and embodiments of the invention, in one form, and such exemplifications are not to be construed as limiting the scope of the invention in any manner.

DETAILED DESCRIPTION

The aspects disclosed below is not intended to be exhaustive or limit the invention to the precise form disclosed in the following detailed description. Rather, the aspects and embodiments are chosen and described so that others skilled in the art may utilize its teachings. Although illustrated below with respect the formation of a mandibular prosthesis, those of skill in the art will recognize that that the teachings may also be applied to the formation of other prostheses.

Figure 2A:
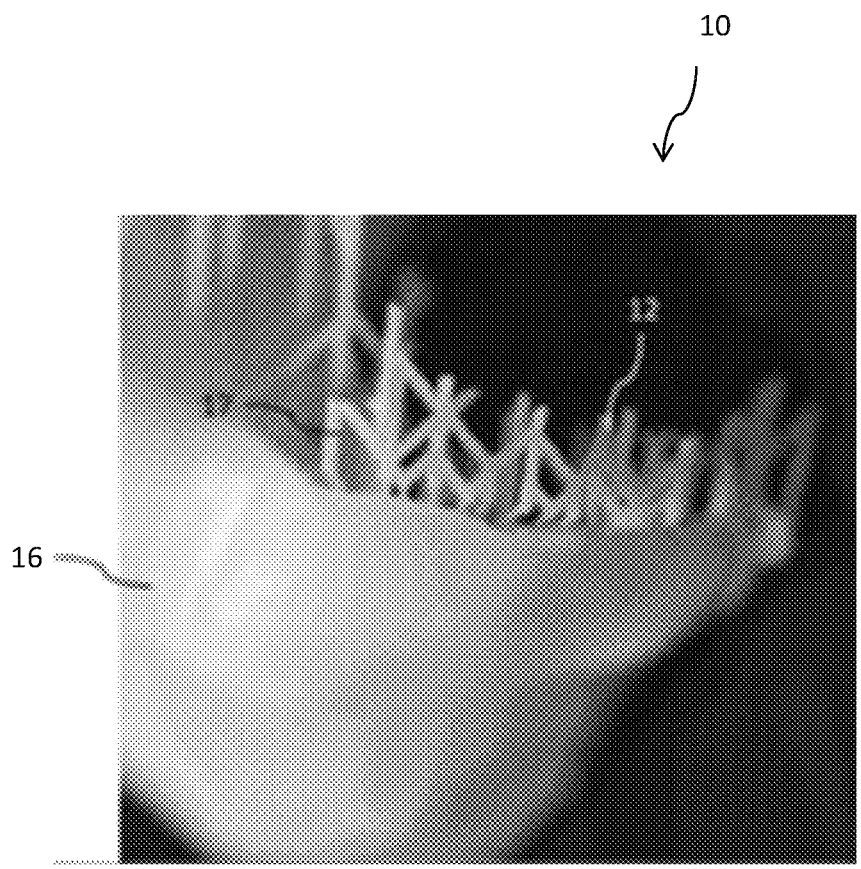
FIG. 2A illustrates a resin methacrylate 3D print of an exemplary prosthesis mold.

FIG. 2A illustrates an exemplary mold 16 for forming an exemplary prosthesis 10. Mold 16 is illustratively formed from a polymer using a rapid prototyping method, such as additive manufacturing, stereolithography (SLA), fused deposition modeling (FDM), selective laser sintering (SLS), selective laser melting (SLM), electronic beam melting (EBM), laminated object manufacturing (LOM), continuous liquid interface production (CLIP), and subtractive manufacturing methods such as CNC milling and melting. An exemplary polymer is a rigid methacrylate polymer. As shown in FIG. 2A, mold 16 illustratively includes multiple supports 17 for supporting mold 16 during the rapid prototyping process. In one aspect, supports 17 prevent mold 16 from falling, twisting, or wavering during the additive manufacturing process so the print does not fall, or waiver side to side during the printing process.

Figure 2B:
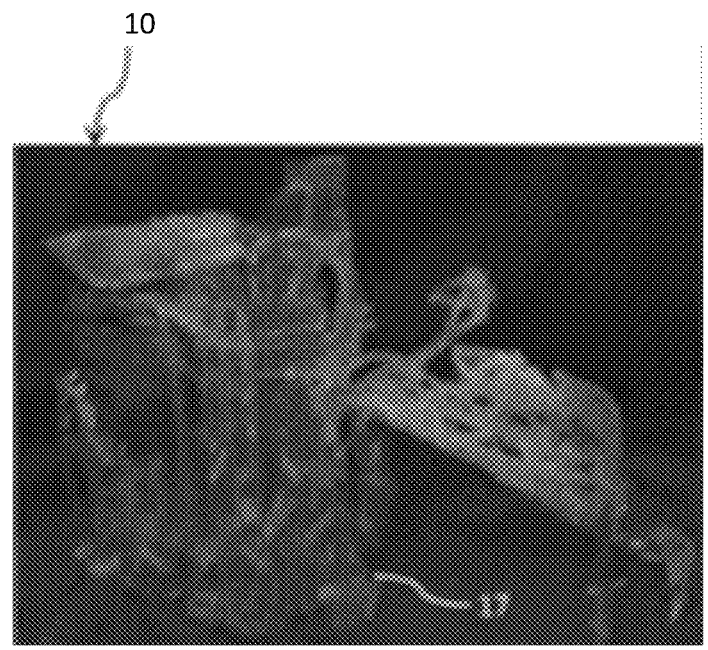
FIG. 2B illustrates a portion of an exemplary prosthesis formed from a flexible methacylate.

Referring next to FIG. 2B, another exemplary prosthesis 10 is illustrated. Prosthesis 10 is illustratively a mandibular prosthesis. Prosthesis 10 is illustratively supported using a plurality of supports 17 for supporting prosthesis 10 during the rapid prototyping process. As shown in FIG. 2B, at least a portion of prosthesis 10 is illustratively formed from a from a polymer using a rapid prototyping method, such as additive manufacturing, stereolithography (SLA), fused deposition modeling (FDM), selective laser sintering (SLS), selective laser melting (SLM), electronic beam melting (EBM), laminated object manufacturing (LOM), continuous liquid interface production (CLIP), and subtractive manufacturing methods such as CNC milling and melting. In one exemplary aspect, the polymer is a flexible methacrylate polymer.

Figure 2C:
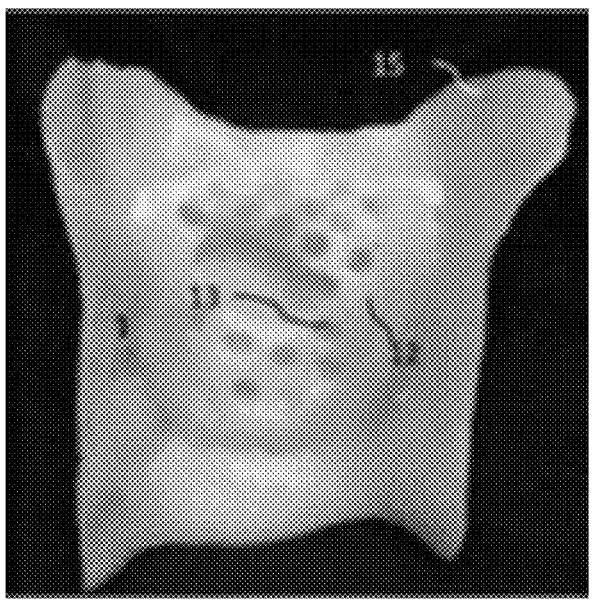
FIG. 2C illustrates a rear view of an exemplary prosthesis.
Figure 2D:
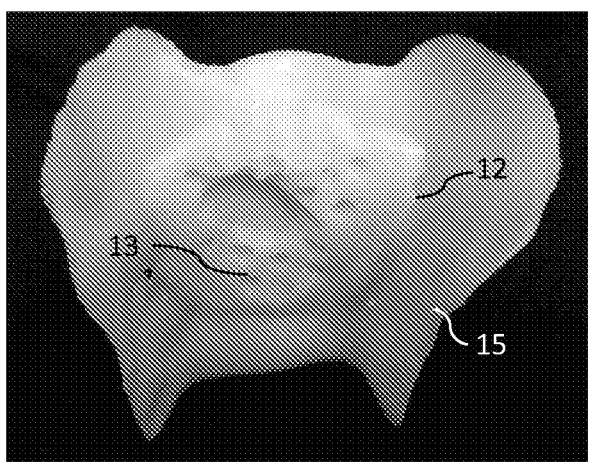
FIG. 2D illustrates a rear elevated view of the exemplary prosthesis of FIG. 2C.
Figure 2E:
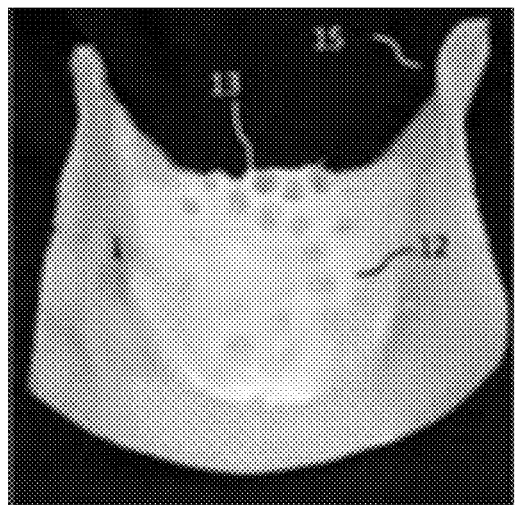
FIG. 2E illustrates a rear lowered view of the exemplary prosthesis of FIG. 2C.

Referring next to FIGS. 2C-2E, an exemplary portion of a prosthesis 10 formed using a 3D printer is illustrated. Prosthesis 10 illustratively includes an interior support structure, scaffolding 12, attached to a covering structure 15. In some aspects, prosthesis 10 further includes one or more coatings (not shown) covering at least a portion of scaffolding 12 and/or covering structure 15. In one exemplary aspect, the one or more coatings (not shown) fully cover the scaffolding 12 and covering structure 15, In one exemplary aspect, the mold 16, covering structure 15, and/or the scaffolding 12 is formed using a rapid prototyping method, such as additive manufacturing or subtractive manufacturing. The rapid prototyping method is illustratively carried out on a three-dimensional printer (3D printer) or computer numerical control (CNC) machine. 3D printers illustratively form a finished three-dimensional product using methods such as stereolithography (SLA), fused deposition modeling (FDM), selective laser sintering (SLS), selective laser melting (SLM), electronic beam melting (EBM), laminated object manufacturing (LOM), continuous liquid interface production (CLIP). CNC machines illustratively form a finished three-dimensional product using methods such as CNC milling and melting. In one exemplary aspect, the 3D printer uses as an additive manufacturing method, such as FDM, or CLIP to form the scaffolding 12 and/or the mold 16.

In one exemplary aspect, the scaffolding 12, covering structure 15, and the mold 16 are formed from the same polymer. In one exemplary aspect, at least two of the scaffolding 12, the covering structure 15, and the mold 16 are formed from different polymers. In one exemplary aspect, the scaffolding 12 is formed from multiple polymers. In one exemplary aspect, the covering structure 15 is formed from multiple polymers.

In one exemplary aspect, the scaffolding 12, covering structure 15, and/or mold 16 is formed of a suitable polymer material, such as polylactic acid (PLA), acrylonitrile butadiene styrene (ABS), and methacrylate polymers. Exemplary materials include PLA filament available from MakerBot Industries, LLC, Brooklyn, N.Y. and standard photopolymer resin and flexible photopolymer resin available from Formlabs Inc., Somerville, Mass. Other suitable organic and inorganic materials may also be used.

In one exemplary aspect, the scaffolding 12, covering structure 15, and/or mold 16 is formed from a polymer having an elongation at break as little as 25%, 40%, 45%, 50%, 75%, 80%, 85%, as great as 90%, 95% 100%, 150%, 200%, 220%, 225%, or within any range defined between any two of the foregoing values, such as 25% to 225%, 45% to 220%, or 80 to 95%, for example.

In one exemplary aspect, the scaffolding 12, covering structure 15, and/or mold 16 is formed from a polymer having a tensile strength as little as 0.5 MPa, 0.7 MPa, 0.8 MPa, 0.9 MPa, 1 MPa, as great as 2 MPa, 3 MPa, 4 MPa, 4.5 MPa, 5 MPa, 5.5 MPa, 6 MPa, 6.5 MPa, 7 MPa, 10 MPa, or within any range defined between any two of the foregoing values, such as 0.5 MPa to 10 MPa, 5 MPa to 7 MPa, or 0.8 MPa to 5 MPa, for example.

In one exemplary aspect, the scaffolding 12, covering structure 15, and/or mold 16 is formed from a polymer having a Shore A hardness as little as 20, 35, 30, 40, 50 as great as 60, 70, 80, 90, 95, 100, or within any range defined between any two of the foregoing values, such as 20 to 100, 25 to 80, or 80 to 90, for example.

Referring again to FIGS. 2C-2E, in one exemplary aspect, the scaffolding 12 is formed into a plurality of geometries 13 to provide support to scaffolding 12. Exemplary geometries include squares, triangles, trapezoids, rectangles, parallelograms, circles, diamonds, pentagons, hexagons, octagons, heptagons, ellipse, and three-dimensional shapes formed from the forgoing, including tetrahedrons, pyramids, cubes, cuboids, prisms, octahedrons, icosahedrons, dodecahedrons, cones, cylinders, and spheres. As shown in FIGS. 2C-2E, a cylindrical geometry 13 forms a plurality of voids in the scaffolding 12 to reduce the weight and increase the flexibility and breathability of prosthesis 10. In one exemplary aspect, the geometries are varied in shape, density, thickness, and/or size to provide various surface tensions, hardness, and/or flexibility for the prosthesis 10. In one exemplary aspect, the geometries are varied to provide different properties to correspond to and/or mimic human anatomical densities, form, function, and aesthetic on a corresponding patient, such as bone, muscle, and/or fat.

In one exemplary aspect, a single scaffolding 12 is provided to form the prosthesis 10. The scaffolding 12 may comprise a single type of geometry 13, or the scaffolding 12 may comprises multiple geometries 13 that vary in one or more of shape, density, thickness, and/or size.

In one exemplary aspect, supports 17 form at least a portion of the scaffolding 12.

In another exemplary aspect, multiple unconnected scaffoldings 12 are connected by the one or more coatings 14 to form the prosthesis 10. Each scaffolding 12 may comprise a single type of geometry 13, or each scaffolding 12 may comprise multiple geometries 13 that vary in one or more of shape, density, thickness, and/or size.

In one exemplary aspect, one or more coatings (not shown) at least partially covers the scaffolding 12. In one exemplary aspect, the coating is formed from a silicone material. Exemplary silicone materials include platinum silicone materials, which include a platinum-based cure system to polymerize a siloxane polymer. Suitable platinum silicone materials are available from Factor II, Inc., Lakeside, Ariz. Suitable coatings may further include at least one dispersion and/or matting agent.

In some exemplary aspects, multiple coatings are applied to scaffolding 12. The use of multiple layers of coatings may improve the finished aesthetic of the prosthesis. Additional layers may be used to form layers of skin, freckles, blemishes, etc. on the exterior of the prosthesis 10.

In some exemplary aspects, multiple coatings are applied to combine separate scaffoldings 12 into a single prosthesis 10. In another aspect, multiple coatings are used to combine scaffolding 12 that was formed separately from the skin-prosthesis 10 or mold 16.

In other exemplary aspects, only a single coating of silicone is used.

Without wishing to be held to any particular theory, it is believed that the inclusion of scaffolding, particularly in a prosthesis, such as prosthesis 10, allows for differences in the density and/or weight of the prosthetic. The use of various densities and/or weights provide tactile differences to the patient and others touching the prosthesis, such that portions correlating to bones feel like bones, portions correlating to skin feel like skin, and portions correlating to muscle feel like muscle.

Referring next to FIGS. 2F-2H, an exemplary mold 16 is illustrated. Mold 16 is illustratively a 2-piece mold comprised of mold halves 16A and 16B defining a mold cavity 18 there between. Other types of molds 16, such as molds comprising 3, 4, or more pieces, may also be used. In one illustrative aspect, mold 16 is formed together with scaffolding 12. In another illustrative aspect, mold 16 is formed separately from scaffolding 12, and scaffolding 12 is positioned inside mold cavity 18.

As shown in FIGS. 2F and 2G, the scaffolding may be attached to the mold 16 by one or more spines 19 to position the scaffolding 12 within the mold cavity 18. In one exemplary aspect, supports 17 form at least a portion of the spines 19. Silicone material is illustratively added to the mold cavity 18 to form the one or more coatings 14.

Figure 3A:
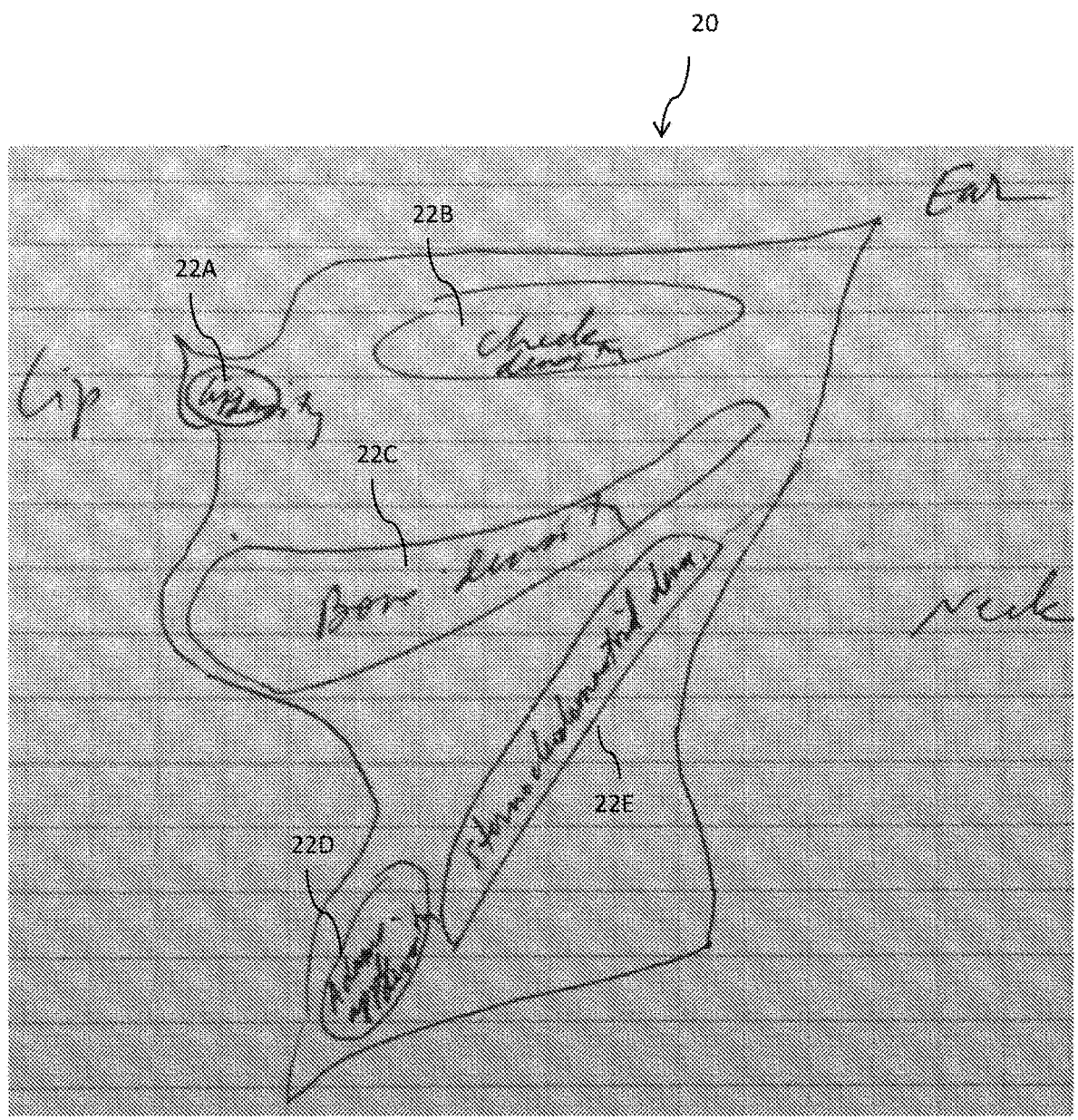
FIG. 3A illustrates an exemplary prosthesis including a multiple zones with different flexibility.

Referring next to FIG. 3A, another exemplary prosthesis 20 is illustrated. Prosthesis 20 is similar to prosthesis 10 and includes both a scaffolding 12 and one or more coatings 14. Prosthesis 20 includes multiple zones 22, including lip zone 22A, cheek zone 22B, bone zone 22C, circo-thyroid cartilage/thyroid cartilage/laryngeal prominence zone 22D, and sternocleidomastoid zone 22E. In one exemplary aspect, the scaffolding 12 is structured to provide a range of flexibilities for the zones 22. For example, in one exemplary aspect, lip zone 22A and cheek zone 22B may have a high flexibility and lower rigidity than bone zone 22C. In some aspects, providing multiple zones with different flexibilities or rigidities provide a more accurate replicate of the patient's natural anatomy with respect to form, function, and aesthetics.

In one exemplary aspect, the different flexibilities or rigidities of each zone 22 are provided based on the density or amount of material provided in each zone 22. In one exemplary aspect, the bone zone 22C may include a thicker scaffolding 12 than lip zone 22A or cheek zone 22B. In another exemplary aspect the scaffolding 12 in bone zone 22C may include smaller or less flexible repeating geometries, such as relatively smaller triangles or dodecahedrons, compared to lip zone 22A or cheek zone 22B, which may include larger or more flexible repeating geometries, such as relatively larger parallelograms or trapezoids.

In one example, the different flexibilities or rigidities of each zone 22 are provided based on the type of material used to form the scaffolding 12 in each zone 22. In one exemplary aspect, the scaffolding 12 in bone zone 22C may be formed of a less flexible and more rigid scaffolding than the scaffolding in lip zone 22A or cheek zone 22B.

Figure 3B:
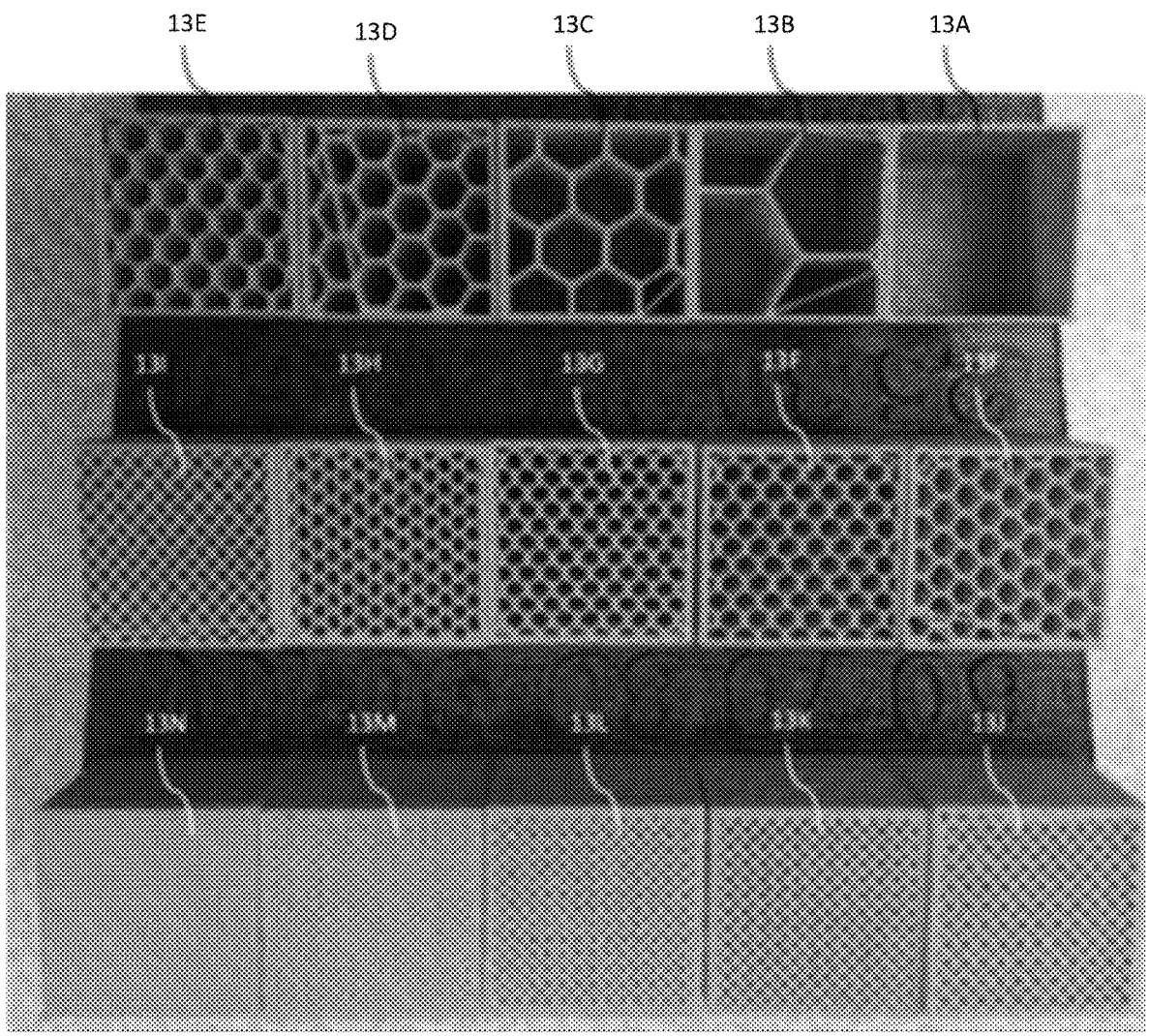
FIG. 3B illustrates a plurality of hexagonal geometries of various sizes.

Referring to FIG. 3B, a variety of geometries 13A-13N printed with a 3D printer are illustrated. Geometry 13A is a square prism with an open cavity, while geometry 13N is a solid square prism. Geometries 13B-13M include a plurality of hexagonal geometries 13 in the square prism of decreasing size. Geometry 13B includes the largest sized hexagonal geometry with the lowest amount material and of highest amount of void space, while geometry 13M includes the smallest sized hexagonal geometries with the highest amount of material and lowest amount of void space. Decreasing the size of the geometries 13, increasing the amount of material used, and decreasing the amount of void space illustratively reduces the flexibility and increases the rigidity and weight of the geometries 13.

Figure 4:
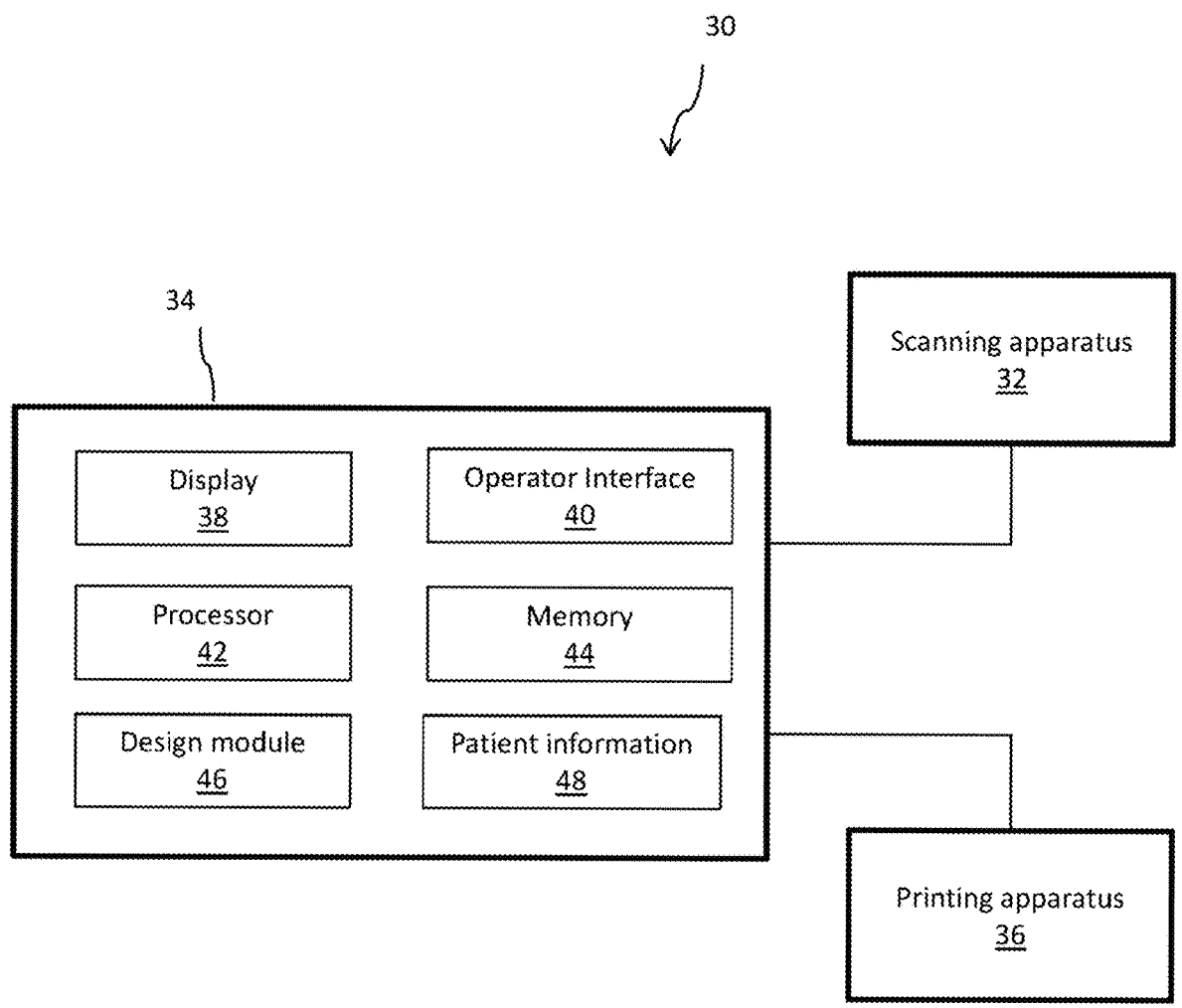
FIG. 4 illustrates an exemplary system for forming a prosthesis.

FIG. 4 illustrates an exemplary system 30 for forming a prosthesis. System 30 illustratively includes a scanning apparatus 32, a design apparatus 34, and a rapid prototyping device 36. Although illustrated as separate components in FIG. 3, scanning apparatus, design apparatus, and rapid prototyping device may be part of a single component, or combined into two or more separate components.

Scanning apparatus 32 illustratively includes one or more image capture devices for providing a topographic image of the patient. Illustrative scanning apparatus include photogrammetry systems. An exemplary photogrammetry system is the 3dMDface system, available from 3dMD LLC, Atlanta Ga. Other illustrative photogrammetry systems include no-contact laser scanning and digital cameras or cellular phones including a photogrammetry applications, such as 123D Catch, available from Autodesk Inc., San Rafael, Calif. In one exemplary aspect, by using a scanning apparatus, such as a photogrammetry system, forming a physical impression of the patient's face, such as shown in FIG. 1B, can be avoided. In addition, a photogrammetry system typically provides less soft-tissue distortion than forming an impression with polyvinyl siloxane and dental gypsum. Other illustrative scanning apparatus include computerized tomography (CT) scan machines and magnetic resonance imaging (MRI) machines.

As shown in FIG. 4, scanning apparatus 32 is operatively connected to design apparatus 34. Design apparatus 34 illustratively includes a display 38 such as a computer screen, television screen, or projector image, and operator interface 40 to accept inputs from an operator.

Design apparatus further includes one or more processors 42 having access to memory 44. Memory 44 is a non-transitory computer readable medium and may be a single storage device or may include multiple storage devices, located either locally with processor 42 or accessible across a network, or partially locally with processor 42 and partially accessible across a network. Computer-readable media may be any available media that may be accessed by processor 42 and includes both volatile and non-volatile media. Further, computer readable-media may be one or both of removable and non-removable media. By way of example, computer-readable media may include, but is not limited to, RAM, ROM, EEPROM, flash memory or other memory technology, CD-ROM, servers, Digital Versatile Disk (DVD) or other optical disk storage, magnetic cassettes, magnetic tape, magnetic disk storage or other magnetic storage devices, or any other medium which may be used to store the desired information and which may be accessed by processor 42. In one aspect, processor 42 communicates data, status information, or a combination thereof to a remote device for storage, analysis, or carrying out a predetermined command. In another aspect, memory 44 may further include operating system software. Memory 44 further includes communications software for communication with a network, such as a local area network, a public switched network, a CAN network, and any type of wired or wireless network. An exemplary public switched network is the Internet. Exemplary communications software includes e-mail software, SMS, Bluetooth communication software, radio frequency communication software, near field communication software and internet browser software. Other suitable software which permits processor 42 to communicate with other devices across a network may be used.

Figure 5A:
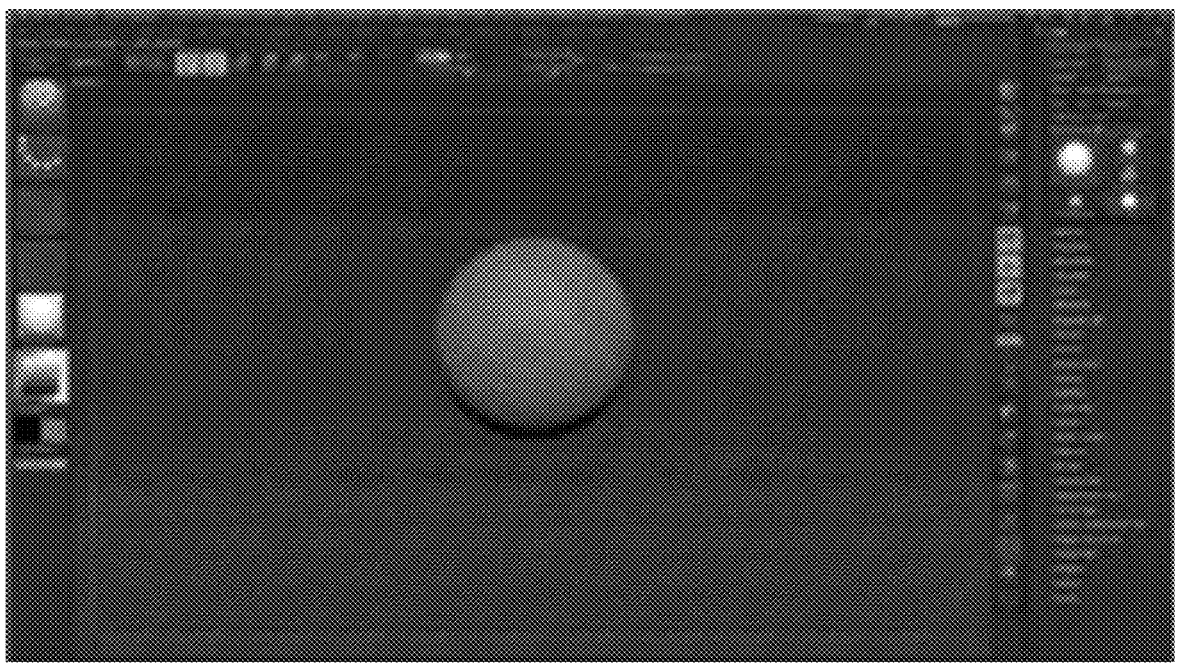
FIG. 5A illustrates a standard interface for electronically designing a digital model of the prosthesis using the ZBrush software program.
Figure 5B:
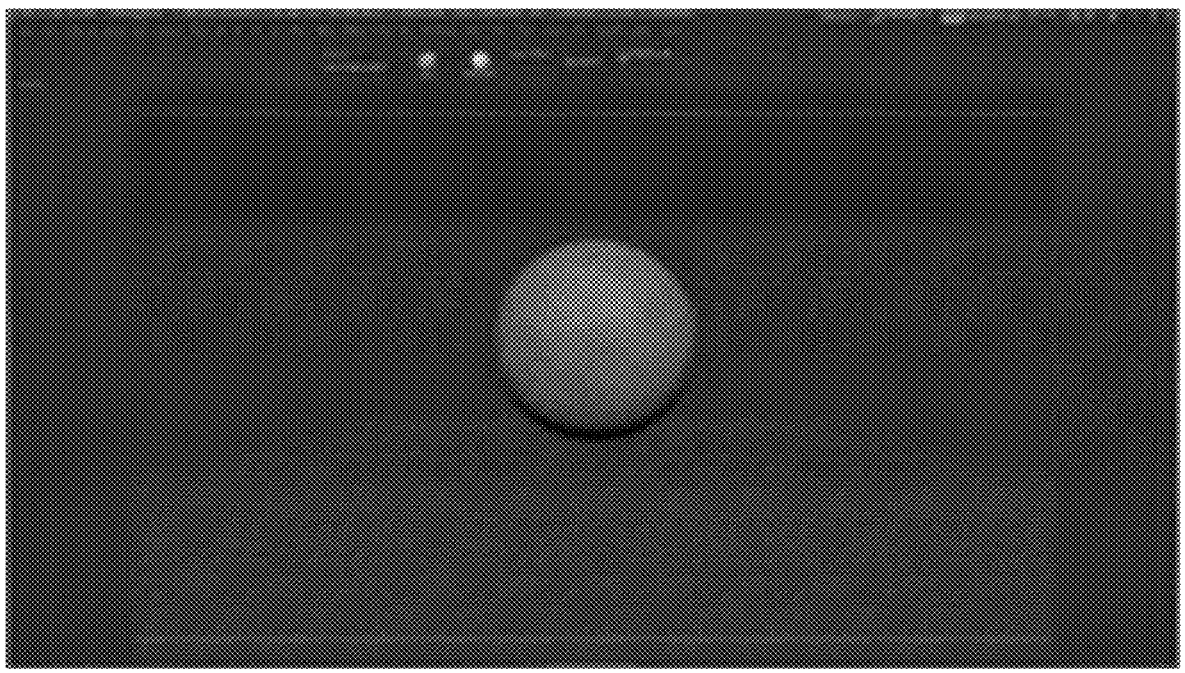
FIG. 5B illustrates a modified interface for importing a topographical image of a patient using the ZBrush software program from a photogrammetry scanner.
Figure 5C:
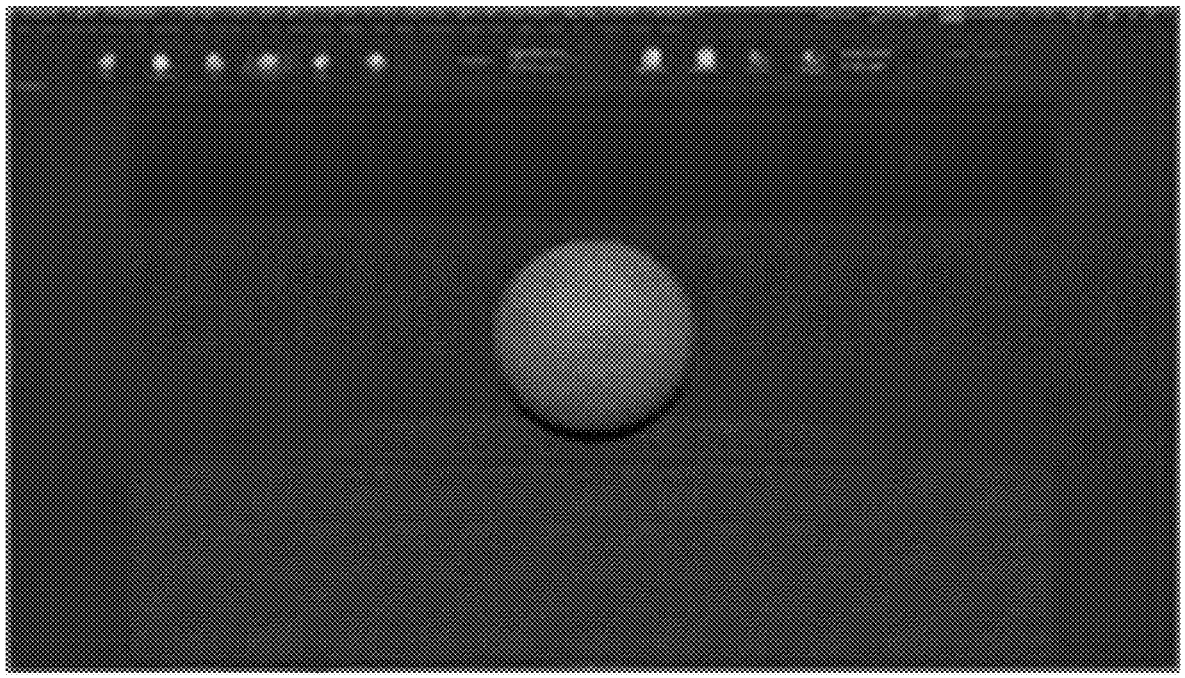
FIG. 5C illustrates a modified interface for designing and sculpting a digital model of the prosthesis using the ZBrush software program.
Figure 5D:
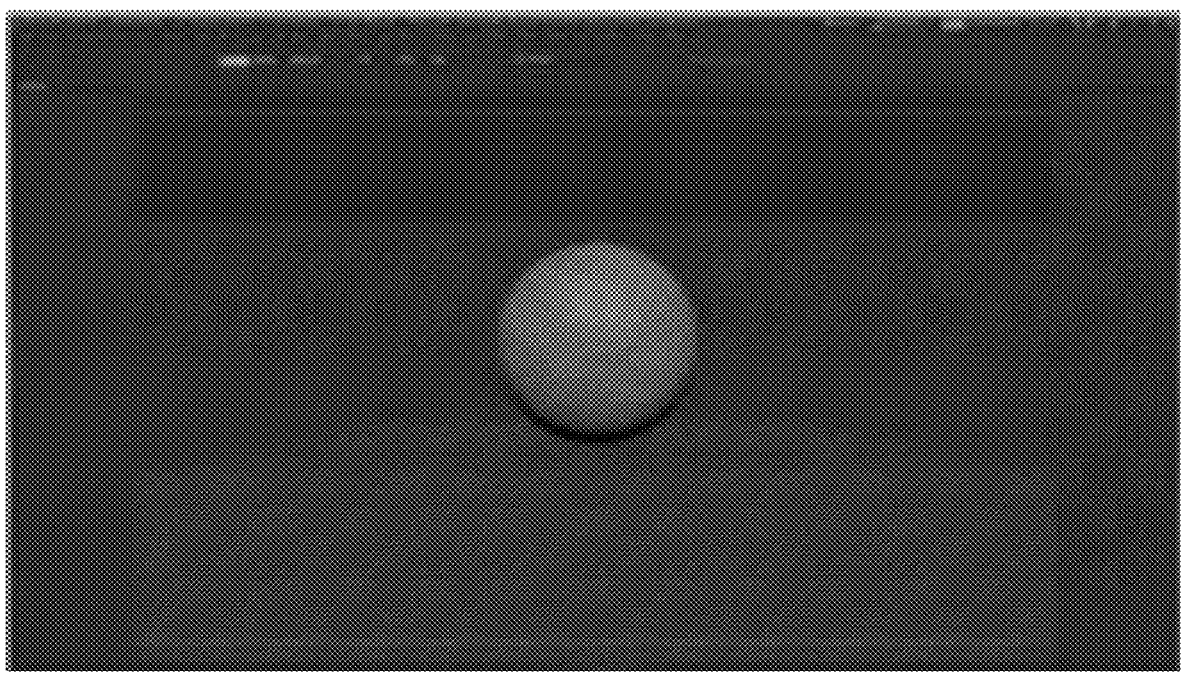
FIG. 5D illustrates a modified interface for exporting a digital model of the prosthesis using the ZBrush software program to a three-dimensional printer.

Design apparatus 34 illustratively includes design module 46. In one illustrative aspect, design module 46 comprises a graphic modeling software application. An exemplary graphic modeling software application is ZBrush, available from Pixologic Incorporated, Los Angeles Calif. FIG. 5A illustrates a standard interface for electronically designing a digital model of the prosthesis using the ZBrush software program. As can be seen in FIG. 5A, the interface includes various inputs for the user to select from and control, including various menus, buttons, sliders, brushers, and the like. In some exemplary aspects, a commercially available graphic modeling software application, such as ZBrush, may be modified or customized for use for specific steps within the design process. FIG. 5B illustrates a modified interface for importing a topographical image of a patient using the ZBrush software program from a photogrammetry scanner, in which many of the inputs shown in FIG. 5A have been removed. FIG. 5C illustrates a modified interface for designing and sculpting a digital model of the prosthesis using the ZBrush software program, in which many of the inputs shown in FIG. 5A have been removed. FIG. 5D illustrates a modified interface for exporting a digital model of the prosthesis using the ZBrush software program to a three-dimensional printer, in which many of the inputs shown in FIG. 5A have been removed.

Memory 44 may include patient information 48, including topographic images from scanning apparatus 32. Design module 46 illustratively has access to patient information 48 for use in designing the prosthesis model.

Design apparatus 34 is illustratively operably connected to a rapid prototyping device 36. Rapid prototyping device 36 is illustratively a 3D printer or CNC machine. Exemplary 3D printers include printers from MakerBot Industries, LLC, Brooklyn, N.Y. and Formlabs Inc., Somerville, Mass.

One of ordinary skill in the art will realize that the aspects provided can be implemented in hardware, software, firmware, and/or a combination thereof. Programming code according to the aspects can be implemented in any viable programming language such as C, C++, HTML, XTML, JAVA or any other viable high-level programming language, or a combination of a high-level programming language and a lower level programming language.

Figure 6:
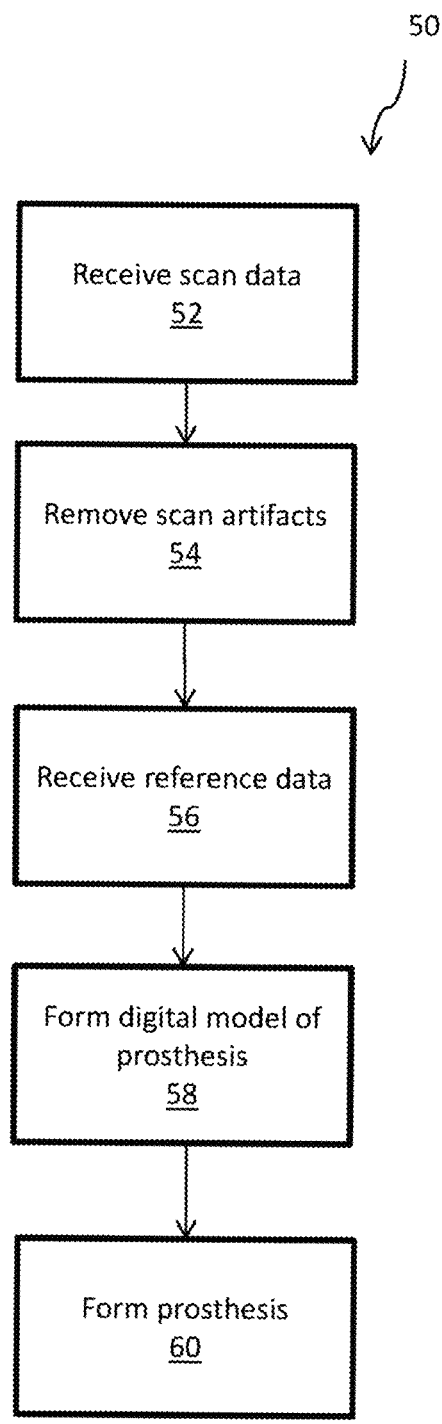
FIG. 6 illustrates an exemplary method of providing a prosthesis.

Referring next to FIG. 4 and FIG. 6, an illustrative method 50 of providing a prosthesis is illustrated. In one exemplary aspect, a graphic modeling software application, such as ZBrush, is utilized in method 50. In other aspects, a suitable computer aided design ("CAD") application such as Maya or Mudbox, available from Autodesk Inc., San Rafael, Calif., or Sculptris from Pixologic Incorporated, Los Angeles Calif. is utilized in method 50. In other aspects, the graphic modeling software application may include augmented reality or virtual reality functionality.

First, in block 52, scan data is received by the system. In one exemplary aspect, the system 30 receives scan data for a topographic image of the patient from scanning apparatus 32. In one aspect, the scanning apparatus includes a photogrammetry system for simultaneously capturing multiple images of the patient from multiple angles, such as the 3dMDface system. The system 30 may receive scan data from multiple scanning apparatus 32. For example, in one exemplary aspect, the system 30 receives a first set of scan data relating to internal components of the patient from a CT scan or MRI and a second set of scan data relating to surface and/or soft tissue components of the patient from a no-contact laser scanner or photogrammetry system such as the 3dMDface system.

Referring next to block 54, any artifacts present in the scan data are identified and removed. Exemplary scan artifacts include data errors and errors due to the presence of soft tissue. In some exemplary aspects, multiple sets of data are received by the system 30, and differences in the sets of data are utilized to identify artifacts. In some exemplary aspects, the topographical data is modeled in the graphic modeling software application, and artifacts are manually identified and removed using the application.

Referring next to block 56, reference data is received by system 30. The reference data may be stored in memory 44. Exemplary reference data include photographs of the patient, including pre-surgical or pre-trauma photographs of the patient. In one exemplary aspect, a model of at least a portion of the prosthesis, such as a scaffold, may be received by the system 30 from a CAD application such as Maya from Autodesk, and the design module 46 is used to form a digital model of the prosthesis including the scaffold. In one exemplary aspect, the reference data includes information relating to a previously modeled prosthesis. In block 58, the operator interface 40 and design module 46 are utilized to form a digital model of the prosthesis. In one exemplary aspect, the prosthesis is modeled using the pre-surgical or pre-trauma photographs to provide a similar appearance.

Figure 7:
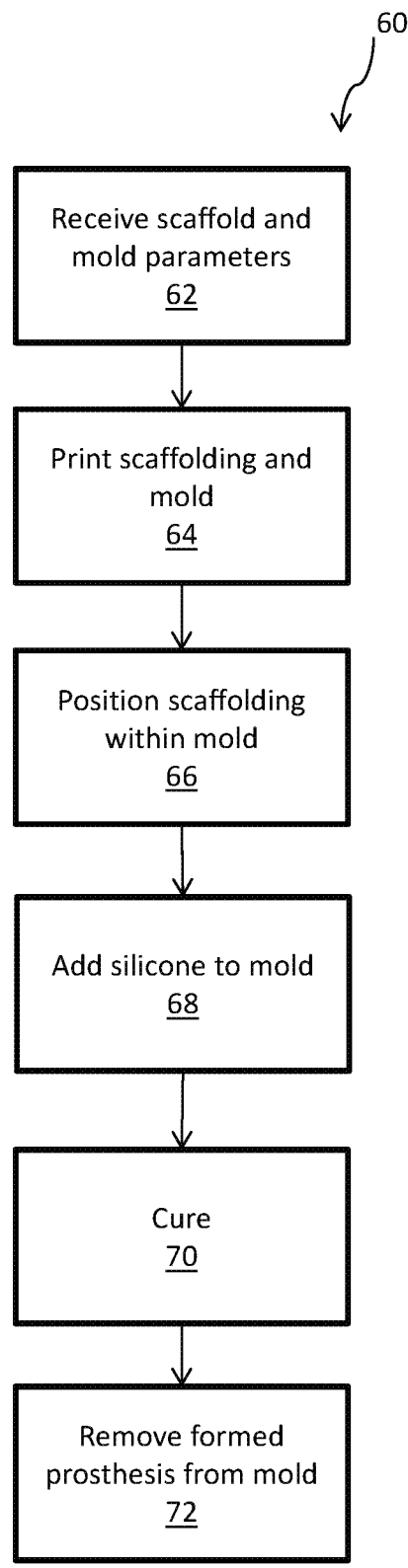
FIG. 7 illustrates an exemplary method of forming a prosthesis.

Referring next to block 60, the prosthesis is then formed. An exemplary method of forming the prosthesis in block 60 is illustrated in FIG. 7. Referring to FIGS. 4 and 7, in block 62, the rapid prototyping device 36, such as a 3D printer, receives information from the system 30 relating to the printing of the scaffolding 12 and/or the mold 16. In block 64, the scaffolding 12 and/or mold 16 are separately printed using the rapid prototyping device. In one exemplary aspect, the scaffold material is cured using UV light as part of the printing process, such as using continuous liquid interface production (CLIP) 3D printing methods.

If the scaffolding 14 and mold 16 are formed separately, in block 66, the scaffolding is positioned in the mold 16 (FIG. 2F).

In block 68, silicone is added to the mold cavity 18 to form the coating 14 at least partially covering the scaffolding 12. In block 70, the silicone coating 14 is cured. Exemplary methods of curing include heat curing to activate a platinum catalyst in the silicone material. In block 72, the cured prosthesis is removed from the mold 16.

In other aspects (not shown), the coating is allowed to partially harden in the mold, followed by removal of the formed prosthesis 10 from the mold, and curing of the removed prosthesis 10.

If additional coatings are desired, the scaffolding 12 and coating 14 removed from mold 16 in block 72 may be placed into a mold having a larger mold cavity. Additional silicone or other material may be added to the mold cavity, and blocks 68-72 repeated until the desired number of coatings 14 have been applied to form the prosthesis 10.

In some exemplary aspects, the method of forming the prosthesis may be dramatically reduced compared to traditional methods. In some exemplary aspects, method 50 may be performed in as little as 48 hours, 36 hours, 24 hours, 12 hours, or less. In some exemplary aspects, the method of forming a prosthesis 60 may be performed in as little as 24 hours, 12 hours, 4 hours, 1 hour, 30 minutes, 15 minutes, or less.

EXAMPLES

Figure 1B:
FIG. 1B shows an impression of the patient's face being taken.
Figure 1C:
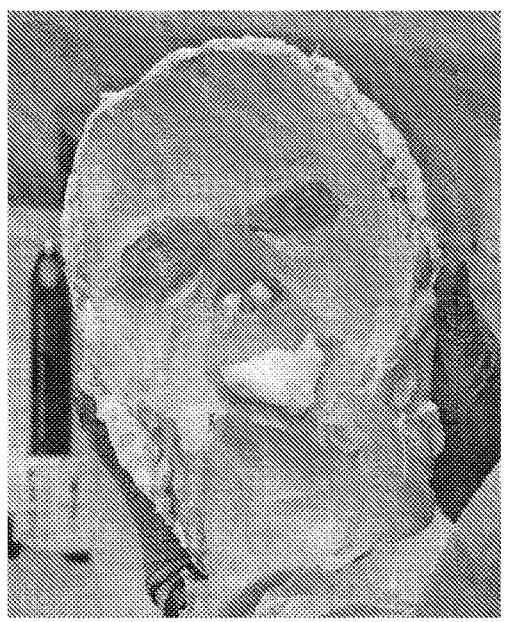
FIG. 1C shown the formed impression from FIG. 1B.
Figure 1D:
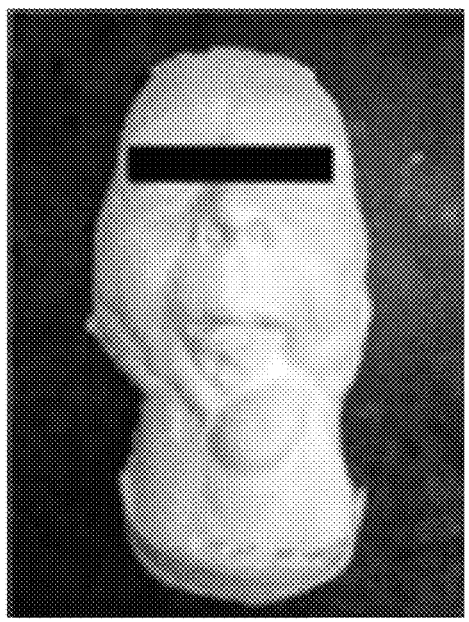
FIG. 1D shows a cast made from the formed impression of FIG. 1C.
Figure 1E:
FIG. 1E shows sculpting clay used to form a model of a mandibular prosthesis.
Figure 1F:
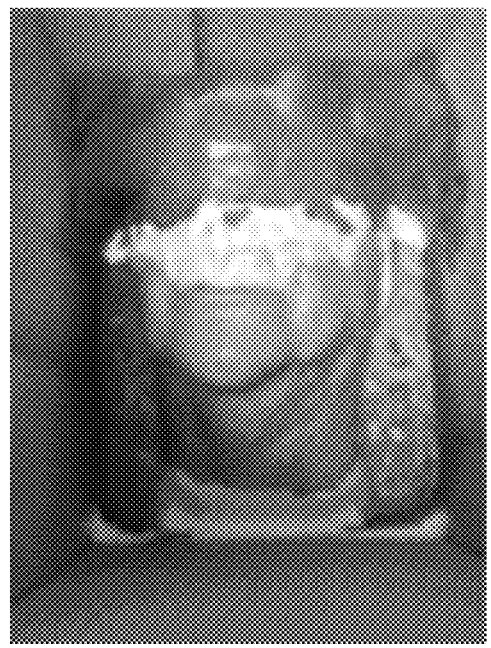
FIGS. 1F-1I show the molding of the mandibular prosthesis based on the clay model.
Figure 1G:
Figure 1H:
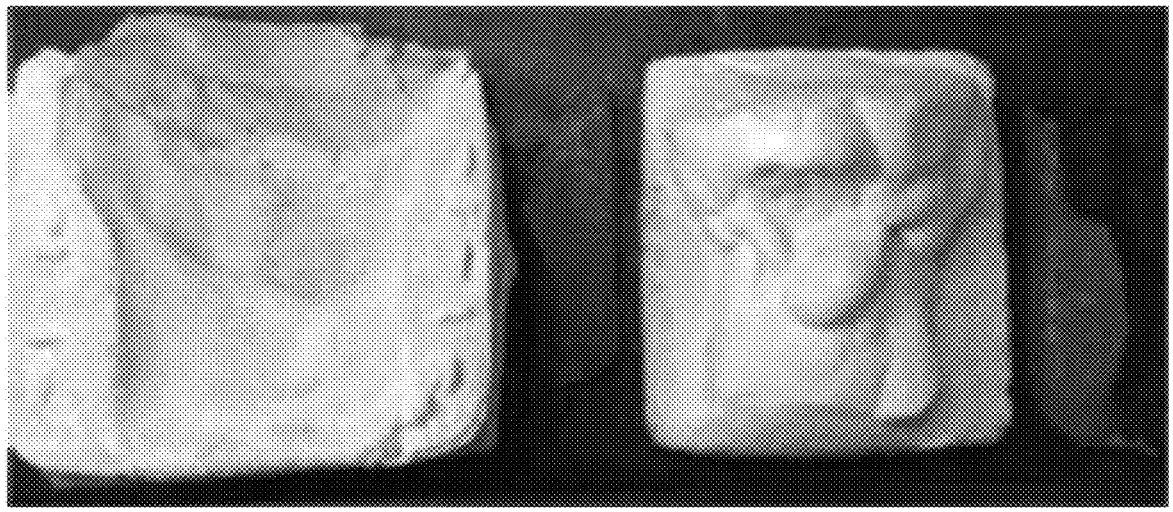
Figure 1I:
Figure 1J:
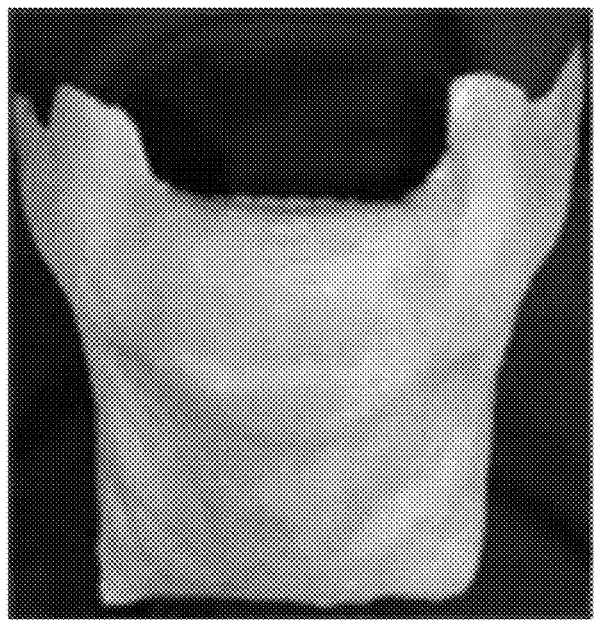
FIG. 1J shows a finished prosthesis formed from a typical impression and design process.
Figure 8A:
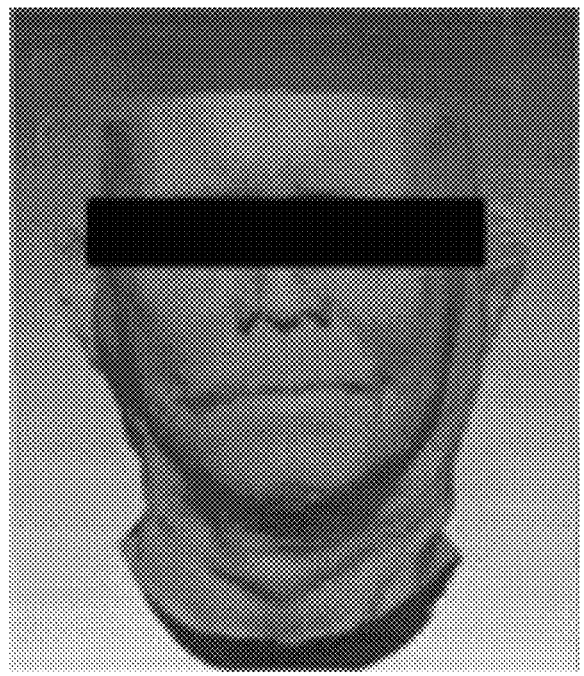
FIG. 8A illustrates image of the patient of FIG. 1A wearing a traditionally molded prosthesis captured using a photogrammetry scanner.
Figure 8B:
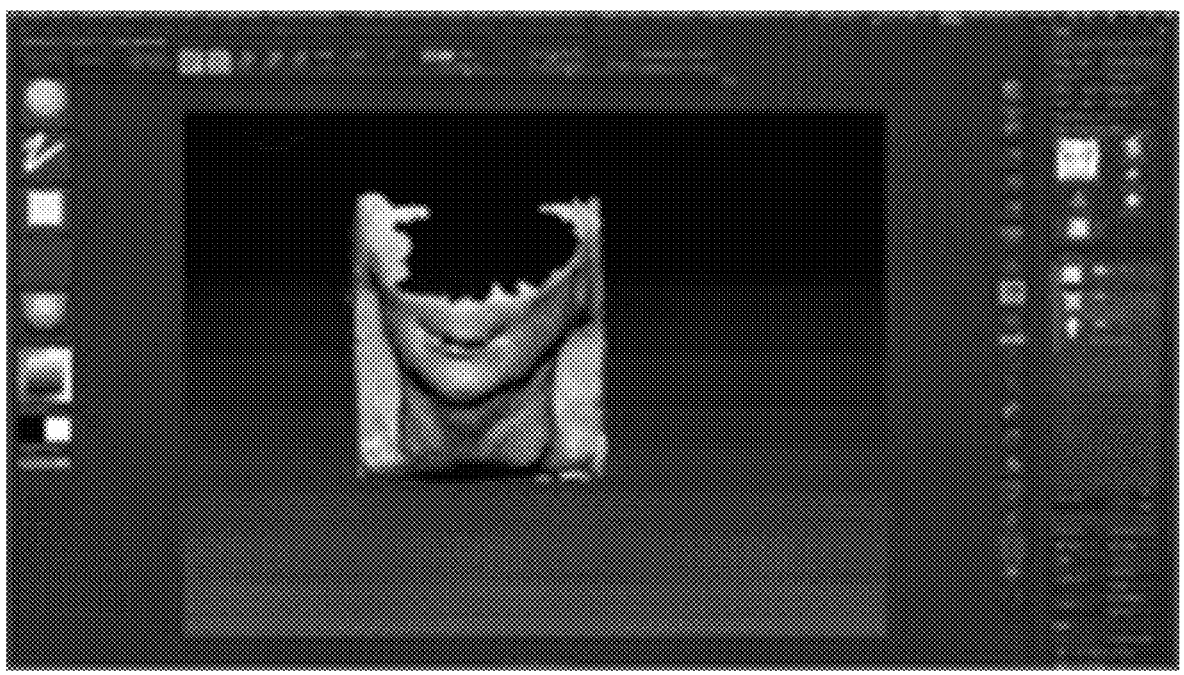
FIG. 8B illustrates a view of a portion of the scan data from FIG. 8A showing a front view of the patient using the ZBrush software program.
Figure 8C:
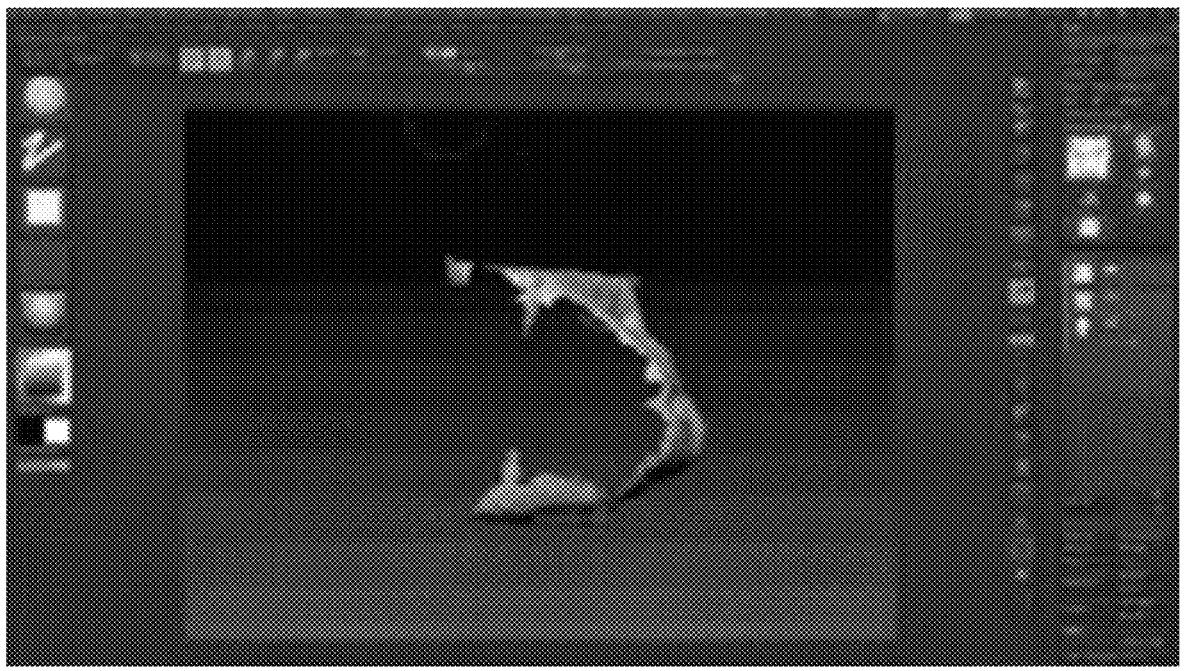
FIG. 8C illustrates another view of the portion of the scan data from FIG. 8B showing an overhead view of the topographical data of the patient using the ZBrush software program.

A maxillofacial prosthesis was designed and formed using method 50 (FIG. 6) for the patient pictured in FIG. 1A using a 3dMDface stereophotogrammetry system as the scanning apparatus 32 and a 3D printer as the rapid prototyping device 36. FIG. 8A illustrates an image of the patient of FIG. 1A wearing a traditionally molded prosthesis captured using a photogrammetry scanner, a 3dMDface stereophotogrammetry system. FIG. 8A was used as a reference image in crafting the new prosthesis 10. FIG. 8B illustrates a view of a portion of the scan data from FIG. 8A showing a front view of the patient using the ZBrush software program. FIG. 8C illustrates another view of the portion of the scan data from FIG. 8B showing an overhead view of the topographical data of the patient using the ZBrush software program.

Figure 8D:
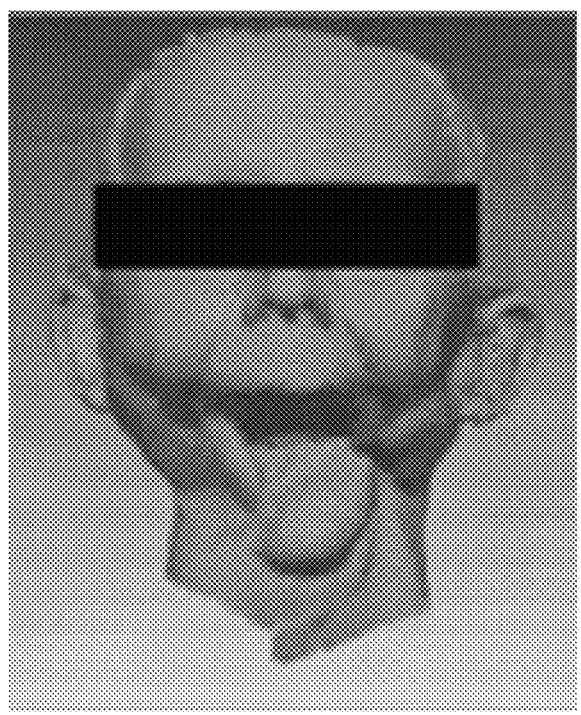
FIG. 8D illustrates an image of the patient of FIG. 1A without a prosthesis captured using a photogrammetry scanner.
Figure 8E:
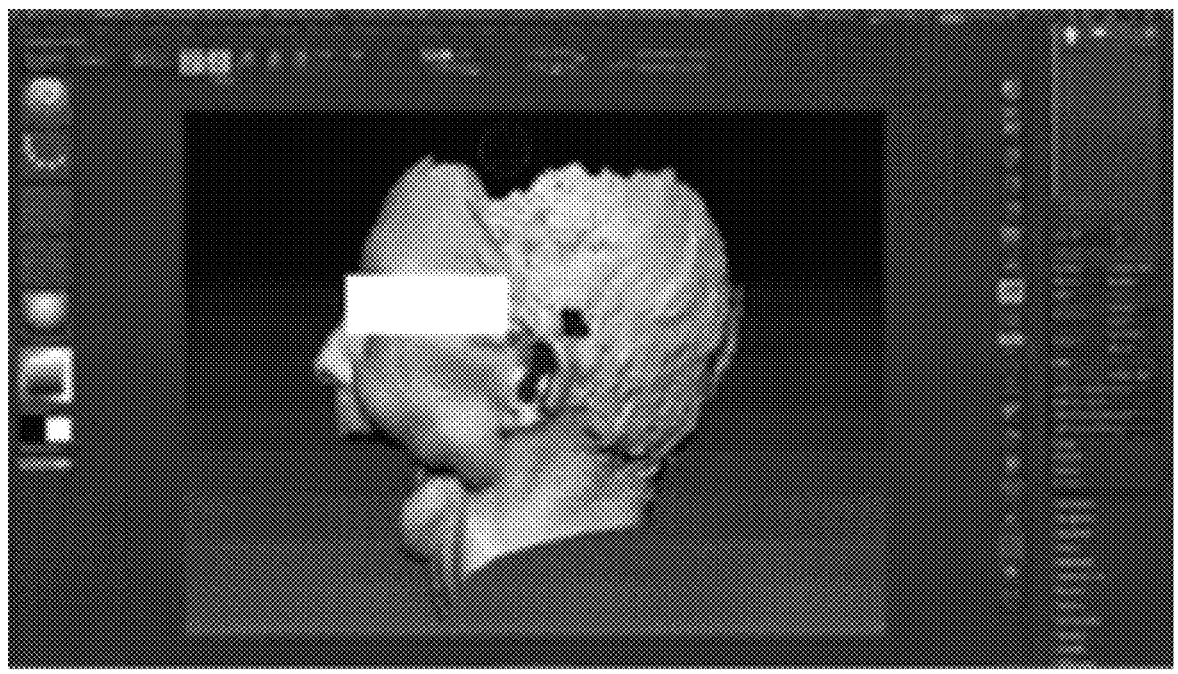
FIG. 8E illustrates the image of FIG. 8D showing a side view of the patient using the ZBrush software program prior to any modifications of the scan data.

FIG. 8D illustrates an image of the patient of FIG. 1A without the traditionally molded prosthesis shown in FIG. 8A. FIG. 8D was also captured using the 3dMDface stereophotogrammetry scanner. FIG. 8E illustrates the image of FIG. 8D showing a side view of the patient using the ZBrush software program prior to any modifications of the scan data. As can be seen in FIG. 8E, the image includes multiple artifacts to the mesh surface to be identified and removed.

Figure 8F:
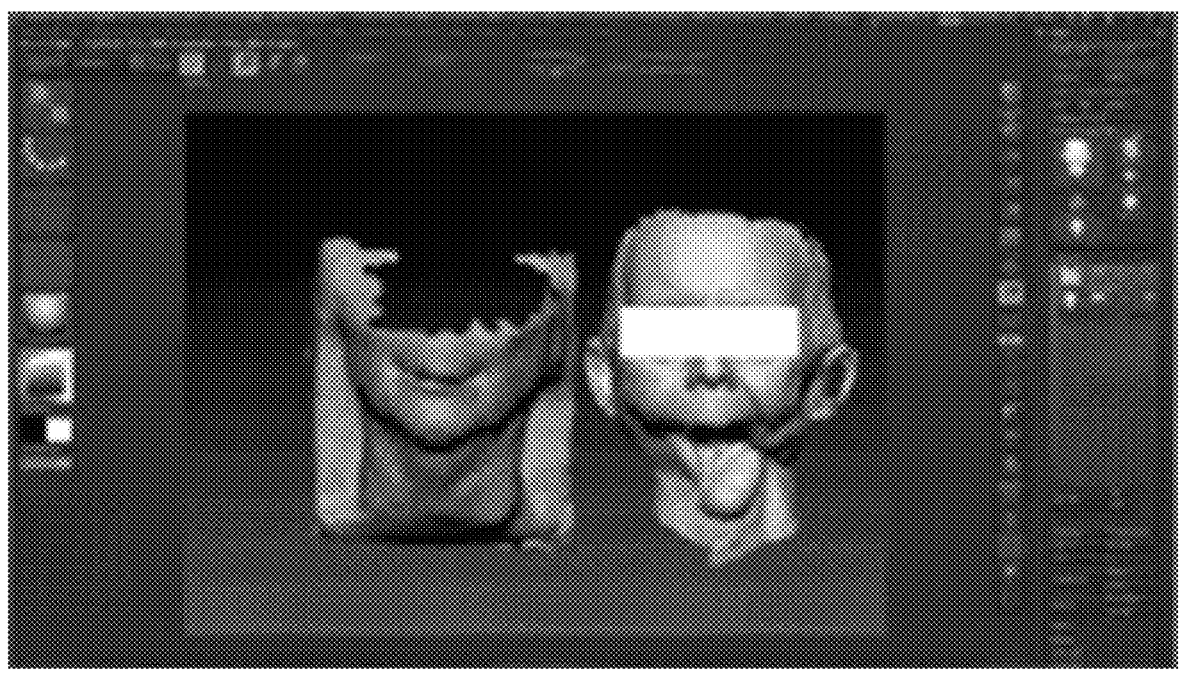
FIG. 8F illustrates the image of FIG. 8B of the patient wearing a traditionally molded prosthesis positioned next to the image of FIG. 8D of the patient without a prosthesis.

The data artifacts in FIG. 8E were manually identified and removed. FIG. 8F shows a comparison of the reference image shown in FIG. 8B of the patient wearing the traditionally molded prosthesis is shown next to the image of FIG. 8D showing the patient without the prosthesis. A model of the prosthesis was digitally sculpted in the ZBrush software program to fit the patient as shown in FIGS. 8D and 8F. The reference image of the patient, as shown in FIGS. 8A and 8F, was used in designing the front aesthetics of the prosthesis. The prosthesis was sculpted to closely match the reference image of the patient.

Figure 8G:
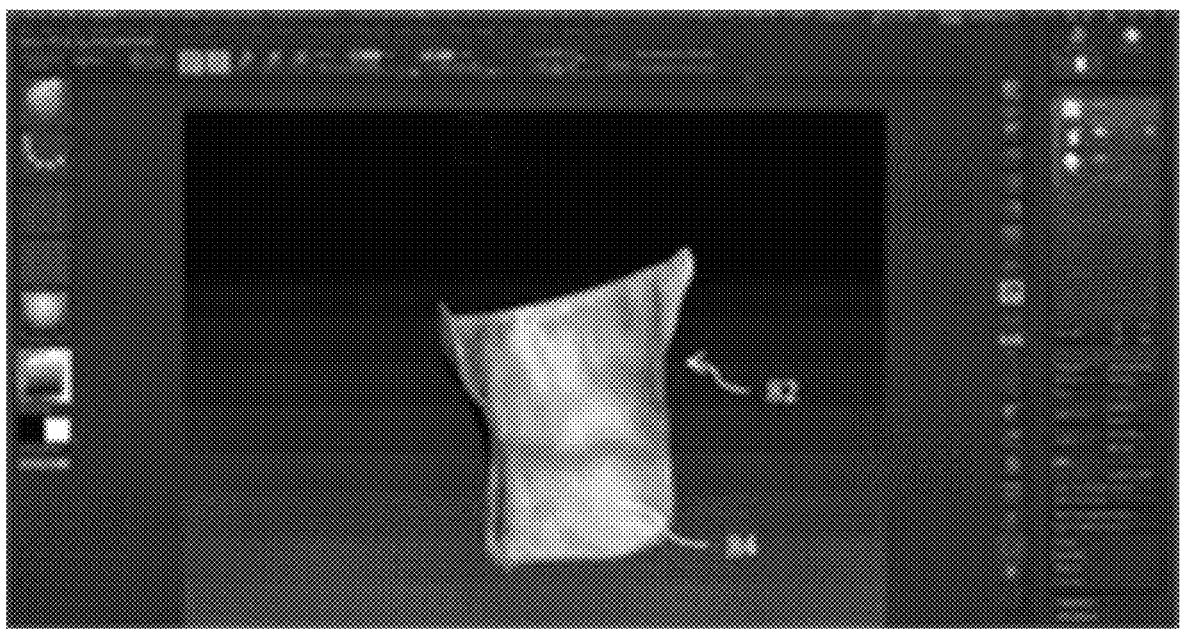
FIG. 8G illustrates an image of a back side of model of a prosthesis designed using the ZBrush software program.

A back view of the digital model of the prosthesis 82 is shown in FIG. 8G. The back surface 84 of the prosthesis 82 is oriented towards the patient's injuries.

Figure 8H:
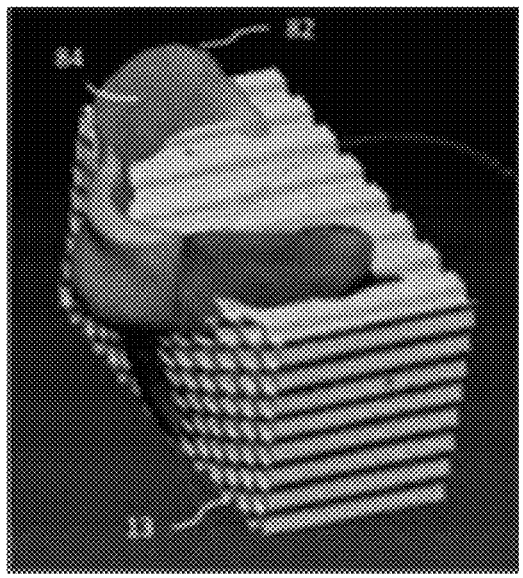
FIG. 8H illustrates an image of the scaffold geometries being applied to the digital model of the prosthesis.

Referring next to FIG. 8H, a scaffolding pattern of repeating geometries 13 is applied to the digital model of the prosthesis 82 shown in FIG. 8G. The repeating geometries 13 are illustratively a hexagonal prism structure, although other shapes may also be used, as discussed above. The geometries illustratively provide a relatively lightweight structure to the finished prosthesis 10.

Figure 8I:
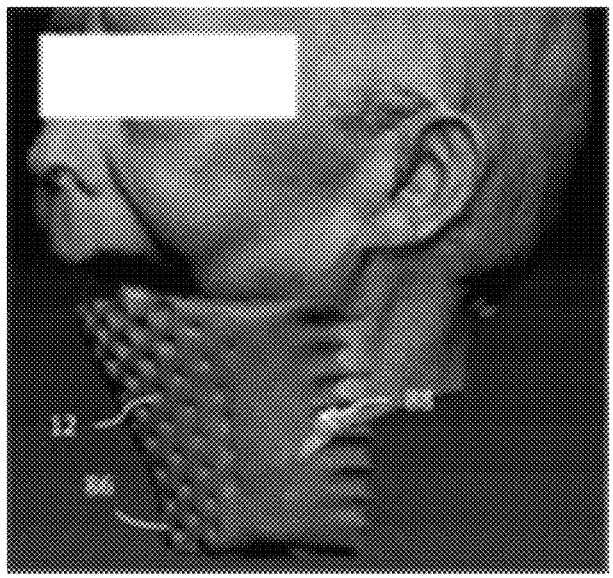
FIG. 8I illustrates an image of the scaffold geometries being applied to the digital model of the prosthesis.

As shown in FIG. 8I, the front surface 86 of the scaffolding 12 is then trimmed to fit into the back surface 84 of the prosthesis 82 (FIG. 8G), while the back surface 88 of the scaffolding 12 is trimmed to match the patient's injuries.

Figure 8J:
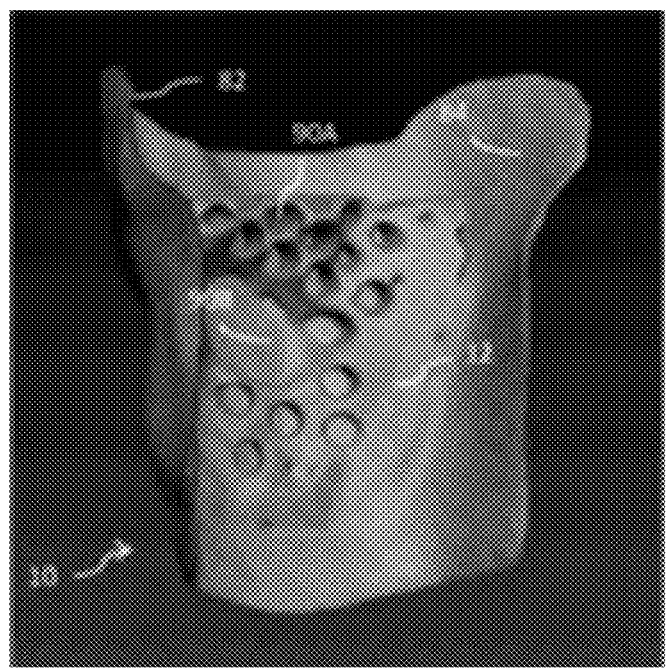
FIG. 8J illustrates a back view of the digital model of the prosthesis showing the incorporation of the scaffold geometry into the prosthesis.

An illustrative view of the prosthesis 10 is illustrated in FIG. 8J (silicone coating omitted). The prosthesis 10 includes the prosthesis 82 and the scaffolding 12. Scaffolding 12 illustratively includes voids 90A due to the geometries and voids 90B to accommodate the patient's injuries and facial features. The use of the scaffolding 12 allows for a relatively lightweight, flexible, and breathable prosthesis for the patient.

Figure 8K:
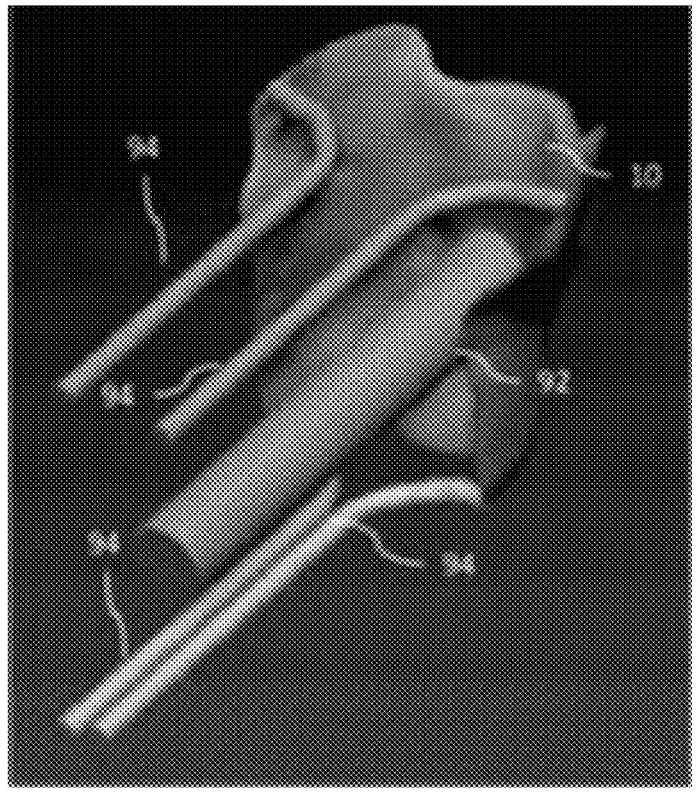
FIG. 8K illustrates an image of the digital model of the prosthesis during design of the prosthesis and mold.
Figure 8L:
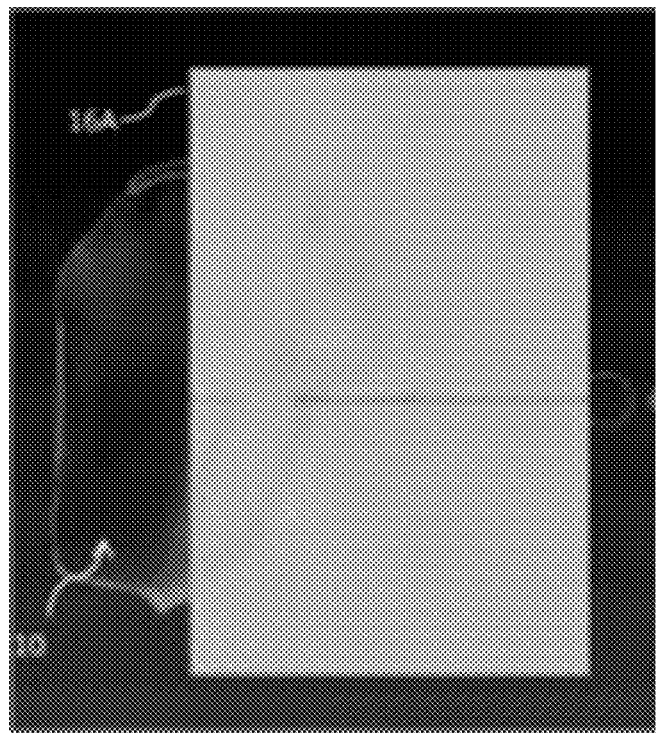
FIG. 8L illustrates an image of the digital model of the prosthesis and mold during design of the prosthesis and mold.

Referring next to FIGS. 8K and 8L, a digital model of the mold 16 is formed. FIG. 8K shows the addition of silicone investment pathway 92 and airway vents 94 in the mold. As shown in FIG. 8K, the thick straight cylinder of the silicone investment pathway 92 is a positive of what will eventually be a negative space once it is enclosed in the 2-piece mold 16 (see FIGS. 2F-2H). The curved thin cylinders of airway vents 94 enable complete silicone penetration into the mold 16. FIG. 8L illustrates a rough draft of one piece 16A (illustratively a front plate) of mold 16. Mold 16 is typically formed from a first piece 16A (front plate) and a second piece 16B (back plate) (not shown). The outline of prosthesis 10 is shown in shadow. The silicone investment pathway 92 and airway vents 94 are incorporated into the second piece 16B (back plate) behind the prosthesis 10.

Figure 8M:
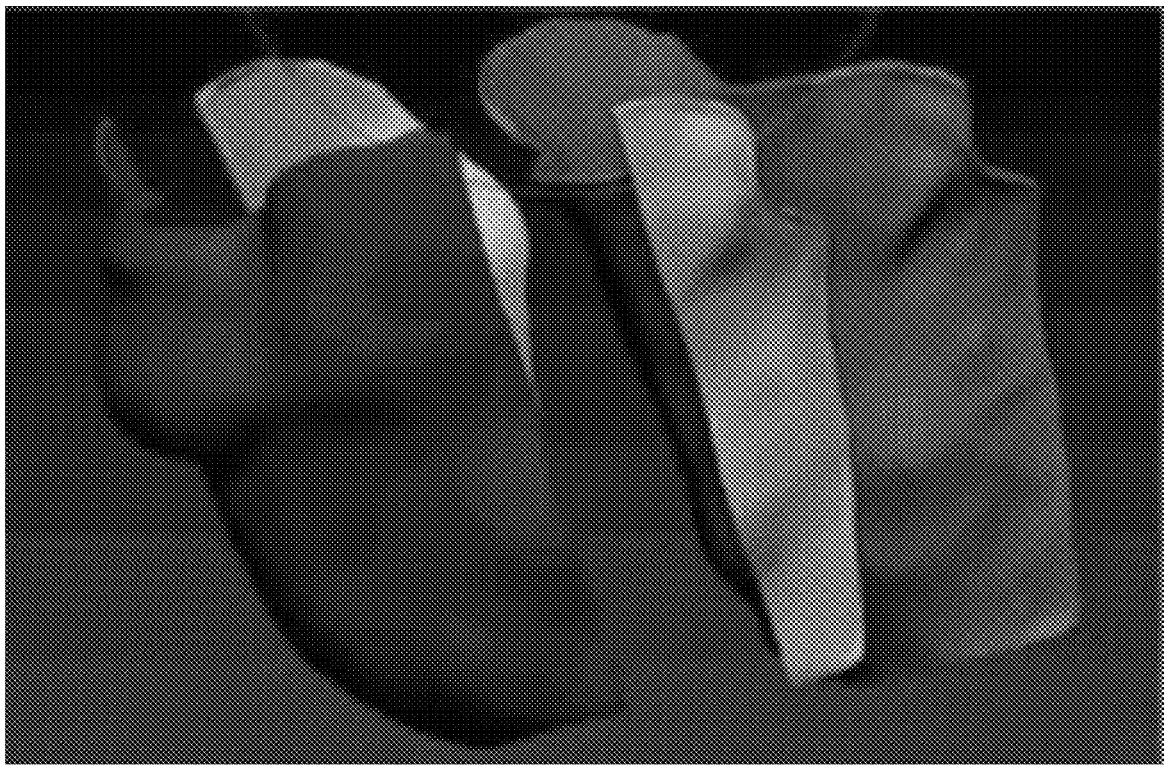
FIG. 8M illustrates a digital model of 4-piece compression type mold for forming the prosthesis shown in FIG. 8G.

FIG. 8M illustrates a digital model of an alternative exemplary mold 16'. Mold 16' is illustratively a four-piece compression type mold for forming prosthesis 10 as shown in Figure FIG. 8M illustrates a digital model of 4-piece compression type mold for forming the portion of prosthesis 82 shown in FIG. 8G or prosthesis 10 shown in FIG. 8J.

Figure 9A:
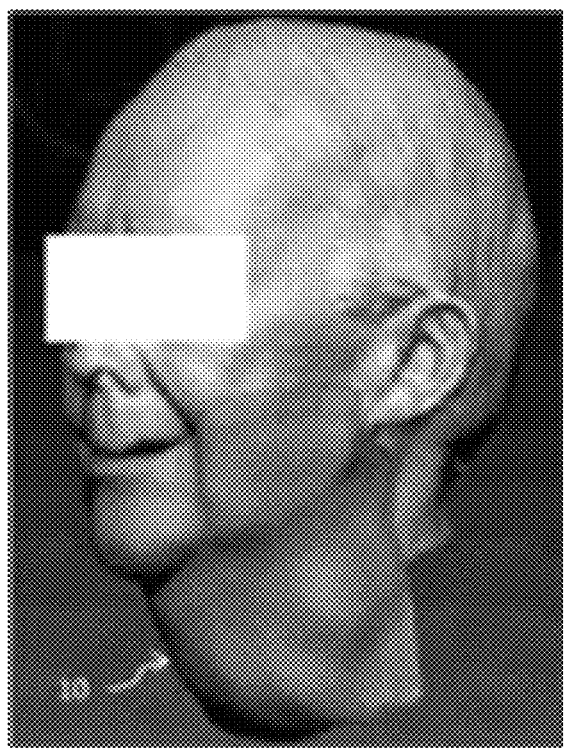
FIGS. 9A-9D illustrate the digital model of the exemplary prosthesis with the digital image shown in FIG. 8D.
Figure 9B:
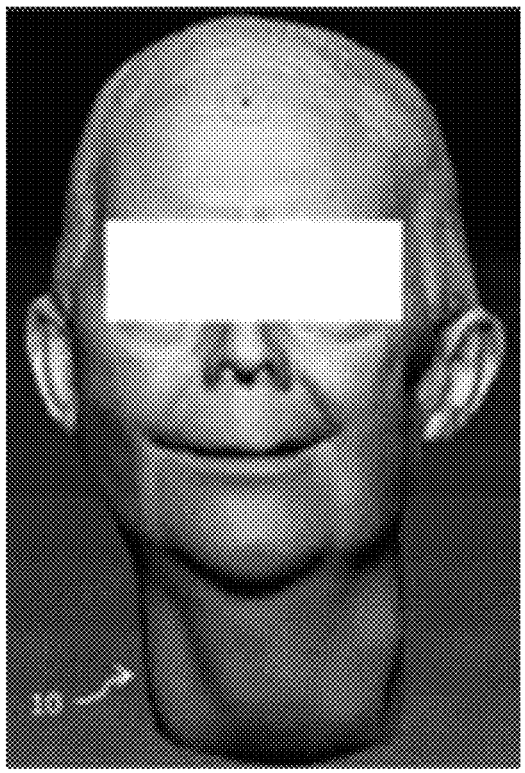
Figure 9C:
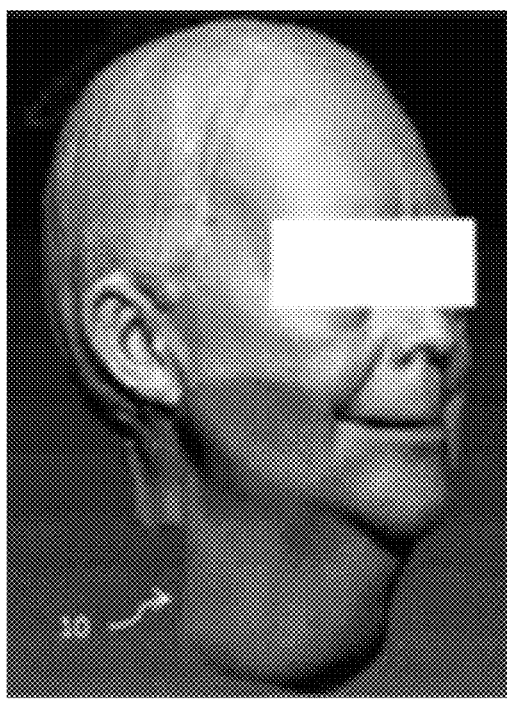
Figure 9D:

FIGS. 9A-9D illustrate the image of the patient in FIG. 8D with the data artifacts removed and human features sculpted in. FIGS. 9A-9D further illustrate the finalized mandibular prosthesis 10 shown in FIG. 8J. The image of the patient in FIG. 9D is shown as transparent.

Figure 10:
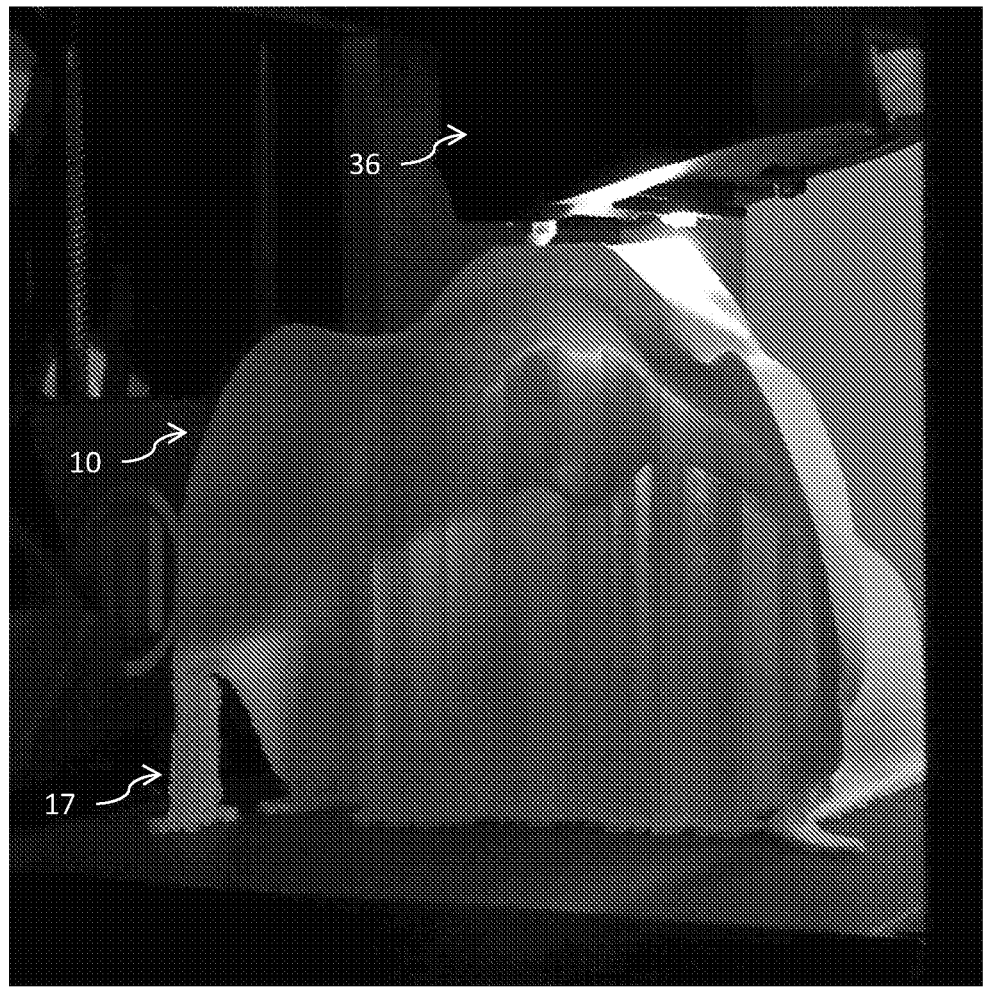
FIG. 10 illustrates the 3D printing of an exemplary prosthesis with polylactic acid.
Figure 11A:
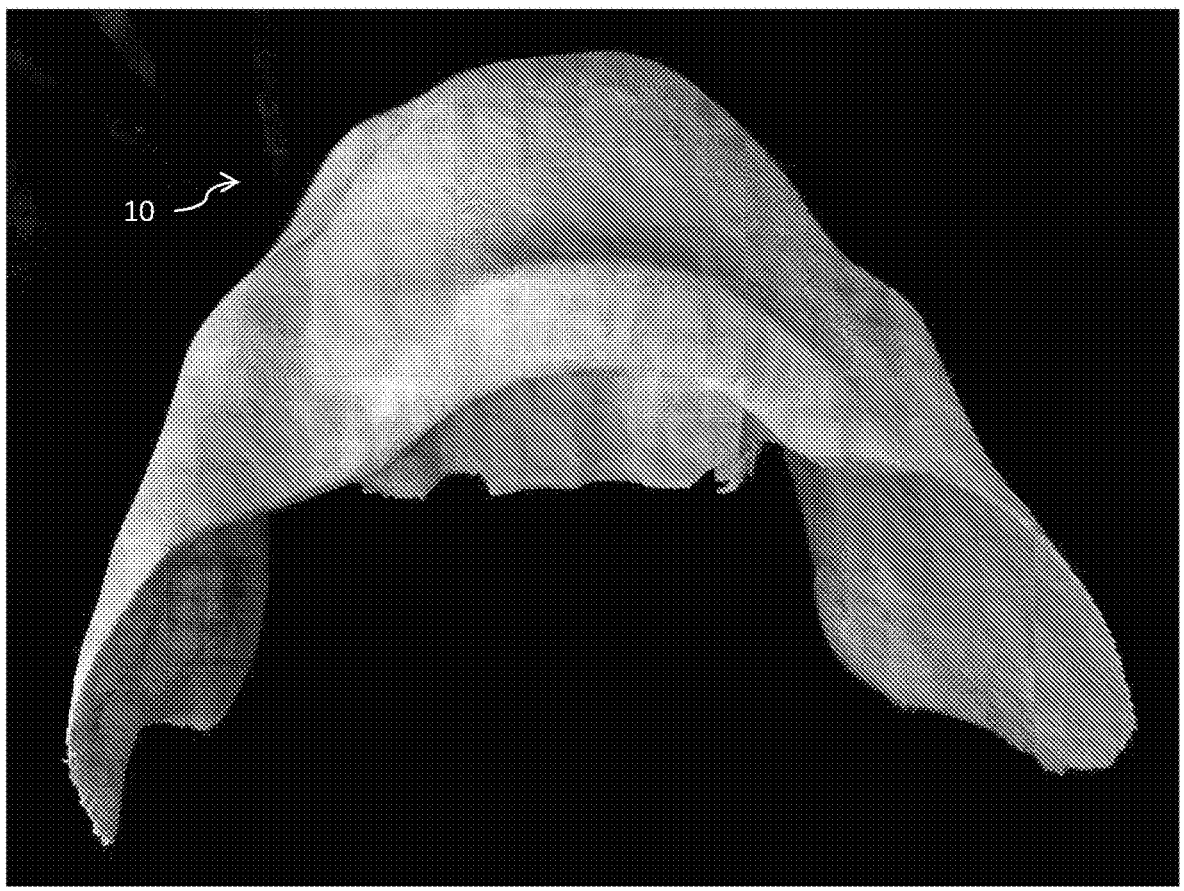
FIG. 11A shows an overhead view of an exemplary prosthesis formed from polylactic acid.
Figure 11B:
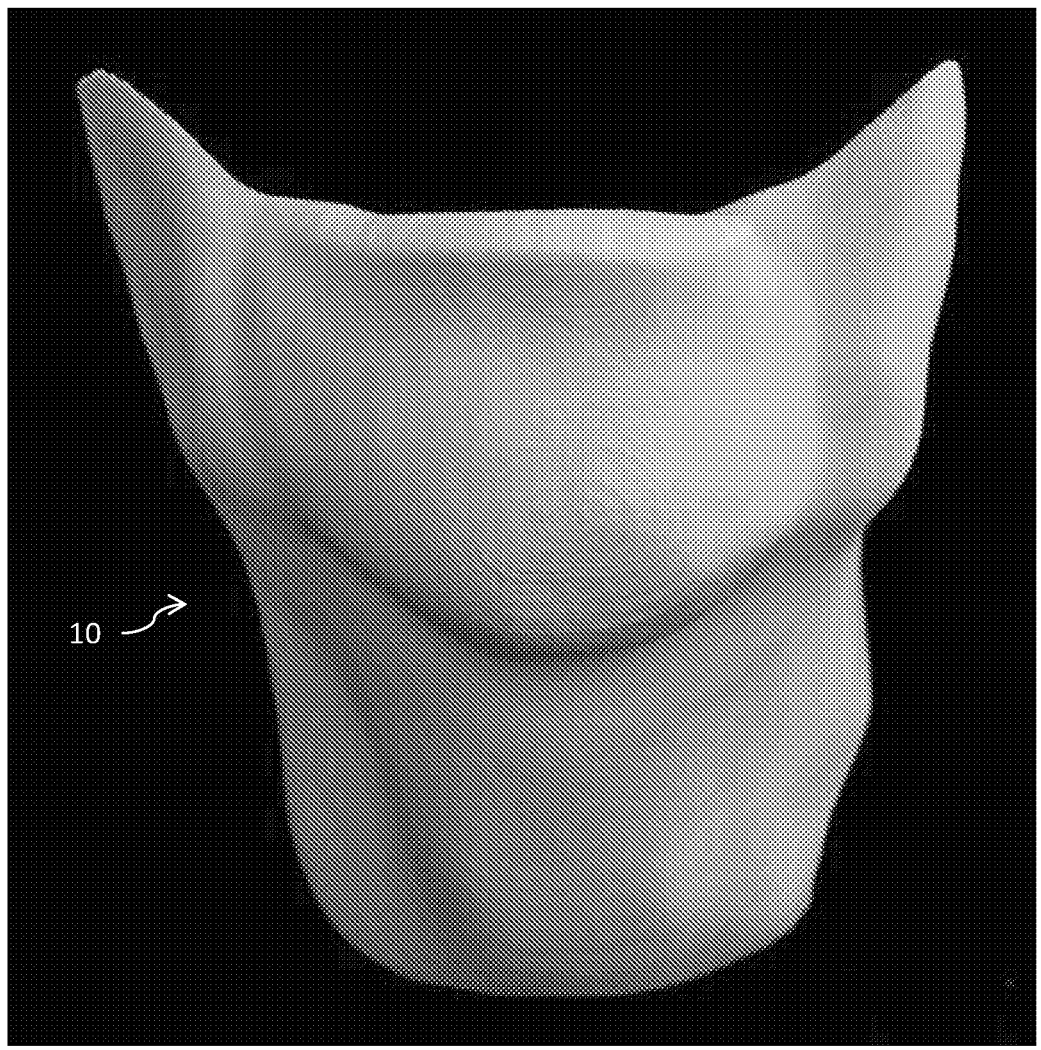
FIG. 11B shows a front view of the exemplary prosthesis of FIG. 11A.
Figure 11C:
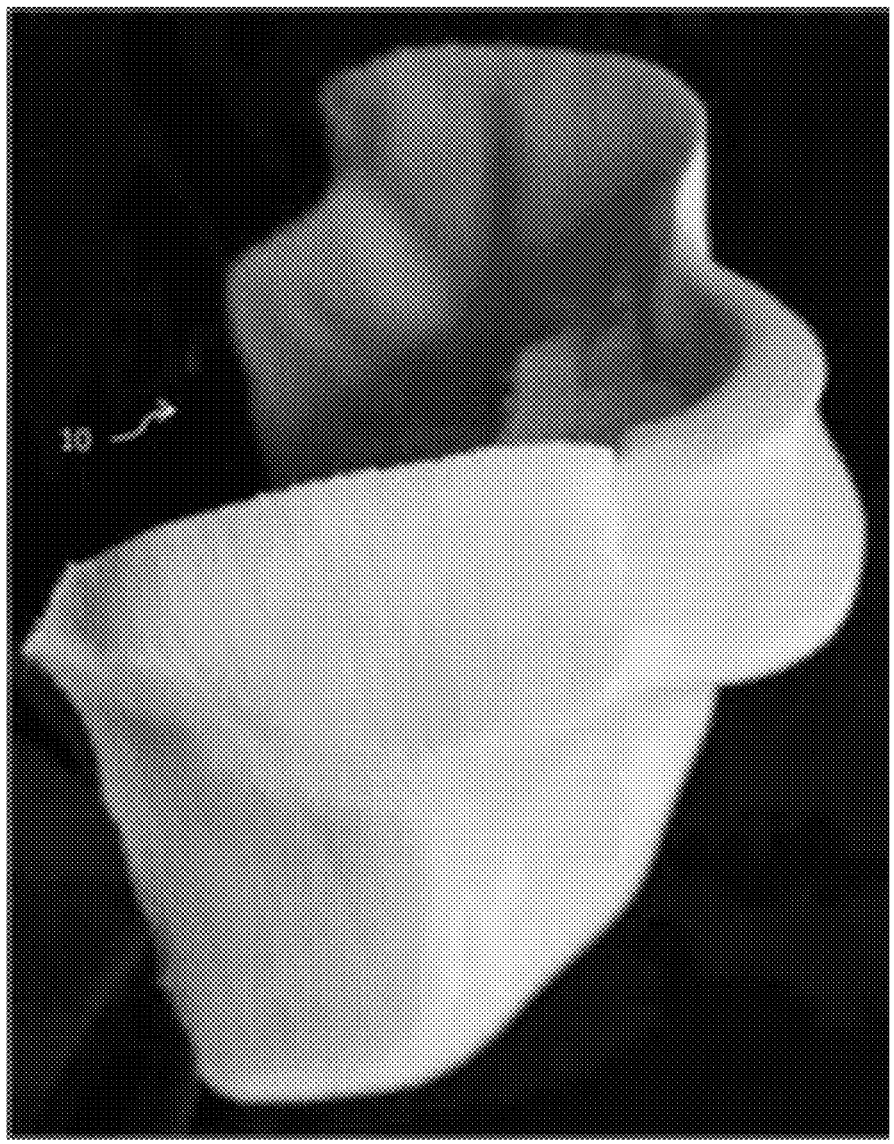
FIG. 11C shows an elevated side view of the exemplary prosthesis of FIG. 11A.
Figure 11D:
FIG. 11D shows a detail of the exemplary prosthesis of FIG. 11A.

The designed prosthesis 10 was then formed using fused deposition modeling (FDM) using a rapid prototyping device 36 such as a commercial 3D printer from MakerBot, as shown in FIG. 10. The scaffolding was printed using polylactic acid (PLA) to provide a lightweight, flexible mold. FIG. 11A shows an overhead view of the exemplary prosthesis 10 shown printed in FIG. 10. FIG. 11B shows a front view of the prosthesis 10. FIG. 11C shows an elevated side view of the prosthesis 10. FIG. 11D shows a detail of the exemplary prosthesis.

Although not illustrated, the scaffolding may be covered with a platinum-silicone material as described above, and the silicone may be polymerized by activating the platinum catalyst.

Figure 12:
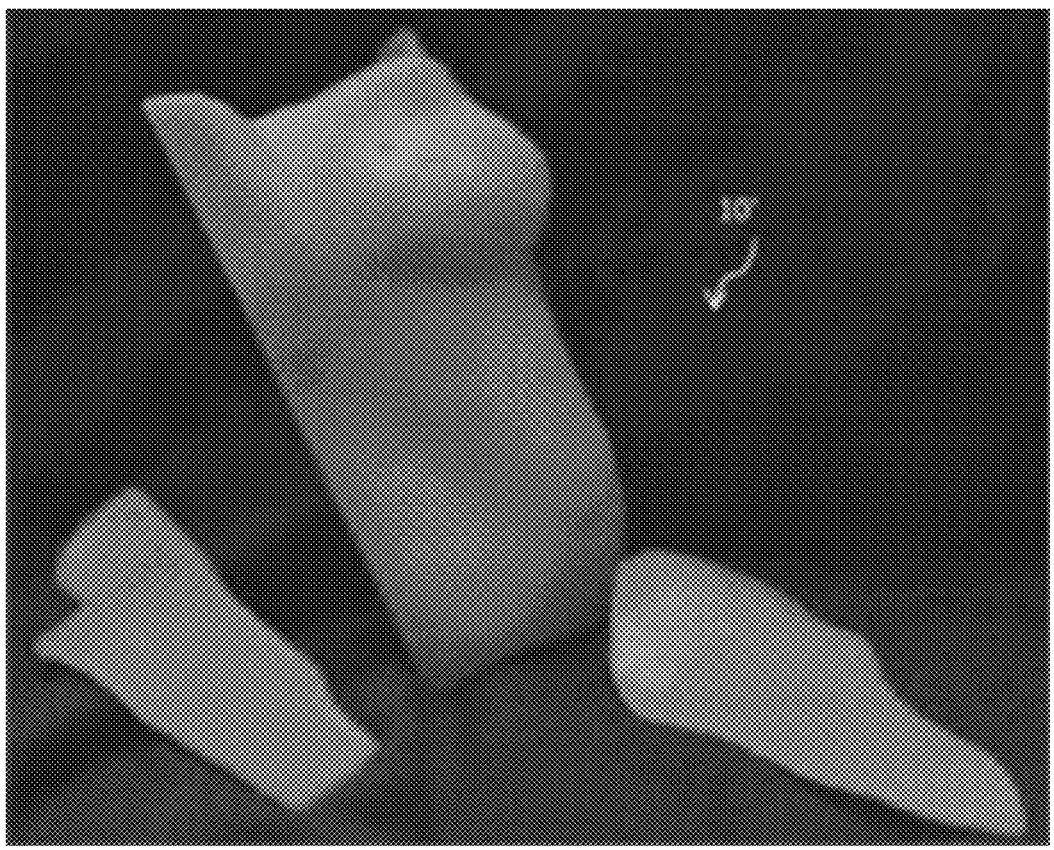
FIG. 12 illustrates a portion of another exemplary prosthesis formed from a methyacrylate polymer.

Another exemplary 3D printed prosthesis 10' is illustrated in FIG. 12. The prosthesis illustrated in FIG. 12 more closely follows the contours of the patient's face to use less of the bulk material compared to a typical block mold. The prosthesis 10' illustrated in FIG. 12 was printed using a FormLabs hard resin methacrylate polymer, and is an illustrative example of one half/side of the mold. The three pieces of the prosthesis 10' illustrated in FIG. 12 together create the outer section of the face to form the platinum-silicone that is backed by another 3D printed mold. The detail impression is sufficient to put platinum-silicone between the two 3D printed molds to create a very thin facial prosthesis out of silicone or other appropriate materials.

Figure 13:
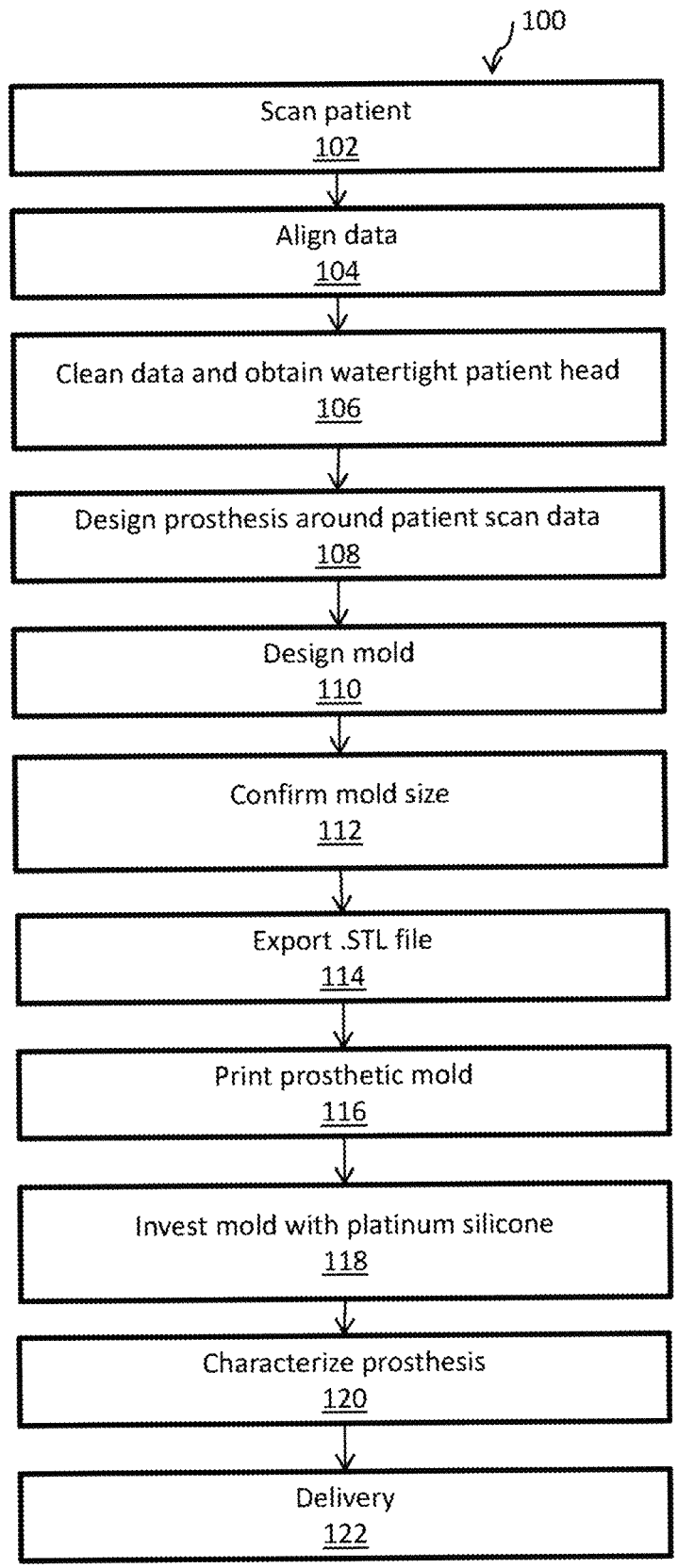
FIG. 13 illustrates an exemplary method of providing a prosthesis to a patient.

Referring next to FIG. 13, an exemplary method 100 of providing a prosthesis to a patient is illustrated. In one aspect, the prosthesis provided in method 100 is configured to be anchored to the patient with adhesives, straps, or other suitable means.

In block 102, a scan of the patient is obtained, such as using a scanning apparatus 32 (FIG. 4). Exemplary scans may be obtained from photogrammetry systems such as the 3dMDface system or the Go! SCAN 50 three dimensional scanner available from Creaform Inc., Levis, Quebec, Canada.

In block 104, the scan data obtained in block 102 is input into a suitable device, such as design apparatus 34 (FIG. 4) and the scan data is aligned. In one exemplary method, the data is aligned and data artifacts are removed using a data alignment tool, such as Geomagic Design X, available from 3D Systems, Rock Hill, S.C. In block 106, the aligned data is cleaned to remove any data artifacts from scanning apparatus 32. Block 106 results in a data set representing a solid surface of the patient's scan area without gaps, holes, or other data artifacts.

In block 108, a prosthesis is designed around the data set obtained in block 106 using a graphic modeling software application. Exemplary graphic modeling software applications include non-parametric 3D modeling programs such as ZBrush, In some aspects, block 108 of method 100 is similar to the formation of the digital model of a prosthesis in block 58 of method 50 (see FIG. 6).

In block 110, a mold, such as mold 16, is designed for the digital model of the prosthesis formed in block 108. In some aspects, the graphic modeling software, such as ZBrush, is utilized to design the mold 16, and even more particularly, extractions and Boolean operations inside of the graphic modeling software are utilized to form the digital model of the mold 16.

In block 112, the mold size is confirmed by importing the digital model of the mold into a data alignment tool such as Geomagic Design X and aligning the digital model of the mold with the scan data aligned in block 104.

In block 114, a suitable export file for the mold 16 is provided from the data alignment tool. Suitable export file configurations include STereoLithography, or STL, type file formats. In block 116, the prosthesis mold 16 is printed, such as with a rapid prototyping device 36 (FIG. 4), such as a 3D printer. In block 118, the mold 16 is invested with silicone to form the prosthesis. In block 120, the prosthesis is characterized and finalized, prior to delivery to the patient in block 122.

Figure 14:
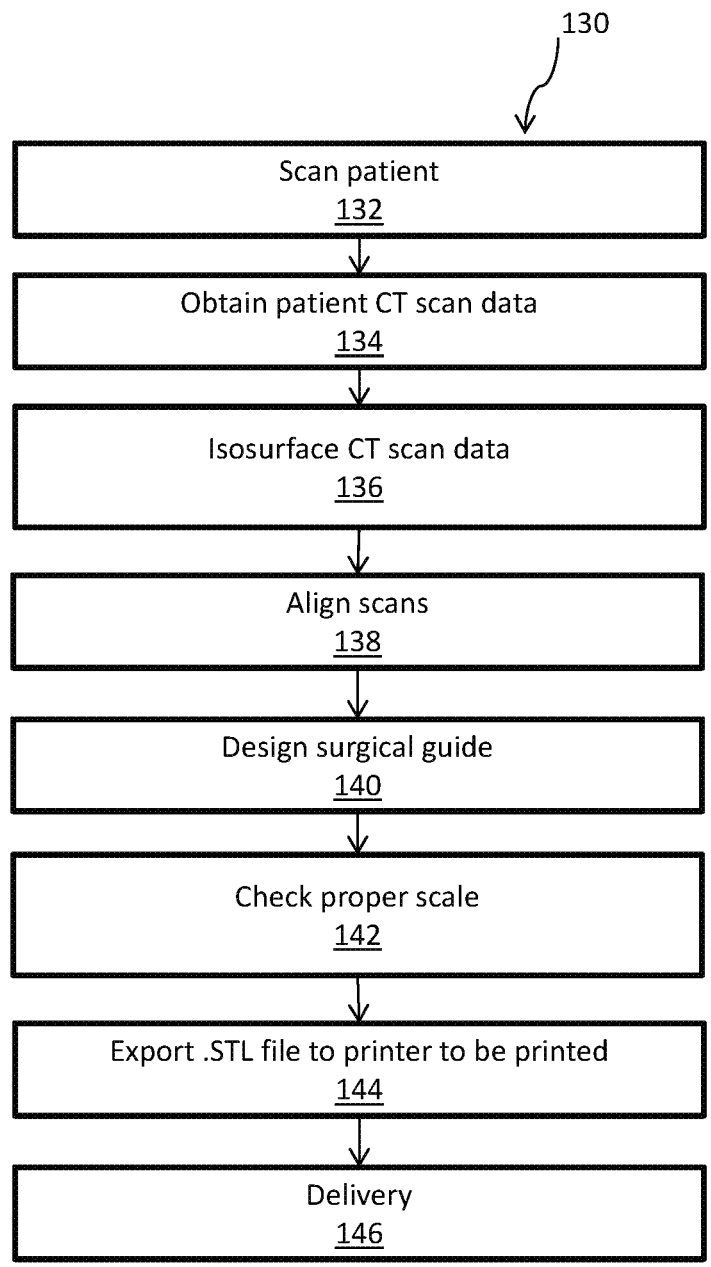
FIG. 14 illustrates an exemplary method of providing a surgical guide to a surgeon.

Referring next to FIG. 14, an exemplary method 130 of providing a surgical guide to a surgeon is illustrated. In one aspect, the method 130 is performed prior to surgery to implant or attached the prosthesis for the patent.

In block 132, a scan of the patient is obtained, such as using a scanning apparatus 32 (FIG. 4). Exemplary scans may be obtained from photogrammetry systems such as the 3dMDface system or the Go! SCAN 50 three dimensional scanner available from Creaform Inc., Levis, Quebec, Canada.

In block 134, patient computerized tomography (CT) scan data of the patient is provided. This data may be obtained from a new CT scan of the patient, or may be available from a previous scan. In block 136, the CT scan data is subjected to an isosurface module to obtain the flesh and bone geometry of the patient. In block 138, the patient scan data from block 132 and the CT scan data from block 136 are aligned to provide a high fidelity mesh of the patient scan data superimposed over the bone geometry provided by the CT scan. In one exemplary method, the data is aligned and data artifacts are removed using a data alignment tool, such as Geomagic Design X, available from 3D Systems, Rock Hill, S.C.

In block 140, a surgical guide is designed. The surgical guide is illustratively configured to be used to provide accurate placement of a surgical implant, such as the accurate placement of titanium implants into an adequate thickness of bone. In some aspects, the graphic modeling software, such as ZBrush, is utilized to design the surgical guide. In block 142, the surgical guide size is confirmed by importing the digital model of the surgical guide from block 140 into a data alignment tool such as Geomagic Design X and aligning the digital model of the surgical guide with the scan data aligned in block 138.

In block 144, a suitable export file for the surgical guide is provided from the data alignment tool, and the surgical guide is printed, such as with a rapid prototyping device 36 (FIG. 4), such as a 3D printer. In one aspect, the surgical guide may be formed from a class 1 biocompatible resin, such as Dental SG Resin available from Formlabs, Inc., Somerville, Mass. Suitable export file configurations include STereoLithography, or STL, type file formats. In block 146, the surgical guide is delivered to be used in surgery.

In another aspect, a prosthesis is designed using a method similar to method 130 in FIG. 14 for a patient in which an implant, such as a titanium implant, has previously been placed into the patient and healed. In this aspect, block 140 includes designing the prosthesis in view of the implants, where the prosthesis includes suitable means for attaching the prosthesis to the implant, such as with one or more magnets or a retention bar. The method is similar to method 130 for blocks 142-146, except that the prosthesis is used in place of a surgical guide.

Figure 15:
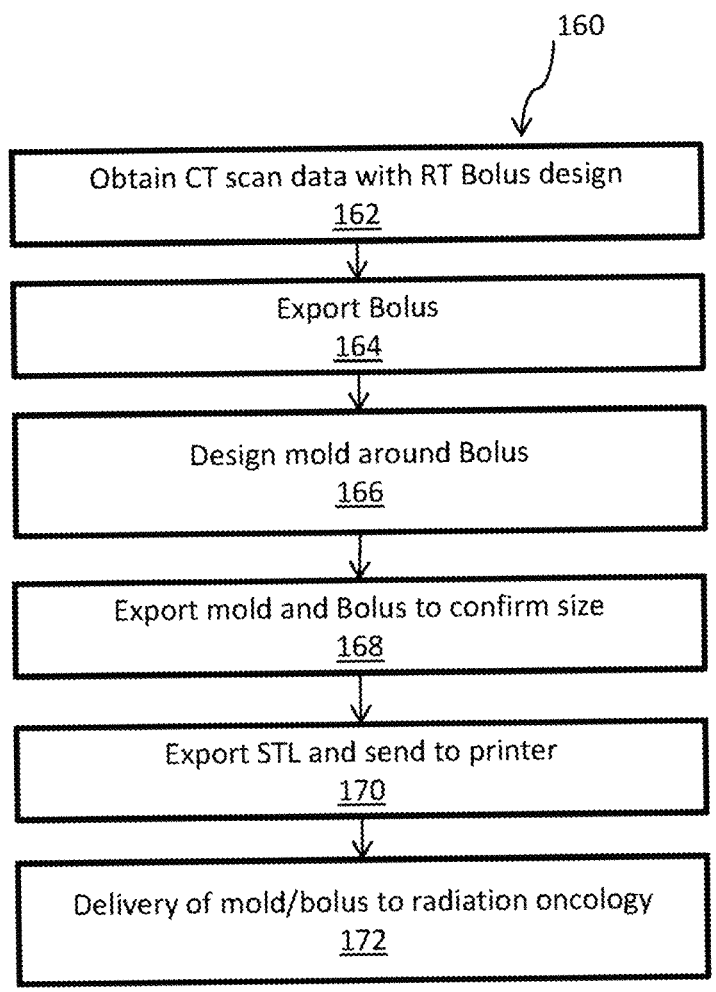
FIG. 15 illustrates an exemplary method of providing a bolus.

Referring next to FIG. 15, an exemplary method 160 of providing a bolus for radiation treatment is provided. A bolus is typically used to enhance dosimetry of radiation treatment and to avoid direct contact with unwanted areas of the body during radiation treatment. In block 162, patient computerized tomography (CT) scan data of the patient with a RT bolus design is provided. This data may be obtained from a new CT scan of the patient with the bolus, or may be available from a previous scan, such as a scan performed by a radiation oncologist. In block 164, the data from the scan relating to the bolus is separated from the data relating to the patient using a visualization application or module such as 3D Slicer maintained by The Brigham and Women's Hospital, Inc. In block 166, the data relating to the bolus is imported into a graphic modeling software, such as ZBrush, which is utilized to design a mold. In block 168, the mold size is confirmed by importing the digital model of the mold from block 166 into a data alignment tool such as Geomagic Design X and aligning the digital model of the mold with the scan data from block 162. In block 170, a suitable export file for the mold is provided from the data alignment tool, and the mold is printed, such as with a rapid prototyping device 36 (FIG. 4), such as a 3D printer. Suitable export file configurations include STereoLithography, or STL, type file formats. In block 172, the mold may be provided for surgery directly, or the mold may be invested with silicone to form the bolus, which is then provided for radiation treatment.

Figure 16:
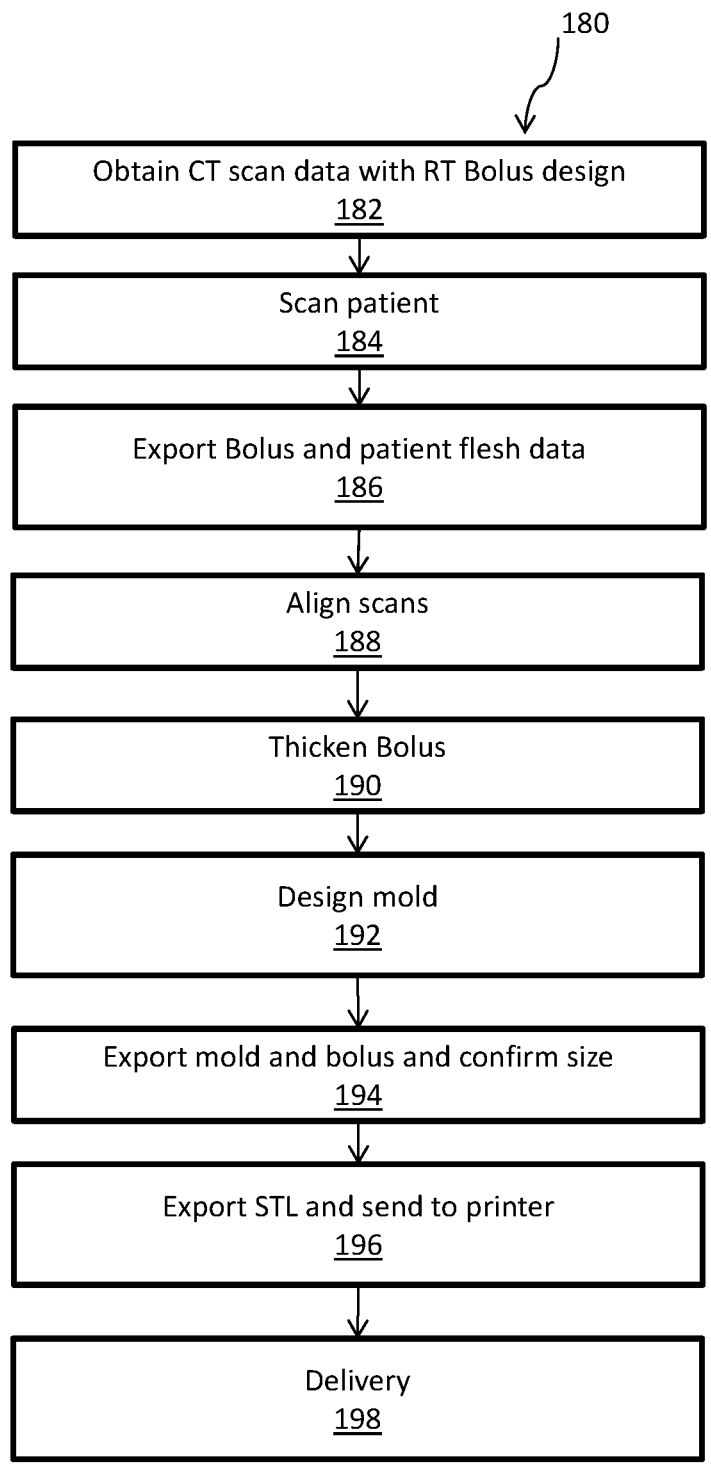
FIG. 16 illustrates another exemplary method of providing a bolus.

Referring next to FIG. 16, another exemplary method 180 of providing a bolus is provided. In block 182, patient computerized tomography (CT) scan data of the patient with a RT bolus design is provided. This data may be obtained from a new CT scan of the patient with the bolus, or may be available from a previous scan, such as a scan performed by a radiation oncologist. In block 184, a scan of the patient is obtained, such as using a scanning apparatus 32 (FIG. 4). Exemplary scans may be obtained from photogrammetry systems such as the 3dMDface system or the Go! SCAN 50 three dimensional scanner available from Creaform Inc., Levis, Quebec, Canada. In block 186, the data from the scan relating to the bolus is separated from the data relating to the patient using a visualization application or module such as 3D Slicer maintained by The Brigham and Women's Hospital, Inc. In block 188, the patient scan data from block 184 and the CT scan data from block 186 are aligned to provide a high fidelity mesh of the patient scan data superimposed over the bone geometry provided by the CT scan. In one exemplary method, the data is aligned and data artifacts are removed using a data alignment tool, such as Geomagic Design X, available from 3D Systems, Rock Hill, S.C. In block 190, the scan data is imported into a graphic modeling software, such as ZBrush, and the data is modified to thicken the bolus. A Boolean subtraction out of the thickened bolus of the patient scan data from block 184 is taken to eliminate data artifacts due to possible air pockets that may be present. In block 192, the graphic modeling software is utilized to design a mold around the bolus. In block 194, the mold size is confirmed by importing the digital model of the mold from block 192 into a data alignment tool such as Geomagic Design X and aligning the digital model of the mold with the bolus data from block 186. In block 196, a suitable export file for the mold is provided from the data alignment tool, and the mold is printed, such as with a rapid prototyping device 36 (FIG. 4), such as a 3D printer. Suitable export file configurations include STereoLithography, or STL, type file formats. In block 198, the mold may be provided directly, or the mold may is invested with silicone to form the bolus, which is then provided.

Figure 17:
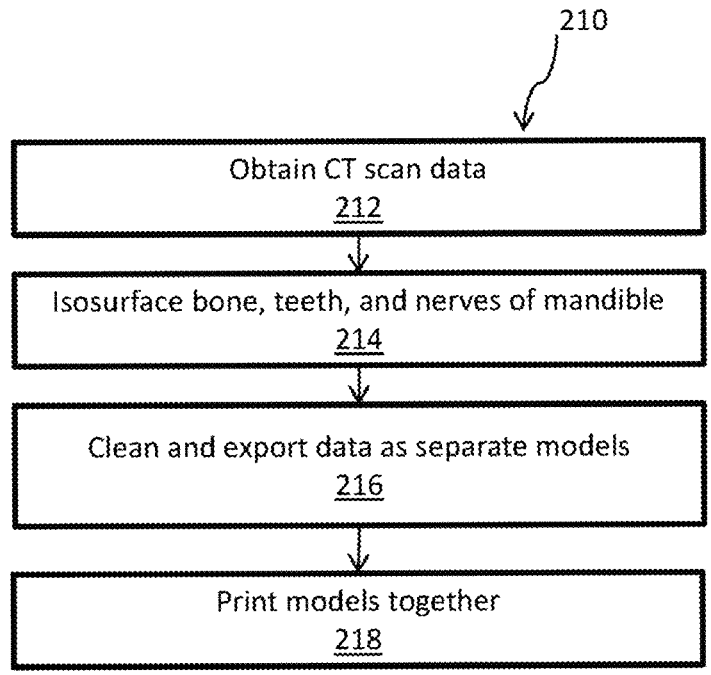
FIG. 17 illustrates an exemplary pre-surgical method for a mandibular prosthesis.

Referring next to FIG. 17, an exemplary method 210 for a pre-surgical workflow, and more particularly, for a mandibular pre-surgical model. While FIG. 17 is particular to a mandibular pre-surgical model, those of skill in the art will recognize that other pre-surgical models may also be formed by a similar method. In block 212, patient computerized tomography (CT) scan data of the patient's mandibular region is provided. This data may be obtained from a new CT scan of the patient with the bolus, or may be available from a previous scan, such as a scan performed by a radiation oncologist. In block 214, the CT scan data is subjected to an isosurface module to obtain the flesh and bone geometry of the patient. In block 216, the scan data is cleaned and data artifacts are removed using a data alignment tool, such as Geomagic Design X, available from 3D Systems, Rock Hill, S.C. Separate data sets are produced for separate systems, such as separate models for the jaw, nerves and teeth, etc. In step 218, the a model including the separate systems is printed by printing the separate systems together using a rapid prototyping device 36 (FIG. 4), such as a 3D printer. In some aspects, each system (jaw, nerves and teeth, etc.) is printed from a different material, allowing the printed model to have different properties for each system. For example, each system could be printed in a different color and/or printed with a different shape, density, thickness, and/or size to provide various surface tensions, hardness, and/or flexibility for each portion of the model. The formed model may then be used to prepare a surgical guide. In an exemplary aspect, a plate for use as part of the guide may be bent around the model of the mandible, enabling a user to plant holes for use in implanting a prosthesis or surgical implant that will not harm roots of the teeth or the mandibular nerve, for example.

Figure 18:
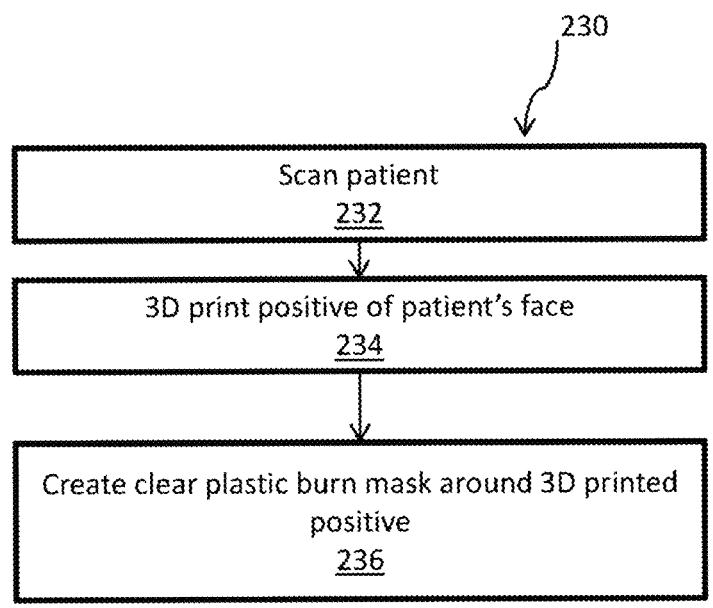
FIG. 18 illustrates an exemplary workflow for a burn victim mask.
Figure 19:
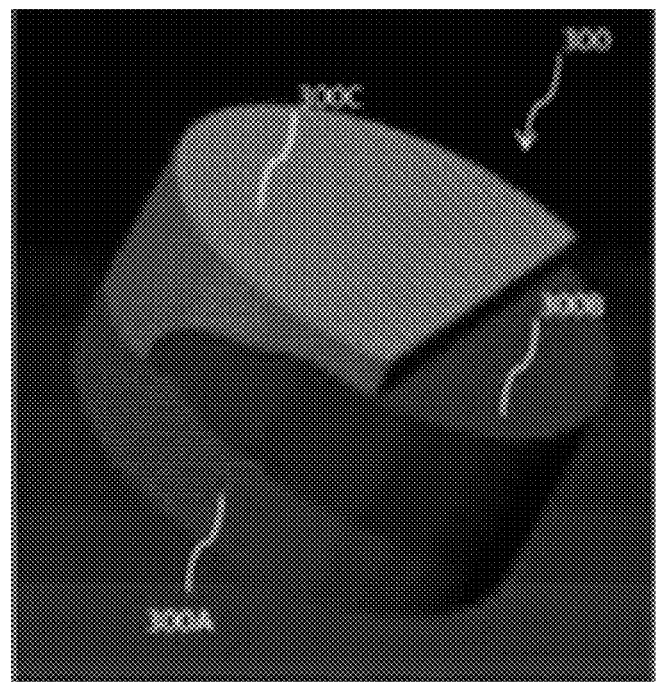
FIG. 19 illustrates a digital model of a 3-piece compression type mold for forming an auricular prosthesis.
Figure 20:
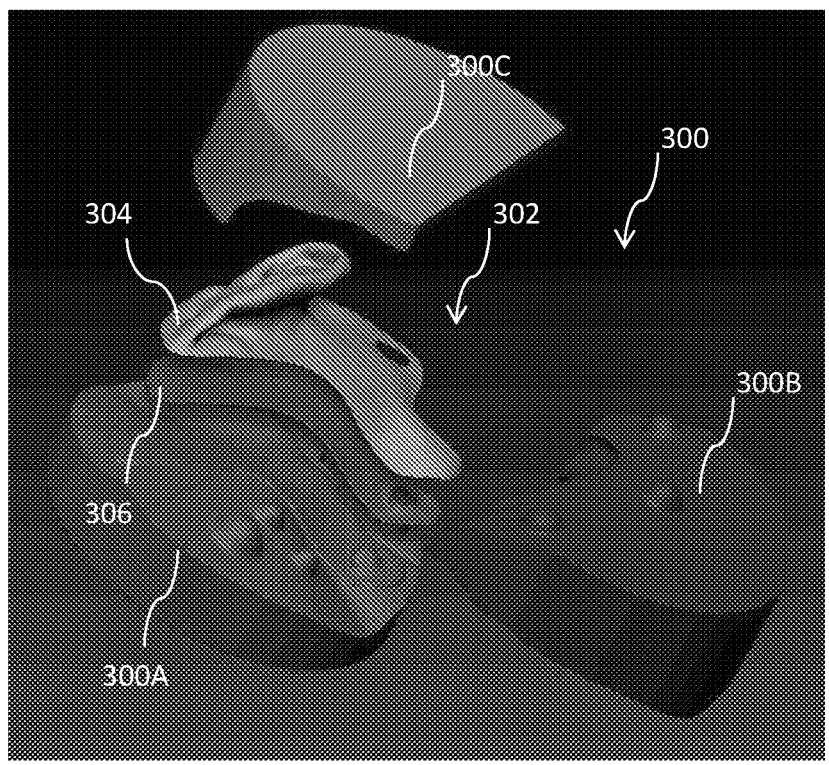
FIG. 20 illustrates an exploded view of the 3-piece compression type mold of FIG. 19 showing the auricular prosthesis.
Figure 21A:
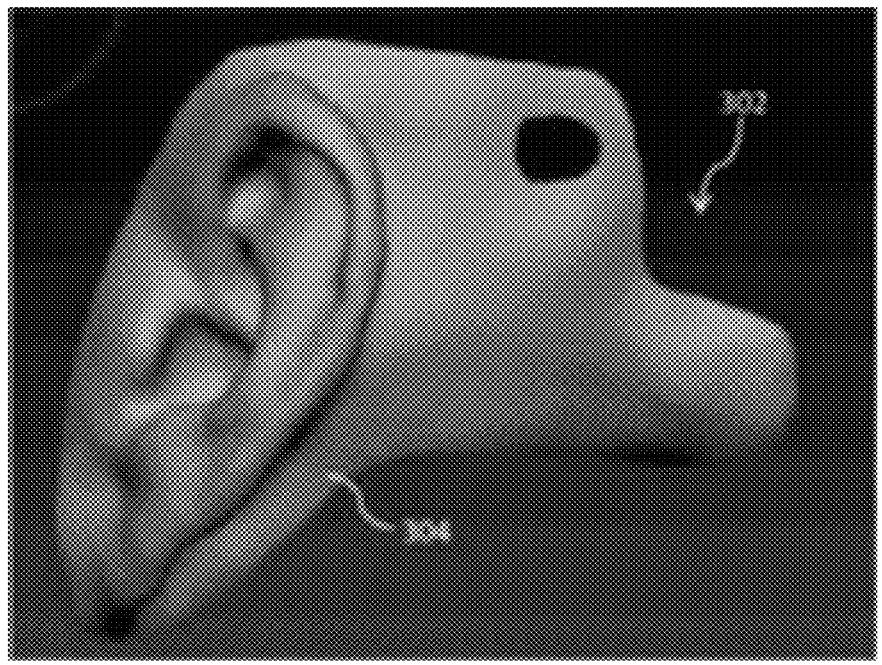
FIG. 21A illustrates a front view of the auricular prosthesis of FIG. 20.
Figure 21B:
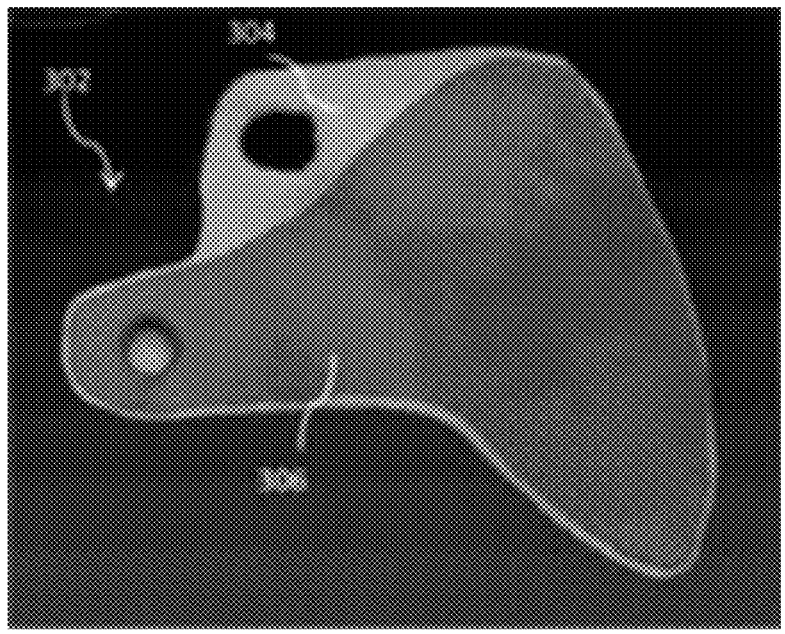
FIG. 21B illustrates a back view of the auricular prosthesis of FIG. 21.

Referring next to FIG. 18, an exemplary method 230 for providing a burn mask for a patient. In block 232, a scan of the affected area of the patient, such as the patient's face, is obtained, such as using a scanning apparatus 32 (FIG. 4). Exemplary scans may be obtained from photogrammetry systems such as the 3dMDface system or the Go! SCAN 50 three dimensional scanner available from Creaform Inc., Levis, Quebec, Canada. In block 234, a three-dimensional positive model of the patient's affected area is printed with a rapid prototyping device 36 (FIG. 4), such as a 3D printer. In block 236, a burn mask, such as clear plastic burn mask, is formed over the three-dimensional model by forming a pliable plastic sheet over the three-dimensional model in a thermoforming or vacuum forming machine. Alternatively, a negative mold of the three-dimensional model may be printed by the rapid prototyping device, and the negative mold invested with plaster to form a positive three-dimensional model. A burn mask, such as clear plastic burn mask, may formed over the plaster model by forming a pliable plastic sheet over the three-dimensional model in a thermoforming or vacuum forming machine.

Figure 22:
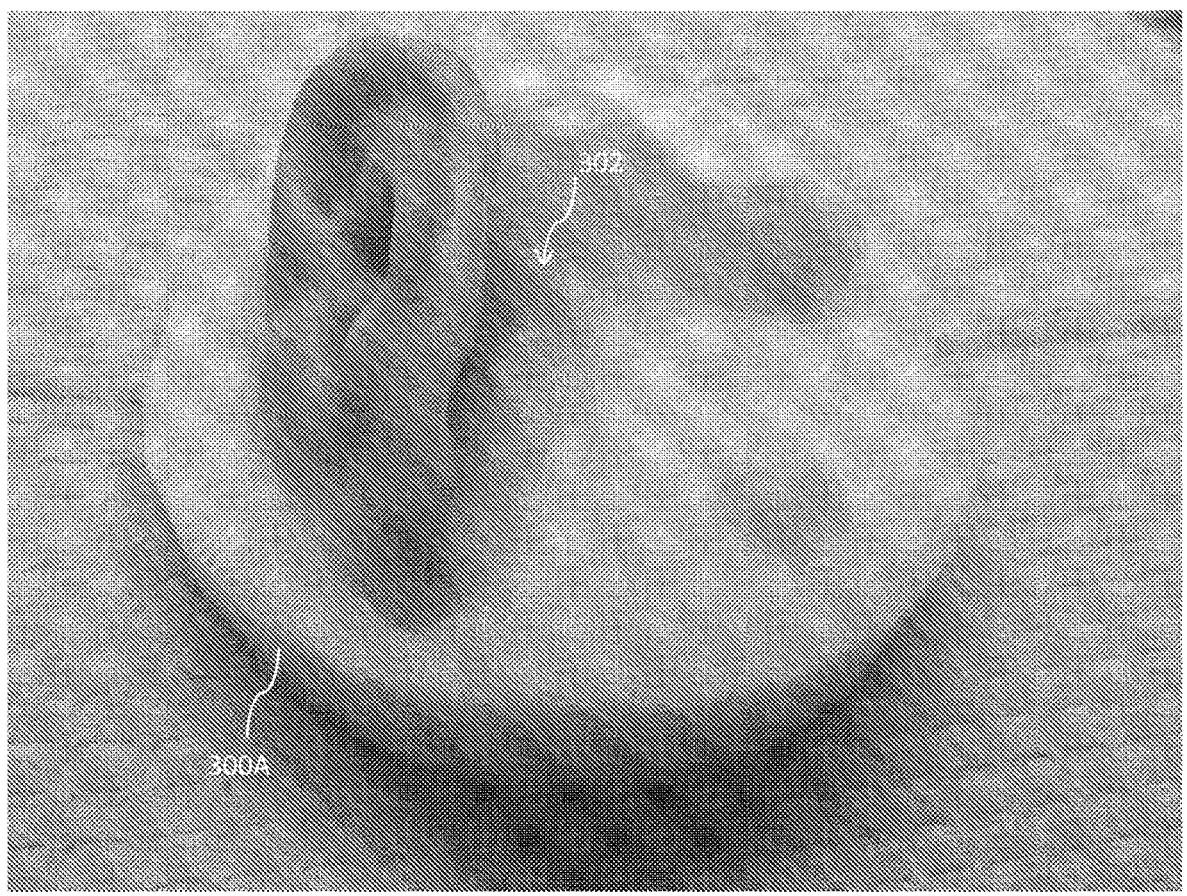
FIG. 22 illustrates the prosthesis formed from the mold of FIG. 20.
Figure 23:
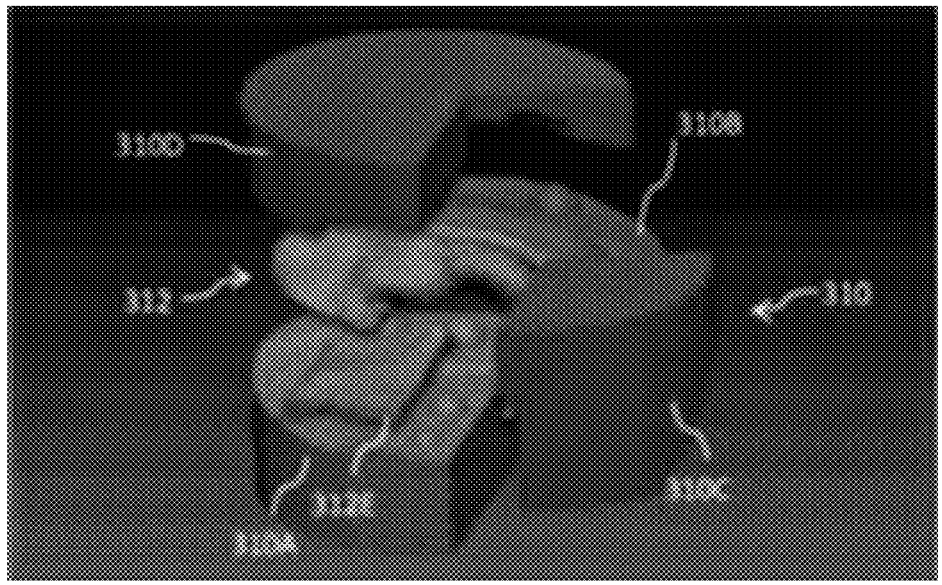
FIG. 23 illustrates an exploded view of a digital model of 4-piece compression type mold for forming a partial ear prosthesis.
Figure 24:
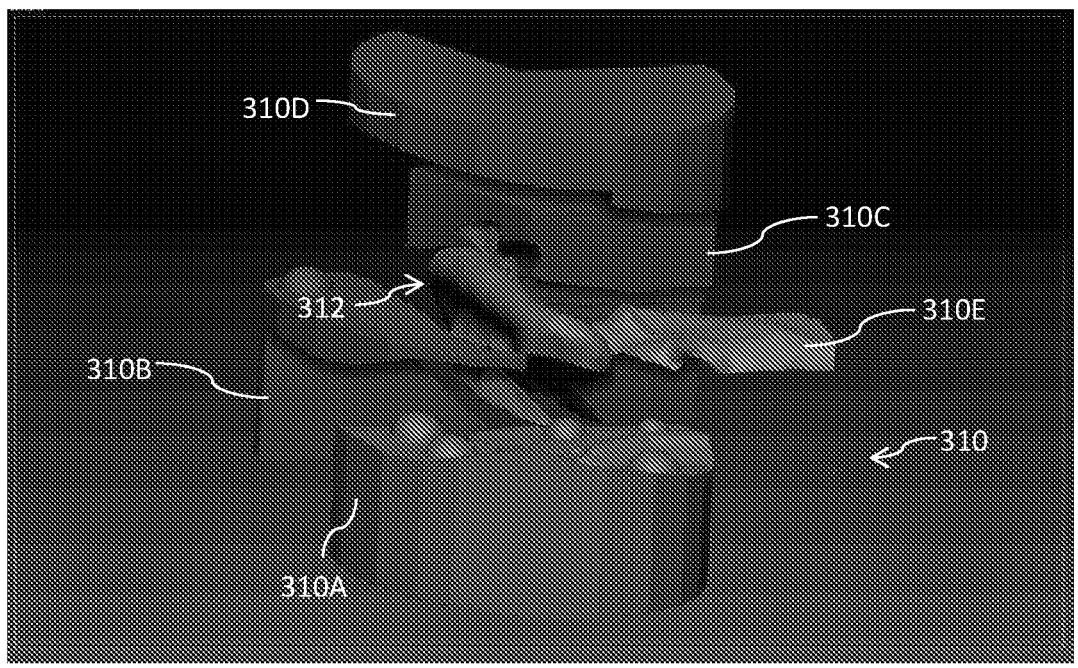
FIG. 24 illustrates another view of the digital model of FIG. 23.
Figure 25:
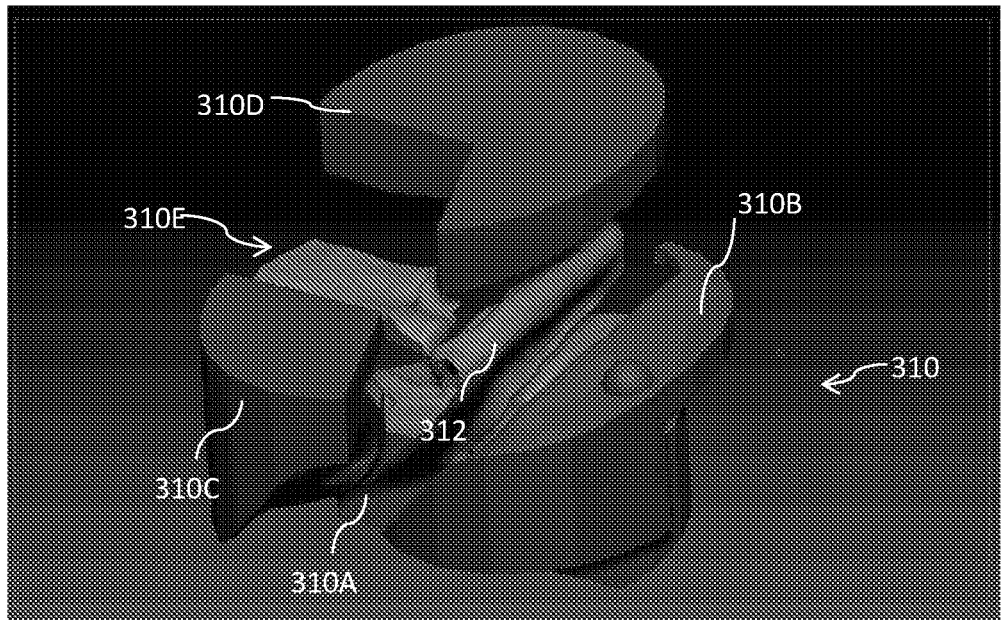
FIG. 25 illustrates still another view of the digital model of FIG. 23.

Referring next to FIGS. 19-22, an exemplary mold 300 is illustrated for forming an auricular (ear) prosthesis 302. Prosthesis 302 may be formed from method 100 (FIG. 13). Mold 300 is illustratively a 3-piece compression type mold formed form three pieces, 300A, 300B, and 300C, wherein the pieces 300A-300C define a cavity for forming the prosthesis 302. The prosthesis 302 is molded by investing platinum silicone 304 over three-dimensionally printed scaffolding 306 in the mold 300. The silicone 304 portion is illustratively supported and held rigid to the patient's face with scaffolding 306. The scaffolding 306 illustratively provides strength to the prosthesis 302, while allowing the prosthesis 302 to remain light. The formed prosthesis 302 illustrated in FIG. 22 is shown prior to characterization (block 120 in FIG. 13).

Figure 26:
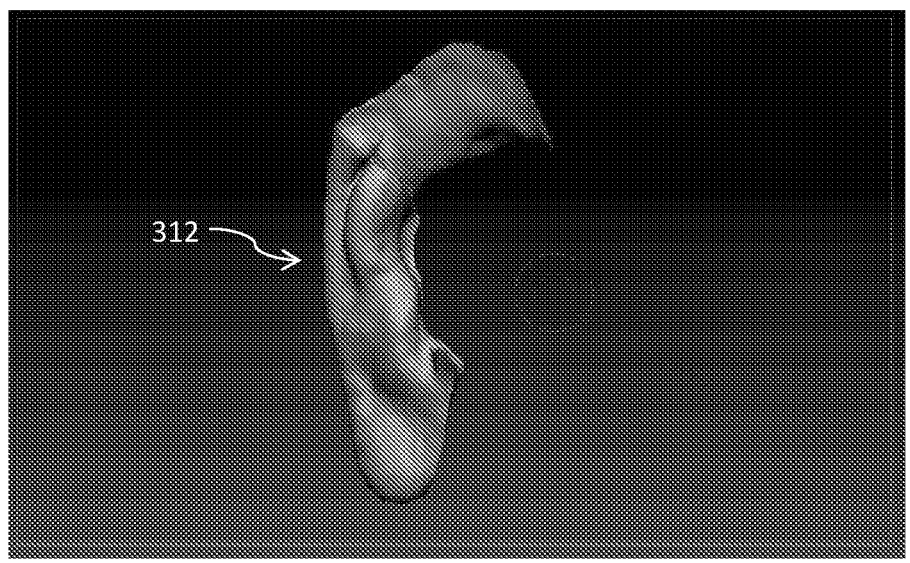
FIG. 26 illustrates a digital model of the partial ear prosthesis formed from the mold of FIG. 23.
Figure 27:
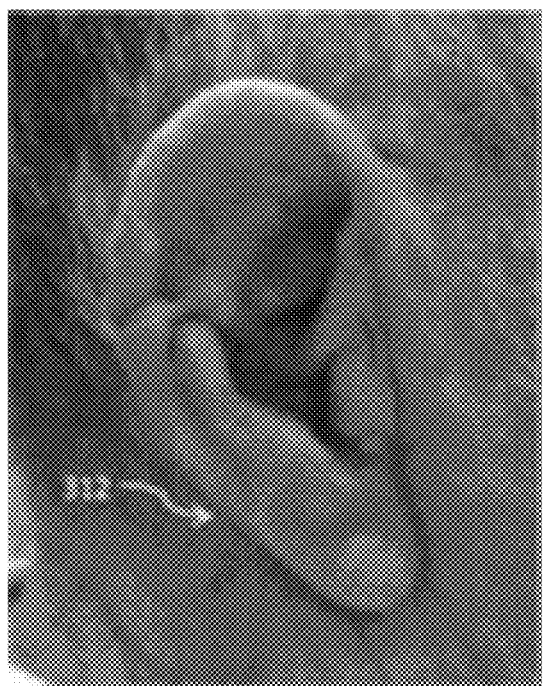
FIG. 27 illustrates the partial ear prosthesis formed from the mold of FIG. 23.
Figure 28:
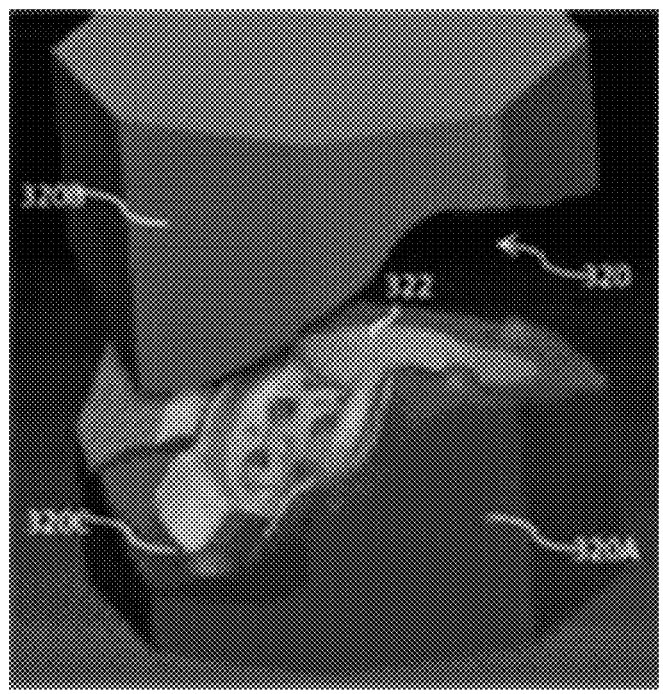
FIG. 28 illustrates a digital model of a 3-piece compression type mold for forming an interim nasal prosthesis.

Referring next to FIGS. 23-27, another exemplary mold 310 is illustrated for forming a partial ear prosthesis 312. Prosthesis 312 may be formed from method 100 (FIG. 13). Mold 310 is illustratively a 5-piece compression type mold formed form four pieces, 310A, 310B, 310C, 310D, and 310E, wherein the pieces 310A-310E define a cavity for forming the prosthesis 312. The prosthesis 312 is molded by investing platinum silicone in the mold 300. A digital model of prosthesis 312 is illustrated in FIG. 26, while FIG. 27 shows the prosthesis after characterization (block 120 in FIG. 13) as worn by the patient.

Figure 29:
FIG. 29 illustrates a digital model of the interim nasal prosthesis formed from the mold in FIG. 28.
Figure 30:
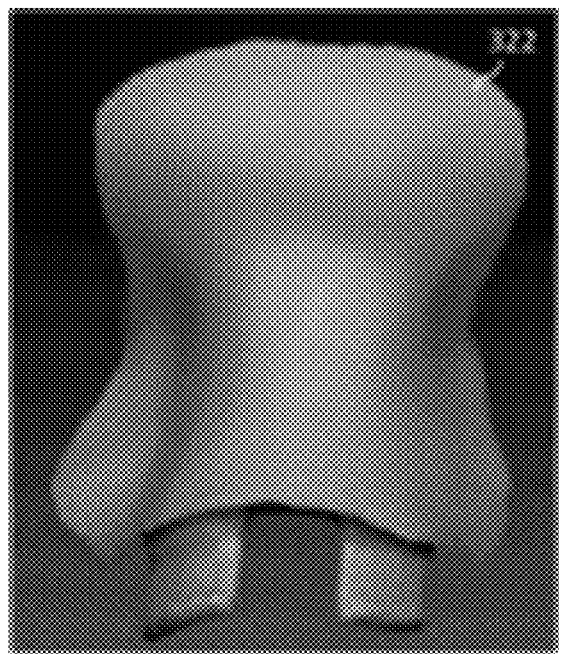
FIG. 30 illustrates a front view of the digital model of the interim nasal prosthesis in FIG. 29.
Figure 31:
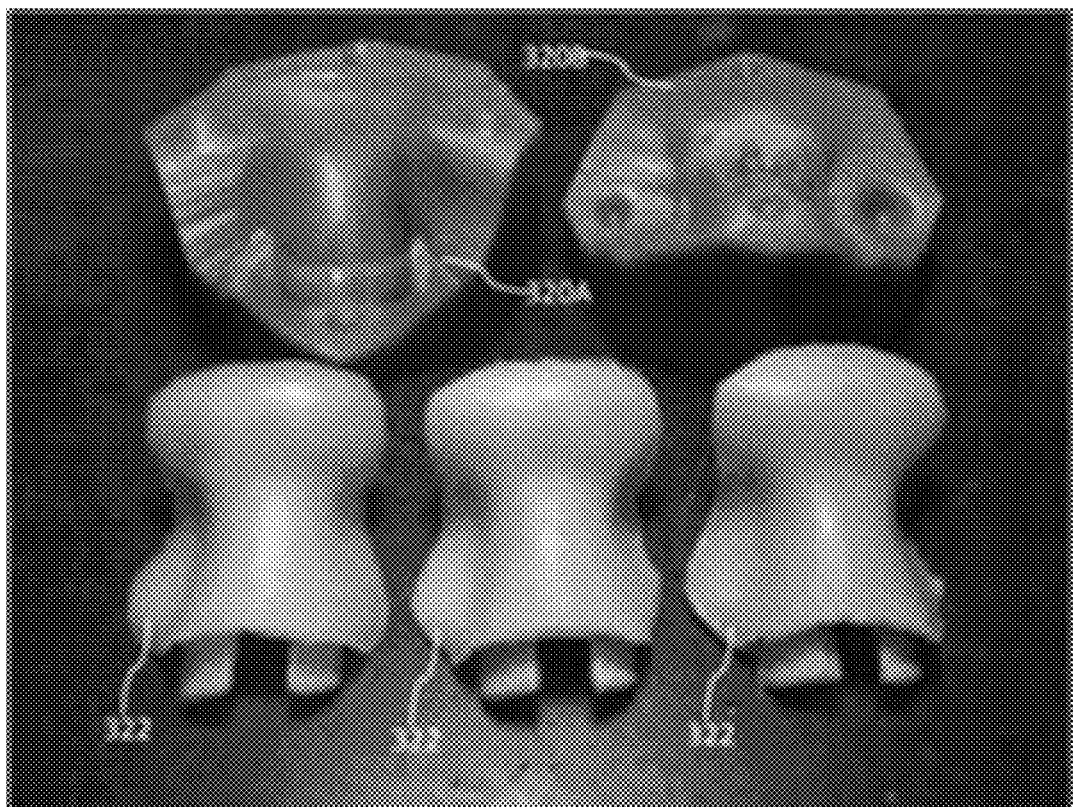
FIG. 31 illustrates the mold and interim nasal prosthesis formed from the digital model in FIG. 28.
Figure 32:
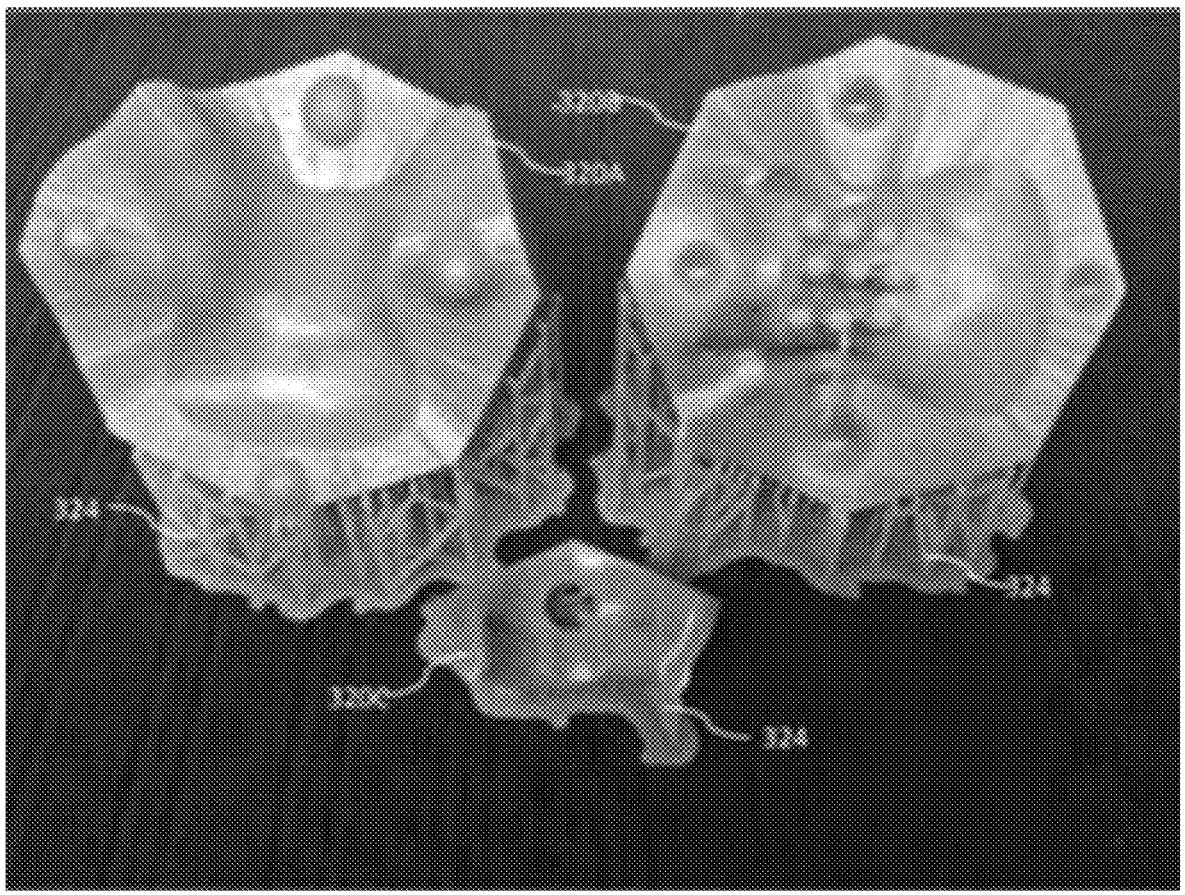
FIG. 32 illustrates the 3-part compression type mold of FIG. 28 after printing.

Referring next to FIGS. 28-32, another exemplary mold 320 is illustrated for forming an interim nasal prosthesis 322. The interim nasal prosthesis 322 is configured to cover a patient's wounds after surgery until a finalized prosthetic deliverable can be created. Interim nasal prosthesis may be formed from method 100 (FIG. 13). Mold 320 is illustratively a 3-piece compression type mold formed form three pieces, 320A, 320B, and 320C, wherein the pieces 320A-320C define a cavity for forming the prosthesis 322. FIGS. 29 and 30 show a digital model of the interim nasal prosthesis, as designed in block 108 (FIG. 13), and FIG. 32 shows the mold as designed and printed in blocks 110 and 116 (FIG. 13). FIG. 32 illustrates pieces 320A, 320B, and 320C as printed in block 116 (FIG. 13) This photo was taken after step 116 of FIG. 13, and prior to removal of the support material 324 from mold pieces 320A, 320B, and 320C. Three interim nasal prosthesis 322 after characterization (block 120 in FIG. 13) are shown in FIG. 31.

Figure 33A:
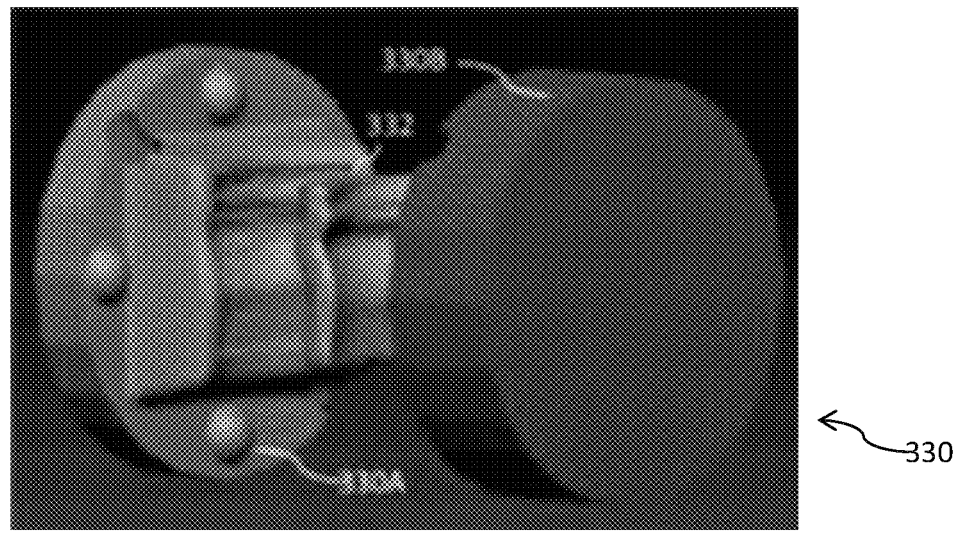
FIGS. 33A-B illustrate a digital model of 2-piece compression type mold for forming a radiation oncology bolus structure.
Figure 33B:
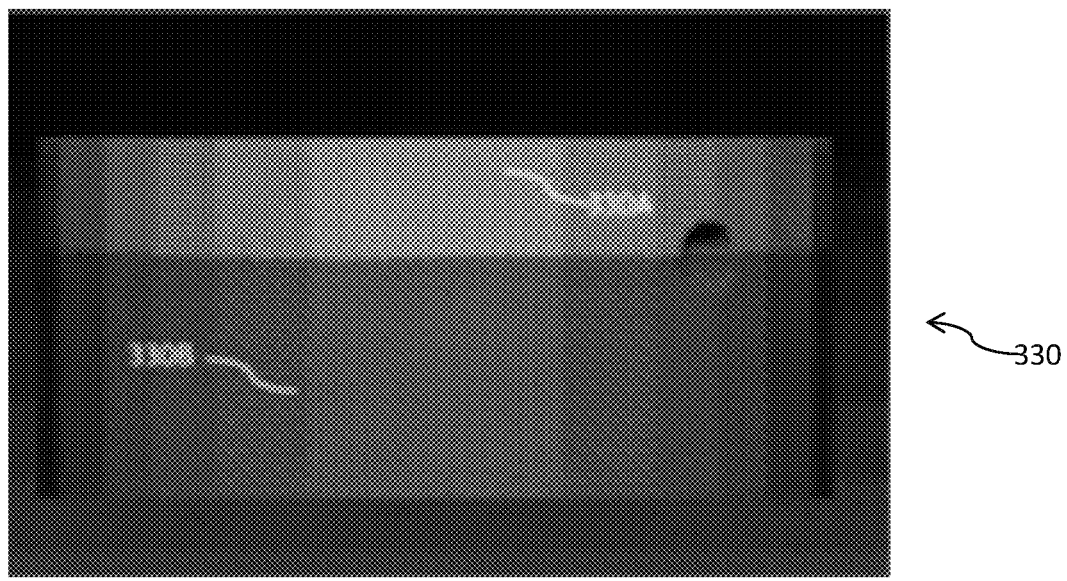
Figure 34A:
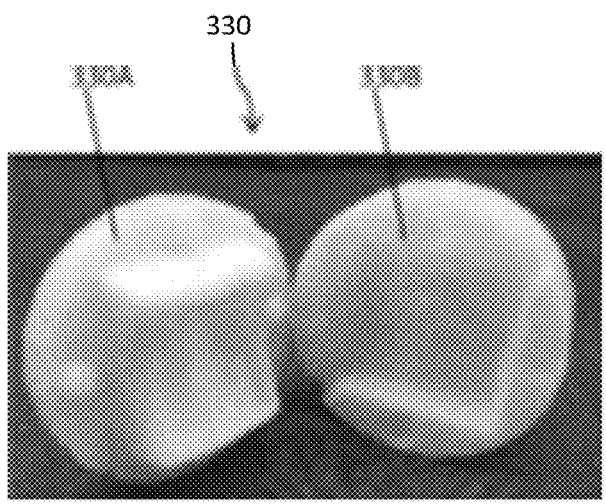
FIGS. 34A-D illustrate a 2-piece compression type mold formed from the digital model of FIGS. 33A-B.
Figure 34B:
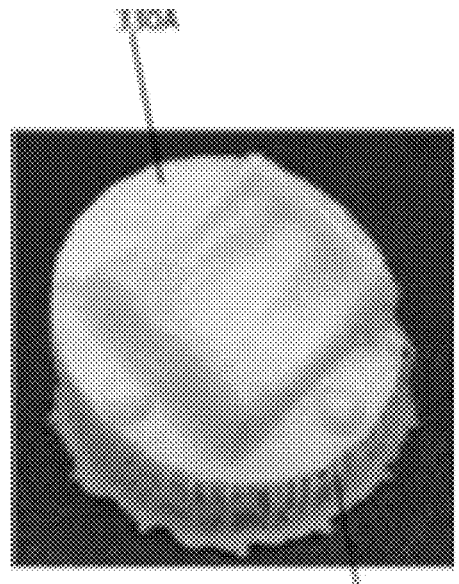
Figure 34C:
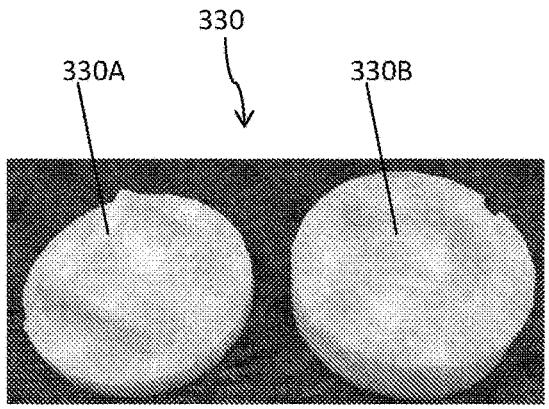
Figure 34D:
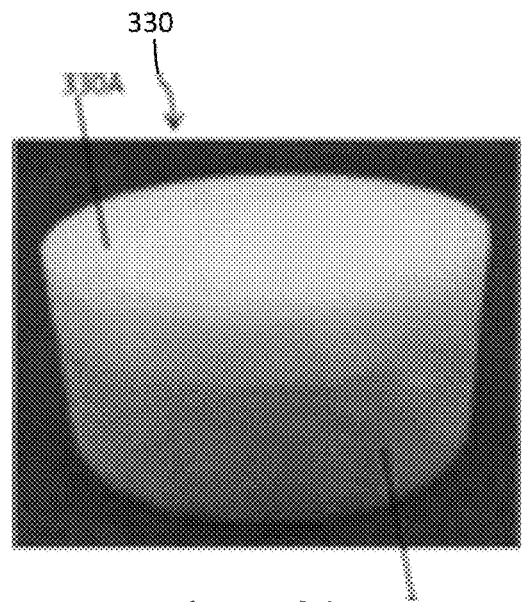
Figure 35A:
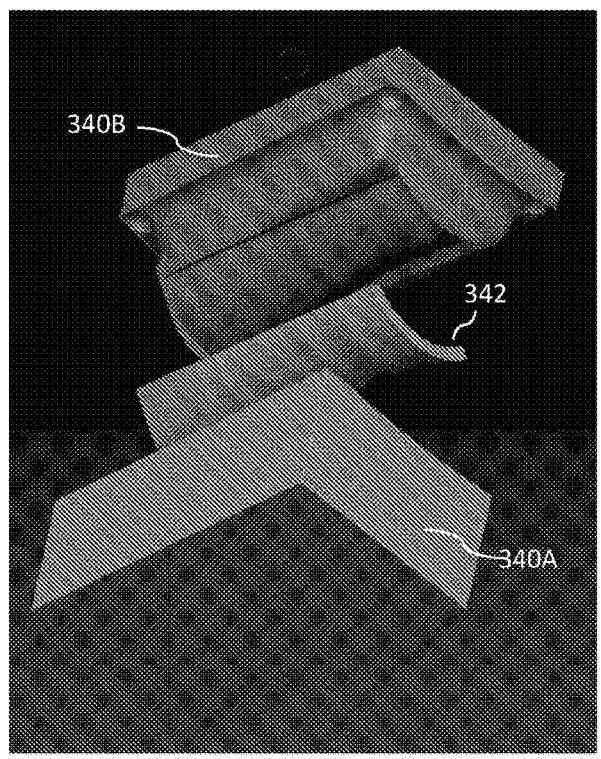
FIGS. 35A-B illustrate a digital model of 2-piece compression type mold for for investing a radiation oncology bolus structure
Figure 35B:
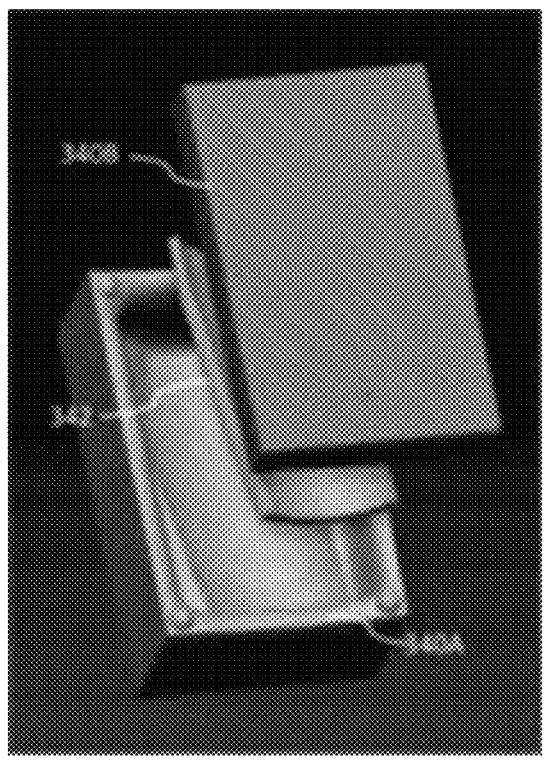
Figure 36A:
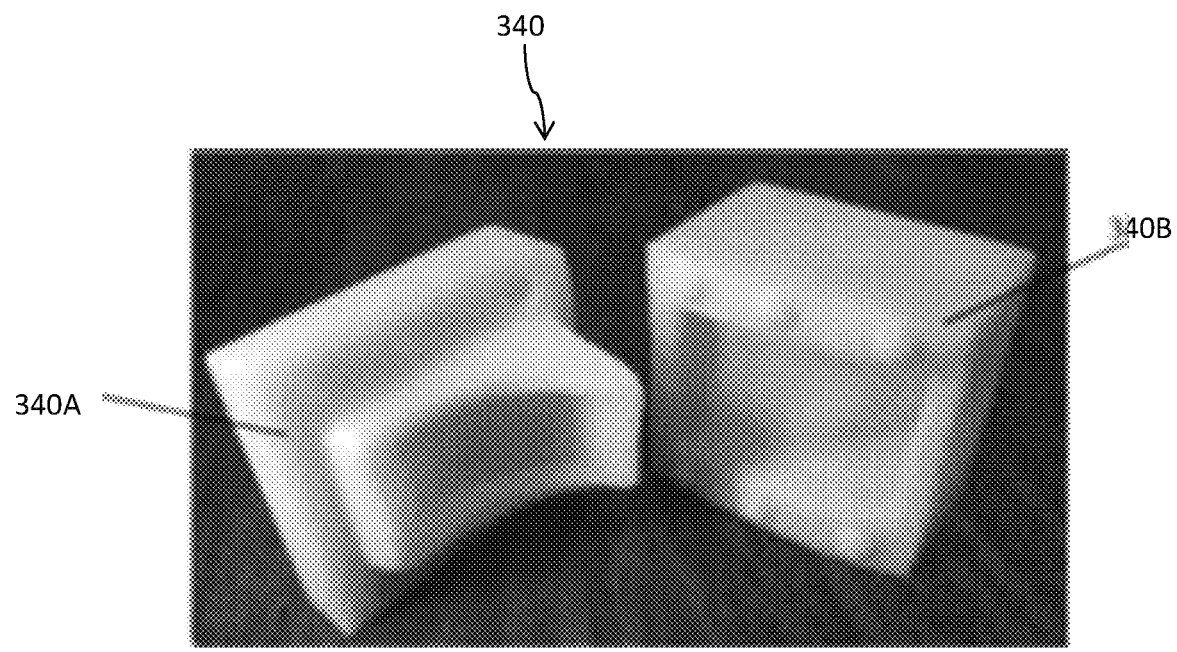
FIGS. 36A-B illustrate a 2-piece compression type mold formed from the digital model of FIGS. 35A-B.
Figure 36B:
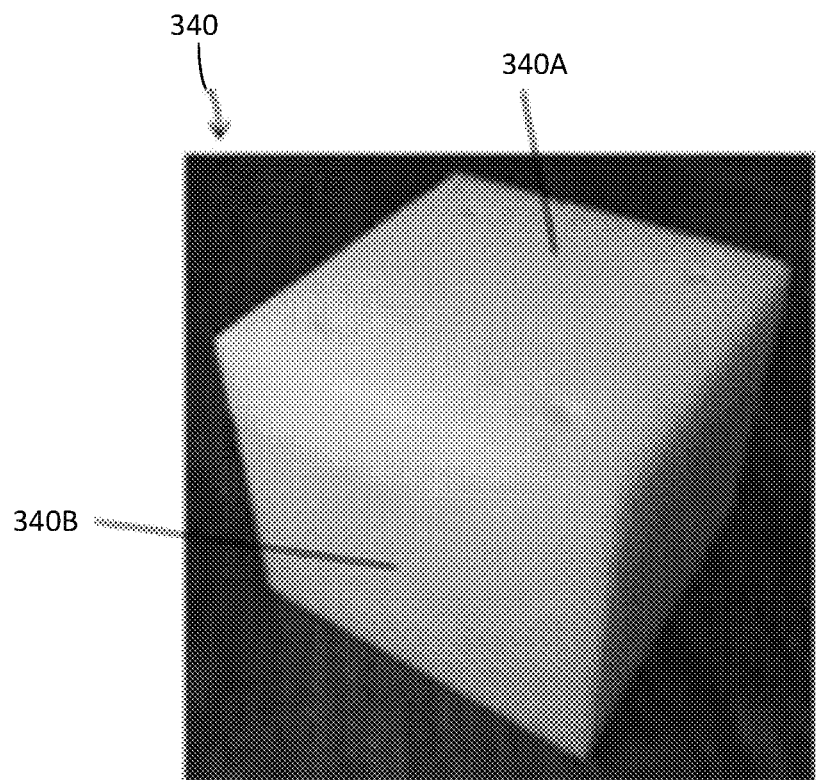
Figure 37:
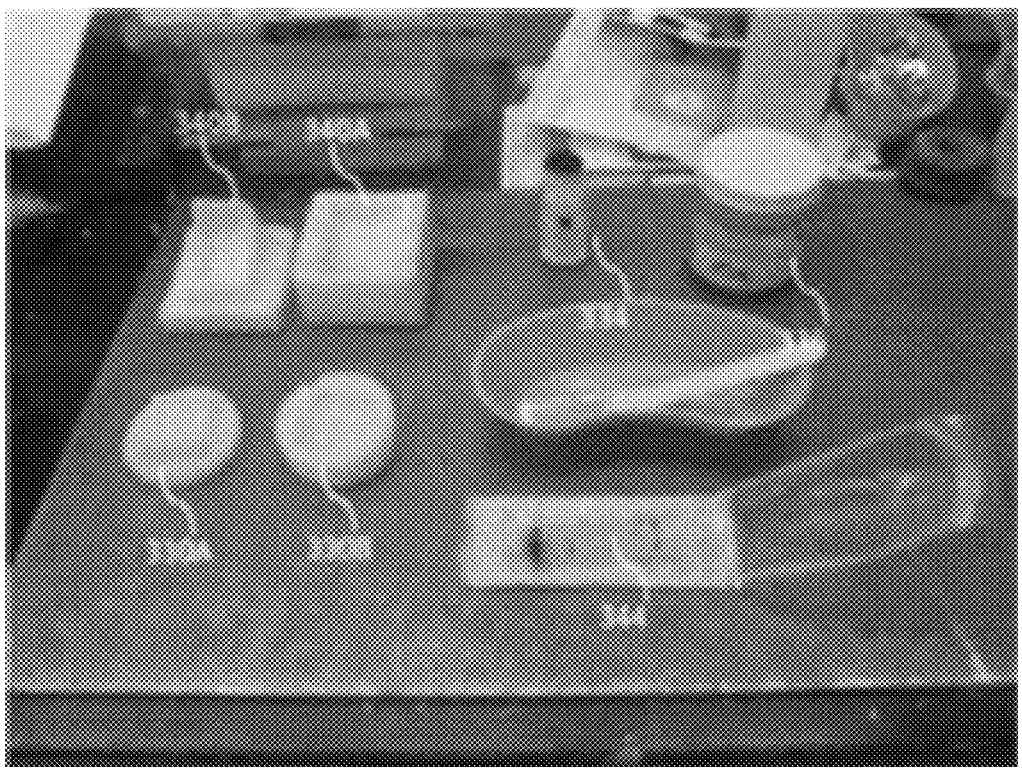
FIG. 37 illustrates the preparation for investment of platinum silicone for a radiation oncology bolus.
Figure 38:
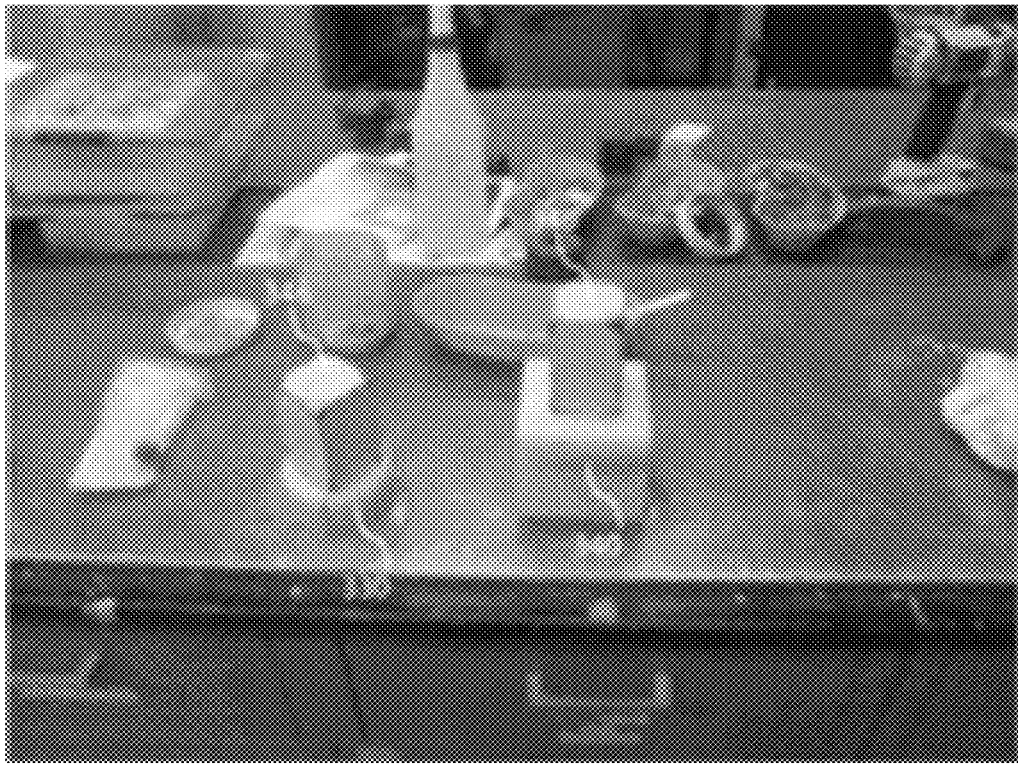
FIG. 38 illustrates exemplary radiation oncology bolus molds that have been invested with platinum silicone.

Referring next to FIGS. 33-36, exemplary radiation oncology bolus structures 332, 342 are illustrated. A bolus structure 332, 342 is typically used to enhance dosimetry of radiation treatment and to avoid direct contact with unwanted areas of the body during radiation treatment. The bolus structure 332, 342 may be formed from method 160 (FIG. 15) or method 180 (FIG. 16). Referring to FIGS. 33 and 34, an exemplary mold 330 is illustrated for forming a radiation oncology bolus structure 332. Mold 330 is illustratively a 2-piece compression type mold formed from pieces 330A, 330B, wherein the pieces 330A and 330B define a cavity for forming the bolus structure 332. Referring to FIGS. 35 and 36, an exemplary mold 340 is illustrated for investing a radiation oncology bolus structure 342. The bolus structure 342 may be formed from method 160 (FIG. 15) or method 180 (FIG. 16). Mold 342 is illustratively a 2-piece compression type mold formed from pieces 330A, 330B, wherein the pieces 330A and 330B define a cavity for forming the bolus structure 332. FIGS. 37 and 38 illustrate the preparation for investment of platinum silicone for molds 330 (FIGS. 33, 34) and 340 (FIGS. 35, 36). Investment of the platinum silicone is performed by mixing the catalyst 334 and silicone 336 and filling the molds 330 and 340 with a measuring device 344. A weight 346 is added to compress each mold.

Figure 39:
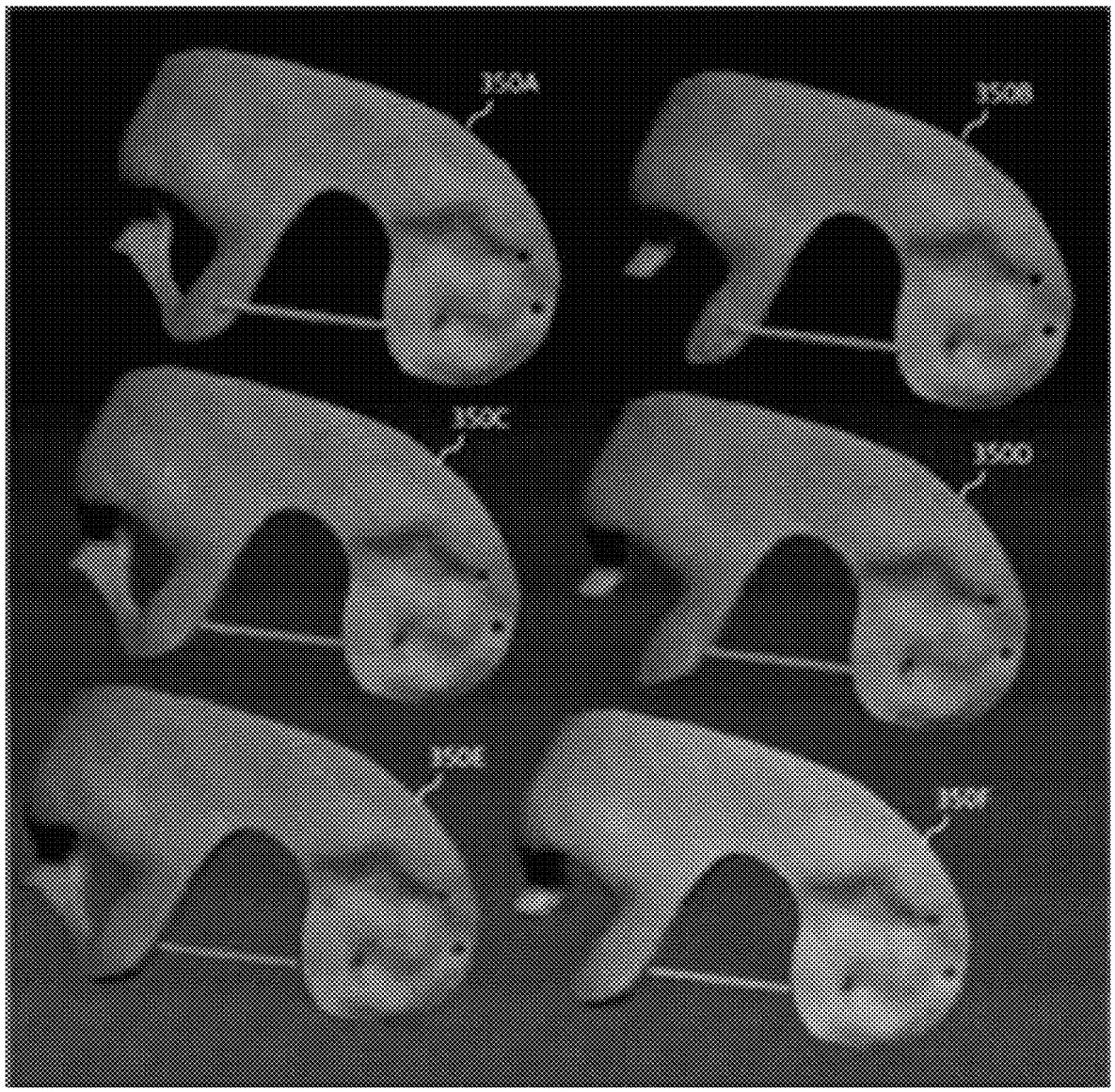
FIG. 39 illustrates a digital model of six exemplary surgical guides.
Figure 40:
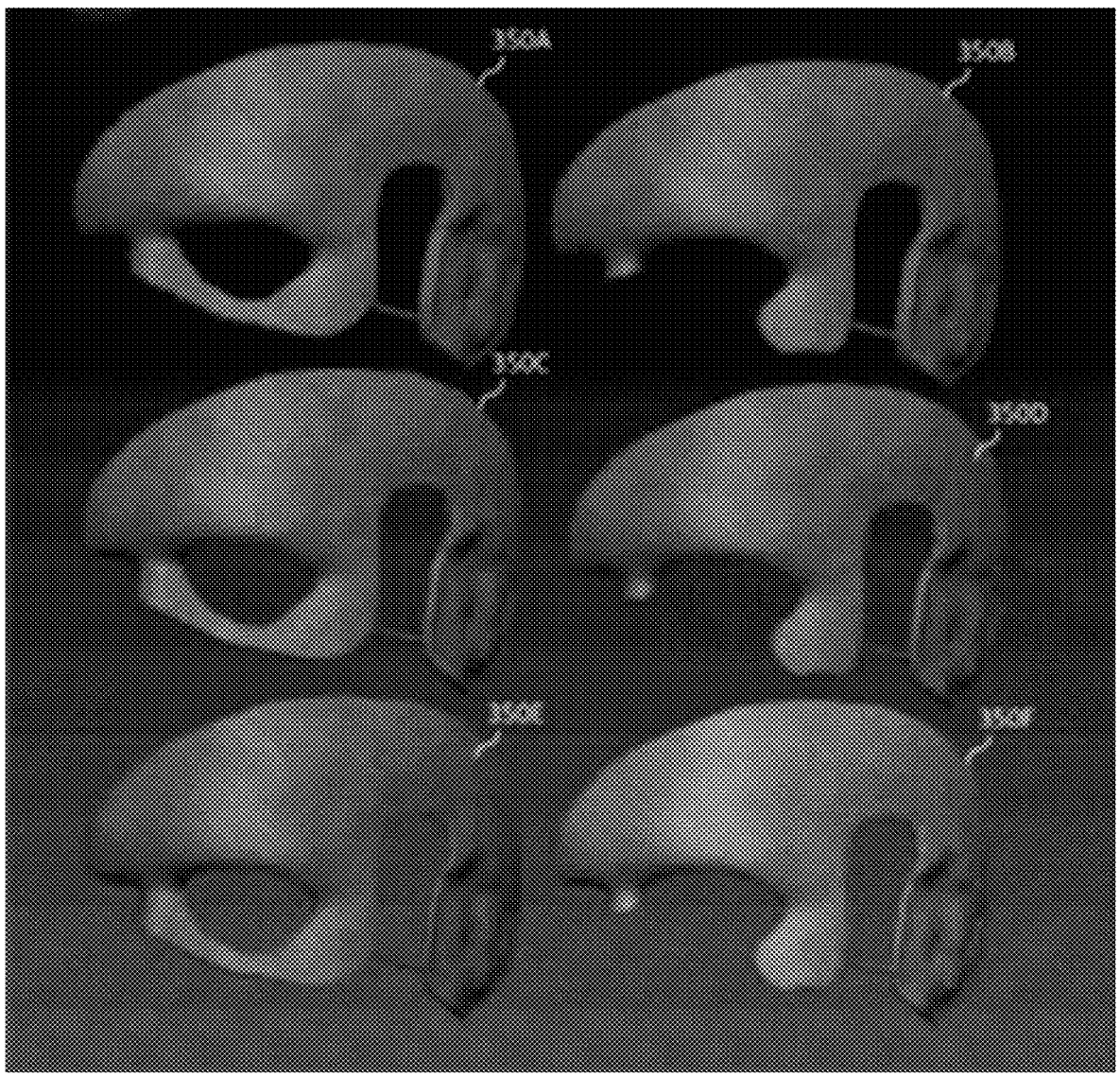
FIG. 40 illustrates another view of the six surgical guides of FIG. 39

Referring next to FIGS. 39 and 40, digital models of six exemplary surgical guides 350A-350F in the graphic modeling software application is ZBrush are illustrated. In some aspects, the surgical guides 350A-350F may be formed from method 130 (FIG. 14). The exemplary surgical guides 350A-350F may be used in the placement of titanium implants for an auricular prosthesis.

Figure 41:
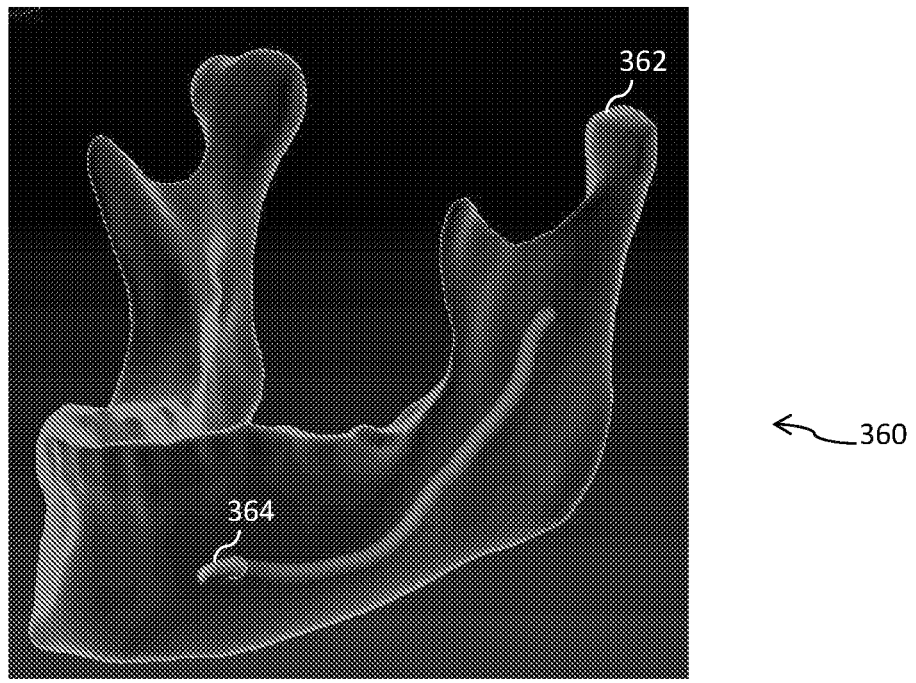
FIG. 41 illustrates a digital model of a pre-surgical model showing the location of the mandibular nerve inside the mandible.
Figure 42:
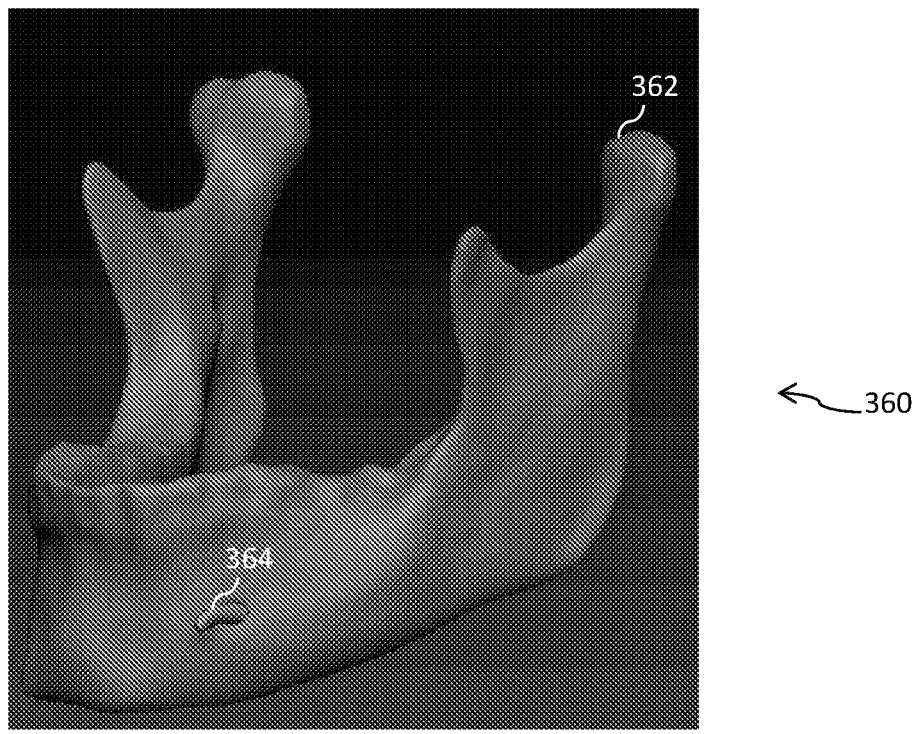
FIG. 42 illustrates another view of the pre-surgical model of FIG. 41.
Figure 43:
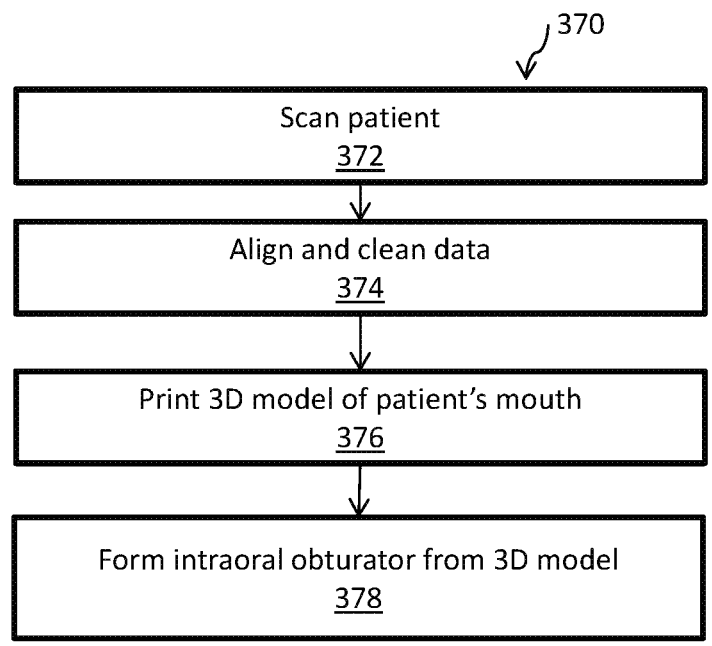
FIG. 43 illustrates an exemplary workflow for forming an intraoral obturator.

Referring next to FIGS. 41 and 42, a digital pre-surgical model 360. Pre-surgical model 360 illustrates the shape of the patient's mandible 362, as well as the location of the mandibular nerve 364. In some aspects, the pre-surgical model 360 may be formed from method 210 (FIG. 17). In some aspects, the portion of the model 360 relating to the mandible 362 and mandibular nerve 364 are printed from a different material, allowing the printed model to have different properties for each system. As shown in FIG. 41, the mandible 362 may be transparent, allowing a user to see the location of mandibular nerve 364. Mandible 362 and mandibular nerve 364 may be printed in a different color and/or printed with a different shape, density, thickness, and/or size to provide various surface tensions, hardness, and/or flexibility for each portion of the model. The 3D printed model may then be used to prepare a surgical guide. In an exemplary aspect, a plate for use as part of the guide may be bent around the model of the mandible 362, enabling a user to plant holes for use in implanting a prosthesis or surgical implant that will not harm roots of the teeth or the mandibular nerve 364.

Referring next to FIGS. 43-47, a method 370 for forming an intraoral obturator 372 (FIGS. 46-47) for a patient having a hole in his or her mouth is provided. In block 372, a scan of the patient's mouth is obtained, such as intraoral and/or extraoral scanning and photogrammetry, using a scanning apparatus 32 (FIG. 4). Exemplary scans may be obtained from photogrammetry systems such as the 3dMDface system or the Go! SCAN 50 three dimensional scanner available from Creaform Inc., Levis, Quebec, Canada. In block 374, the scan data obtained in block 372 is input into a suitable device, such as design apparatus 34 (FIG. 4) and the scan data is aligned and data artifacts are removed using a data alignment tool, such as Geomagic Design X, available from 3D Systems, Rock Hill, S.C. Block 374 results in a data set representing a solid surface of the patient's scan area without gaps, holes, or other data artifacts. In block 376, a three-dimensional model of the data set from block 374 is printed, such as with a rapid prototyping device 36 (FIG. 4), such as a 3D printer. An intraoral obturator is then formed in block 378 using the three-dimensional printed model obtained in block 376. By forming the obturator from the three-dimensional model, there is no need to form an impression directly from the patient's mouth. This may be beneficial to the patient, particularly where the patient's mouth has unhealed injuries.

Figure 46:
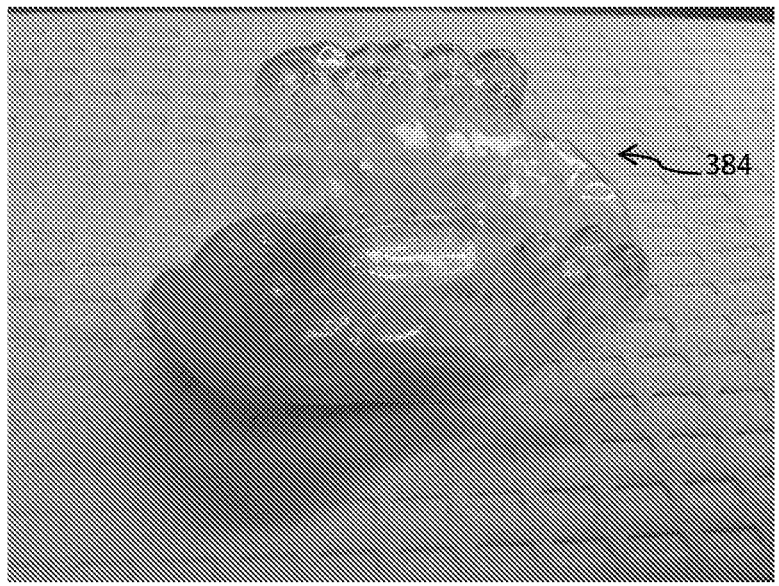
FIG. 46 illustrates an obturator formed based on the model in FIG. 44.
Figure 47:
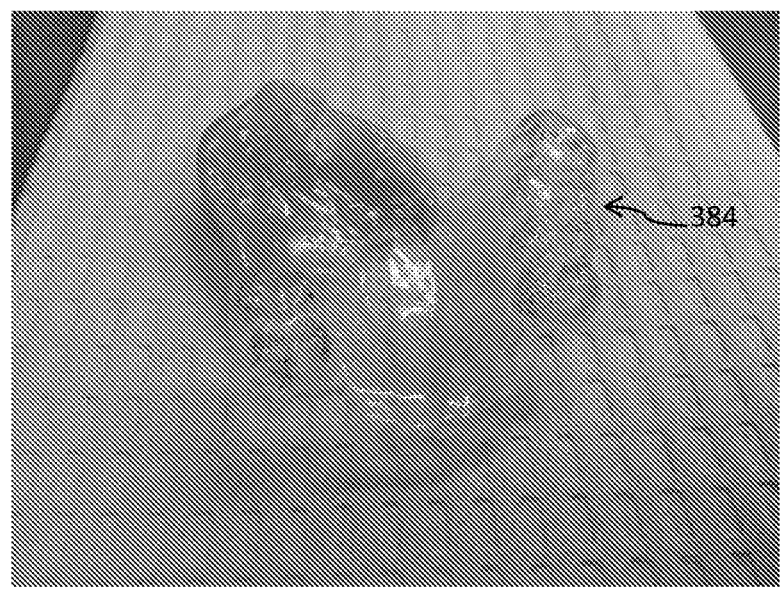
FIG. 47 illustrates another view of the obturator of FIG. 46.

An exemplary digital model 380 of the interior of the patient's mouth formed in block 374 is illustrated. As shown in the comparison of the photograph in FIG. 45A and the portion 382 of the model illustrated in FIG. 45B, the model provides a substantial likeness of the patient's mouth. FIGS. 46 and 47 illustrate the obturator 384 formed in block 378 from the three-dimensional printed model.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of forming a digitally sculpted radiation oncology bolus to enhance dosimetry of radiation treatment and avoid direct radiation contact with unwanted areas of a patient's body during radiation treatment, the method comprising:

receiving, by a computing device, topographical scan data of the patient, the topographical scan data being obtained by topographically scanning the patient with a no-contact laser scanner;

receiving, by the computing device, computerized tomography (CT) or magnetic resonance imaging (MRI) image data, the CT or MRI image data being obtained by performing a CT scan or MRI scan on the patient;

determining, by the computing device, a flesh and bone geometry of the patient based on subjecting the CT or (MRI) image data to an isosurface module;

analyzing, by the computing device, the topographical scan data and the CT or MRI image data to separate data relating to the radiation oncology bolus from other patient data;

aligning, by the computing device, the topographical scan data and the CT or MRI image data to provide a high-fidelity mesh comprising the topographical scan data superimposed over the flesh and bone geometry of the patient;

identifying and removing, by the computing device, scan artifacts in the topographical scan data using a graphics modeling software;

designing, by the computing device, a digital model of the radiation oncology bolus;

designing, by the computing device, a digital model of a radiation oncology bolus mold having a mold cavity for forming the radiation oncology bolus based on the digital model of the radiation oncology bolus;

printing, by the computing device, the radiation oncology bolus mold based on the digital model of the radiation oncology bolus mold, the radiation oncology bolus mold comprising a polymer material; and filling, by the computing device, the mold cavity in the printed radiation oncology bolus mold to form the radiation oncology bolus for the patient.

2. The method of claim 1, further comprising performing, by the computing device, a Boolean subtraction on the topographical scan data to subtract out a thickened bolus.

3. The method of claim 1, wherein the radiation oncology bolus is scaffold-free.

4. The method of claim 1, wherein the radiation oncology bolus mold is scaffold-free.

5. The method of claim 1, wherein the polymer material of radiation oncology bolus mold is selected from a group consisting of polylactic acid, acrylonitrile butadiene styrene, and methacrylate polymer.

6. The method of claim 1, wherein the scan artifacts include data errors or errors due to soft tissue presence.

7. The method of claim 1, wherein printing the radiation oncology bolus mold includes printing the radiation oncology bolus mold with a rapid prototyping selected from a group consisting of three-dimensional printing, additive manufacturing, stereolithography (SLA), fused deposition modeling (FDM), selective laser sintering (SLS), selective laser melting (SLM), electronic beam melting (EBM), laminated object manufacturing (LOM), continuous liquid interface production (CLIP), and a subtractive manufacturing method.

* * * * *